(12) United States Patent
Clarke et al.

(10) Patent No.: US 9,127,057 B2
(45) Date of Patent: Sep. 8, 2015

(54) ANTI-IL-23 HETERODIMER SPECIFIC ANTIBODIES

(75) Inventors: Adam William Clarke, Macquarie Park (AU); Anthony G. Doyle, Macquarie Park (AU); Matthew Pollard, Macquarie Park (AU); Stephen Tran, Macquarie Park (AU)

(73) Assignee: Teva Pharmaceuticals Ausralia Pty Ltd, Macquarie Park, NSW (AU)

(*) Notice: Subject to any disclaimer, the term of this patent is extended or adjusted under 35 U.S.C. 154(b) by 166 days.

(21) Appl. No.: 13/810,474

(22) PCT Filed: Jul. 20, 2011

(86) PCT No.: PCT/AU2011/000923
§ 371 (c)(1),
(2), (4) Date: Jan. 16, 2013

(87) PCT Pub. No.: WO2012/009760
PCT Pub. Date: Jan. 26, 2012

(65) Prior Publication Data
US 2013/0115166 A1 May 9, 2013

Related U.S. Application Data

(60) Provisional application No. 61/384,945, filed on Sep. 21, 2010.

(30) Foreign Application Priority Data

Jul. 20, 2010 (AU) ............................... 2010903234

(51) Int. Cl.
*A61K 39/395* (2006.01)
*C07K 16/24* (2006.01)
*A61K 39/00* (2006.01)

(52) U.S. Cl.
CPC ......... *C07K 16/244* (2013.01); *A61K 2039/505* (2013.01); *C07K 2317/21* (2013.01); *C07K 2317/24* (2013.01); *C07K 2317/32* (2013.01); *C07K 2317/33* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,593,089 A | 6/1986 | Wang et al. |
| 4,676,980 A | 6/1987 | Segal et al. |
| 4,751,190 A | 6/1988 | Chiapetta et al. |
| 4,816,397 A | 3/1989 | Boss et al. |
| 4,816,567 A | 3/1989 | Cabilly et al. |
| 5,225,539 A | 7/1993 | Winter |
| 5,260,203 A | 11/1993 | Ladner et al. |
| 5,516,637 A | 5/1996 | Huang et al. |
| 5,565,332 A | 10/1996 | Hoogenboom et al. |
| 5,571,728 A | 11/1996 | Kraus |
| 5,585,089 A | 12/1996 | Queen et al. |
| 5,731,168 A | 3/1998 | Carter et al. |
| 5,807,715 A | 9/1998 | Morrison et al. |
| 5,837,821 A | 11/1998 | Wu |
| 5,844,094 A | 12/1998 | Hudson et al. |
| 5,885,793 A | 3/1999 | Griffiths et al. |
| 6,054,297 A | 4/2000 | Carter et al. |
| 6,113,898 A | 9/2000 | Anderson et al. |
| 6,204,023 B1 | 3/2001 | Robinson et al. |
| 6,248,516 B1 | 6/2001 | Winter et al. |
| 6,248,597 B1 | 6/2001 | Eda et al. |
| 6,291,158 B1 | 9/2001 | Winter et al. |
| 6,300,064 B1 | 10/2001 | Knappik et al. |
| 6,331,415 B1 | 12/2001 | Cabilly et al. |
| 6,423,538 B1 | 7/2002 | Wittrup et al. |
| 6,797,482 B2 | 9/2004 | Woods et al. |
| 7,083,784 B2 | 8/2006 | Dall'Acqua et al. |
| 7,205,159 B2 | 4/2007 | Cole et al. |
| 7,217,797 B2 | 5/2007 | Hinton et al. |
| 7,217,798 B2 | 5/2007 | Hinton et al. |
| 7,229,619 B1 | 6/2007 | Young et al. |
| 7,247,711 B2 | 7/2007 | Benson et al. |
| 7,270,969 B2 | 9/2007 | Watt et al. |
| 7,566,771 B1 | 7/2009 | Adair et al. |
| 7,732,578 B2 | 6/2010 | Foote |
| 7,807,160 B2 | 10/2010 | Presta et al. |
| 2003/0039649 A1 | 2/2003 | Foote |

(Continued)

FOREIGN PATENT DOCUMENTS

| EP | 0569141 | 11/1993 |
|---|---|---|
| WO | 9958661 | 11/1999 |

(Continued)

OTHER PUBLICATIONS

Brown et al. Tolerance to Single, but Not Multiple, Amino Acid Replacements in Antibody VH CDR2. J Immunol. May 1, 1996;156(9):3285-91.*
Clarke, A.W., et al., "A novel class of anti-IL-12p40 antibodies. Potent neutralization via inhibition of IL-12-IL-12RB2 and IL-23-IL23R", Landes Bioscience (Sep./Oct. 2010), vol. 2, No. 5, pp. 539-549.
Bodanszky, M., "In search of new methods in peptide synthesis. A review of the last three decades", Int. J. Pept Protein Res., May 1985; 25(5); 449-74.
Chothia, C., et al., "Canonical structures for the hypervariable regions of immunoglobulins", J. Mol. Biol., Aug. 20, 1987; 196(4); 901-17.
Chothia, C., et al., "Conformation s of immunoglobulin hypervariable regions", Nature, Dec. 21-28, 1989; 342(6252): 877-83.

(Continued)

*Primary Examiner* — Dong Jiang
(74) *Attorney, Agent, or Firm* — Stradley Ronon Stevens & Young, LLP

(57) ABSTRACT

The present disclosure provides an isolated or recombinant IL-23-binding protein comprising an antigen binding domain of an antibody, wherein the antigen binding domain specifically binds to IL-23 but does not significantly bind to an IL-12p40 subunit and does not significantly bind to an IL-23p19 subunit when they are not components of IL-23. The present disclosure also provides uses of the IL-23-binding protein.

16 Claims, 17 Drawing Sheets

(56) References Cited

U.S. PATENT DOCUMENTS

| | | |
|---|---|---|
| 2003/0124619 A1 | 7/2003 | Weigl et al. |
| 2004/0228761 A1 | 11/2004 | Owens et al. |
| 2004/0265926 A1 | 12/2004 | Ng |
| 2005/0037000 A1 | 2/2005 | Stavenhagen et al. |
| 2006/0067936 A1 | 3/2006 | Benson et al. |
| 2007/0135620 A1 | 6/2007 | Chamberlain et al. |
| 2007/0148167 A1 | 6/2007 | Strohl |
| 2008/0152586 A1 | 6/2008 | Hudson et al. |
| 2009/0041770 A1 | 2/2009 | Chamberlain et al. |
| 2009/0247455 A1 | 10/2009 | Fear |

FOREIGN PATENT DOCUMENTS

| | | |
|---|---|---|
| WO | 0034317 | 6/2000 |
| WO | 2004108158 | 12/2004 |
| WO | 2007005955 | 1/2007 |
| WO | 2007019620 | 2/2007 |
| WO | 2007027714 | 3/2007 |
| WO | 2009082624 | 7/2009 |
| WO | 2010027766 | 3/2010 |
| WO | 2010059821 | 5/2010 |
| WO | 2010080538 | 7/2010 |

OTHER PUBLICATIONS

Al-Lazikani, B., et al., "Standard conformations for the canonical structures of immunoglobulins", J. Mol. Biol., Nov. 7, 1997; 273(4); 927-48.
Honegger, A., et al., "Yet another numbering scheme for immunoglobulin variable domains: an automatic modeling and analysis tool", J. Mol. Biol., Jun. 8, 2001; 309(3); 657-70.
Lonberg, N., et al., "Antigen-specific human antibodies from mice comprising four distinct genetic modifications", Nature, Apr. 28, 1994; 368(6474); 856-9.
Koehler, G., et al., Continuous cultures of fused cells secreting antibody of predefined specificity, Nature, Aug. 7, 1975; 256(5517); 495-7.
Largaespada, D., et al., "The activity of an ABL-MYC retrovirus in fibroblast cell lines and in lymphocytes", Curr. Top. Microbiol. Immunol., 1990; 166: 91-6.
Jones, M.L., et al., "A method for rapid, ligation-independent reformatting of recombinant monoclonal antibodies", J. Immunol. Methods, Mar. 31, 2010; 354(1-2): 85-90.
Jostock, T., et al., "Rapid generation of functional human IgG antibodies derived from Fab-on-phage display libraries", J. Immunol. Methods, 2004 Jun.; 289(1-2); 65-80.
Needleman, S.B., et al., "A general method applicable to the search for similarities in the amino acid sequence of two proteins", J. Mol. Biol., Mar. 1970; 48(3); 443-53.
Kyte, J., et al., "A simple method for displaying the hydropathic character of a protein", J. Mol. Biol., May 5, 1982; 157 (1); 105-32.
Thie, H., et al., "Affinity maturation by phage display", Methods Mol. Biol., 2009; 525; 309-22.
Kopsidas, G., et al., "In vitro improvement of a shark IgNAR antibody by Qbeta replicase mutation and ribosome display mimics in vivo affinity maturation", Immunol. Lett., Nov. 15, 2006; 107(2); 163-8.
Stemmer, W.P., "Rapid evolution of a protein in vitro by DNA shuffling", Nature, Aug. 4, 1994, 370(6488); 389-91.
Sakaguchi, et al., "Altered thymic T-cell selection due to a mutation of the ZAP-70 gene causes autoimmune arthritis in mice," Nature, 426: 454-460, 1995.
Bendele, A.M., "Animal models of rheumatoid arthritis," J. Musculoskel. Neuron. Interact., 1(4): 377-385, 2001.
Rich, R.L., et al., "Advances in surface plasmon resonance biosensor analysis", Curr. Opin. Biotechnol., Feb. 2000; 11(1): 54-61.
Englebienne, P., et al., "Use of colloidal gold surface plasmon resonance peak shift to infer affinity constants from the interctions between protein antigens and antibodies specific for single or multiple epitopes", Analyst, Jul. 1998; 123(7); 1599-603.
Kim, J.K., et al., "Localization of the site of the murine IgG1 molecule that is involved in binding the murine intestinal Fc receptor", Eur. J. Immunol., Oct. 1994; 24(10); 2429-34.
Kim, et al., "Identifying amino acid residues that influence plasma clearance of murine IgG1 fragments by site directed mutagenesis", Eur. J. Immunol., Mar. 1994; 24(3); 542-8.
Kilpatrick, et al., "Gene Gun Delivered DNA-Based Immunizations Mediate Rapid Production of Murine Monoclonal Antibodies to the Flt-3 Receptor", Hybridoma 17; 569-576, 1998.
Lo, B.K., "Antibody humanization by CDR grafting", Methods Mol. Biol., 2004; 248; 135-59.
Marks, J.D., et al., "Selection of human antibodies from phage display libraries", Methods Mol. Biol., 2004; 248; 161-76.
Chames, P., et al., "Selection of antibodies against biotinylated antigens", Methods Mol. Biol., 2002; 178; 147-57.
Sarantakis, D., et al., "A Novel Cyclic Undecapeptide, WY-40, 770, with Prolonged Growth Hormone Release Inhibiting Activity," Biochem. Biophys. Res. Commun., 76, 1976; 336-342.
Merrifield, R.B., "Solid Phase Peptide Synthesis. I. The Synthesis of a Tetrapeptide", of J. Am. Chem. Soc., 85, 1963, 2149-2154.
Giudicelli, et al., "IMGT, the international ImMunoGeneTics database", Nucleic Acids Research, 1197, vol. 25, No. 1, pp. 206-211.
Padlan, et al., "Identification of specificity-determining residues in antibodies", FASEB J., Jan. 1995;9(1):133-9.
Trinchieri, et al., "The IL-12 Family of Heterodimeric Cytokines: New Players in the Regulation of T Cell Responses", Immunity, vol. 19, Nov. 2003, pp. 641-644.
Shalaby, M. R., et al., "Development of Humanized Bispecific Antibodies Reactive with Cytotoxic Lymphocytes and Tumor Cells Overexpressing HER2 Protooncogene", J. Exp. Med., vol. 175, Jan. 1992, pp. 217-225.
Marsh, J. L., et al., "Expaneded polyglutamine peptides alone are intrinsically cytotoxic and cause neurodegeneration in *Drosophila*", Human Molecular Genetics, 2000, vol. 9, No. 1, pp. 13-25.
Tang, Q., et al., "In Vitro-expanded Antigen-specific Regulatory T Cells Suppress Autoimmune Diabetes", J. Exp. Med., vol. 199, No. 11, Jun. 7, 2004, pp. 1455-1465.
Trenado, A., et al., "Recipient-type specific CD4+CD25+ regulatory T cells favor immune reconstitution and control graft-versus-host disease while maintaining graft-versus-leukemia", J. Clin. Inves., Dec. 2003, vol. 112, No. 11, pp. 1688-1696.
Wang, H., et al., "TGF-B-dependent suppressive function of Tregs requires wild-type levels of CD18 in a mouse model of psoriasis", J. Clin. Inves., Jul. 2008, vol. 118, No. 7, pp. 2629-2639.
Durocher, Y., et al., "High-level and high-throughput recombinant potein production by transient transfection of suspension-growing human 293-EBNA1 cells", Nucelic Acids Research, 2002, vol. 30, No. 2, pp. 2-9.
Edelman, G. M., et al., "The Covalent Structure of an Entire gamma-Immunoglobulin Molecule", Proc. N. A. S., vol. 63, 1969, pp. 78-85. NCBI Accession No. P10857.1.
International Search Report and Written Opinion dated Sep. 11, 2011 issued in counterpart application No. PCT/AU2011/000923 filed Jul. 20, 2011.
Extended European Search Report dated Oct. 6, 2014 issued in counterpart application EP 11 80 9081.

\* cited by examiner

```
                         |      CDR1      |                 |   CDR2     |
SEQ ID NO: 39  QVQLQESGPGLVKPSETLSLTCTVS GGSISSYNVH WIRQPPGKGLEWIG VIWTGGSTDYN
SEQ ID NO: 42  QVQLQESGPGLVKPSETLSLTCTVS GGSISSYNVH WIRQPPGKGLEWIG VIWTGGSTDYN
SEQ ID NO: 41  QVQLQESGPGLVKPSETLSLTCTVS GGSIISYNVH WIRQPPGKGLEWIG VIWTGGSTDYN
SEQ ID NO: 38  QVQLQESGPGLVKPSETLSLTCTVS GGSLSSYNVH WIRQPPGKGLEWIG VIWTGGSTDYN
SEQ ID NO: 32  QVQLQESGPGLVKPSETLSLTCTVS GFSISSYNVH WIRQPPGKGLEWIG VIWTGGSTDYN
SEQ ID NO: 33  QVQLQESGPGLVKPSETLSLTCTVS GFSLISYNVH WIRQPPGKGLEWIG VIWTGGSTDYN
SEQ ID NO: 34  QVQLQESGPGLVKPSETLSLTCTVS GFSLISYNVH WIRQPPGKGLEWIG VIWTGGSTDYN
SEQ ID NO: 31  EVQLQQWGAGLLKPSETLSLTCAVY GFSLISYNVH WIRQPPGKGLEWIG VIWTGGSTDYN
SEQ ID NO: 30  EVQLQQWGAGLLKPSETLSLTCAVY GFSLISYNVH WIRQPPGKGLEWIG VIWTGGSTDYN
SEQ ID NO: 36  EVQLQQWGAGLLKPSETLSLTCAVY GGSFSSYNVH WIRQPPGKGLEWIG VIWTGGSTDYN
SEQ ID NO: 40  EVQLQQWGAGLLKPSETLSLTCAVY GGSFSSYNVH WIRQPPGKGLEWIG VIWTGGSTDYN
SEQ ID NO: 43  QVQLQESGPGLVKPSQTLSLTCTVS GGSISSYNVH WIRQPPGKGLEWIG VIWTGGSTDYN
SEQ ID NO: 44  QVQLQESGPGLVKPSQTLSLTCTVS GGSISSYNVH WIRQPPGKGLEWIG VIWTGGSTDYN
SEQ ID NO: 37  QVQLQESGPGLVKPSQTLSLTCTVS GFSLISYNVH WIRQPPGKGLEWIG VIWTGGSTDYN
SEQ ID NO: 35  QVQLQESGPGLVKPSQTLSLTCTVS GFSLISYNVH WIRQPPGKGLEWIG VIWTGGSTDYN
SEQ ID NO:  7  QVQLKESGPGLVQPSQTLSLTCTVS GFSLISYNVH WVRQPRGKGLEWMG VIWTGGSTDYN
               :***::.*.**::**:******:**  *:* *****   *:*** ******:* ***********
Consensus      XVQLXXXGXGLXXPSXTLSLTCXVX GXSXXSYNVH WXRQPXGKGLEWXG VIWTGGSTDYN
(SEQ ID NO: 26) Q   QEW P  VK  Q      T S   F II        I  P     I
                E   KQS A  LQ  E      A Y   G LS        V     R     M
                                            F

|  CDR2  |                                       |    CDR3    |
SEQ ID NO: 39  PSLKS RVTISRDTSKNQFSLKLSSVTAADTAVYYCAR DKYGLFPGYFDY WGQGTLVTVSS
SEQ ID NO: 42  PSLKS RVTISVDTSKNQFSLKLSSVTAADTAVYYCAR DKYGLFPGYFDY WGQGTLVTVSS
SEQ ID NO: 41  PSLKS RVTISRDTSKNQFSLKLSSVTAADTAVYYCAR DKYGLFPGYFDY WGQGTLVTVSS
SEQ ID NO: 38  PSLKS RVTISRDTSKNQFSLKLSSVTAADTAVYYCAR DKYGLFPGYFDY WGQGTLVTVSS
SEQ ID NO: 32  PSLKS RVTISRDTSKNQFSLKLSSVTAADTAVYYCAR DKYGLFPGYFDY WGQGTLVTVSS
SEQ ID NO: 33  PSLKS RVTISRDTSKNQFSLKLSSVTAADTAVYYCAR DKYGLFPGYFDY WGQGTLVTVSS
SEQ ID NO: 34  PSLKS RVTISVDTSKNQFSLKLSSVTAADTAVYYCAR DKYGLFPGYFDY WGQGTLVTVSS
SEQ ID NO: 31  SVLKS RVTISRDTSKNQFSLKLSSVTAADTAVYYCAR DKYGLFPGYFDY WGQGTLVTVSS
SEQ ID NO: 30  SVLKS RVTISVDTSKNQFSLKLSSVTAADTAVYYCAR DKYGLFPGYFDY WGQGTLVTVSS
SEQ ID NO: 36  SVLKS RVTISRDTSKNQFSLKLSSVTAADTAVYYCAR DKYGLFPGYFDY WGQGTLVTVSS
SEQ ID NO: 40  SVLKS RVTISVDTSKNQFSLKLSSVTAADTAVYYCAR DKYGLFPGYFDY WGQGTLVTVSS
SEQ ID NO: 43  SVLKS RVTMSRDTSKNQFSLKVNSVTAADTAVYYCAR DKYGLFPGYFDY WGQGTLVTVSS
SEQ ID NO: 44  SVLKS RVTMSVDTSKNQFSLKVNSVTAADTAVYYCAR DKYGLFPGYFDY WGQGTLVTVSS
SEQ ID NO: 37  SVLKS RVTMSVDTSKNQFSLKVNSVTAADTAVYYCAR DKYGLFPGYFDY WGQGTLVTVSS
SEQ ID NO: 35  SVLKS RVTMSRDTSKNQFSLKVNSVTAADTAVYYCAR DKYGLFPGYFDY WGQGTLVTVSS
SEQ ID NO:  7  SVLKS RLSISRDTSKSQVFLKMHSLQTEDIGTYYCAR DKYGLFPGYFDY WGQGVMVTVSS
               .***  *:::* ****.*..**: *: . *  .***** ************ ****.:*****
Consensus      XXLKS RXXXSXDTSKXQXXLKXXSXXXXDXXXYYCAR DKYGLFPFYFDY WGQGXXVTVSS
(SEQ ID NO: 26) PV    LSI R    S FF  MH LQTE IGT                     VM
                SS    VTM V    N VS  VN VTAA TAV                     TL
                                     LS
```

Figure 7A

|  |  | CDR1 |  | CDR2 |
|---|---|---|---|---|
| SEQ ID NO: 32 | QVQLQESGPGLVKPSETLSLTCTVS | GFSISSYNVH | WIRQPPGKGLEWIG | <u>VIWTGGSTDYN</u> |
| SEQ ID NO: 33 | QVQLQESGPGLVKPSETLSLTCTVS | GFSLISYNVH | WIRQPPGKGLEWIG | <u>VIWTGGSTDYN</u> |
| SEQ ID NO: 31 | EVQLQQWGAGLLKPSETLSLTCAVY | GFSLISYNVH | WIRQPPGKGLEWIG | <u>VIWTGGSTDYN</u> |
| SEQ ID NO: 30 | EVQLQQWGAGLLKPSETLSLTCAVY | GFSLISYNVH | WIRQPPGKGLEWIG | <u>VIWTGGSTDYN</u> |
|  | :****: *.:*********:* | *: * | ********** | ********* |
| Consensus | XVQLQXXGXGLXKPSETLSLTCXVX | GFSXXSYNVH | WIRQPPGKGLEWIG | <u>VIWTGGSTDYN</u> |
| (SEQ ID NO: 28) | Q   EW P   V        T S |   II |  |  |
|  | E   QS A   L        A Y |   LS |  |  |

|  | CDR2 |  |  | CDR3 |  |
|---|---|---|---|---|---|
| SEQ ID NO: 32 | <u>PSLKS</u> | RVTISRDTSKNQFSLKLSSVTAADTAVYYCAR | DKYGLFPGYFDY | WGQGTLVTVSS |
| SEQ ID NO: 33 | <u>PSLKS</u> | RVTISRDTSKNQFSLKLSSVTAADTAVYYCAR | DKYGLFPGYFDY | WGQGTLVTVSS |
| SEQ ID NO: 31 | <u>SVLKS</u> | RVTISRDTSKNQFSLKLSSVTAADTAVYYCAR | DKYGLFPGYFDY | WGQGTLVTVSS |
| SEQ ID NO: 30 | <u>SVLKS</u> | RVTISVDTSKNQFSLKLSSVTAADTAVYYCAR | DKYGLFPGYFDY | WGQGTLVTVSS |
|  | . *** | ***** ************************** | ************ | *********** |
| Consensus | <u>XXLKS</u> | RVTISXDTSKNQFSLKLSSVTAADTAVYYCAR | DKYGLFPFYFDY | WGQGVLVTVSS |
| (SEQ ID NO: 28) | PV |        R |  |  |
|  | SS |        V |  |  |

Figure 7B

|  | | CDR1 | | CDR2 |
|---|---|---|---|---|
| SEQ ID NO: 45 | EIVLTQSPATLSLSPGERATLSC | KPSQSLLSSGNRKNYLA | WYQQKPGQAPRLLIY | YASTR |
| SEQ ID NO: 47 | EIVMTQSPATLSLSPGERATLSC | KPSQSLLSSGNRKNYLA | WYQQKPGQAPRLLIY | YASTR |
| SEQ ID NO: 48 | DIVMTQTPLSLPVTPGEPASISC | KPSQSLLSSGNRKNYLA | WYLQKPGQSPQLLIY | YASTR |
| SEQ ID NO: 46 | DIVMTQSPDSLAVSLGERATINC | KPSQSLLSSGNRKNYLA | WYQQKPGQPPKLLIY | YASTR |
| SEQ ID NO: 12 | DIVMTQSPFSLAVSEGEMVTINC | KPSQSLLSSGNRKNYLA | WYQQKPGQSPKLLIY | YASTR |
|  | :::* :*. : *: .::.* | *************** |  *****.*:** | *** |
| CONSENSUS<br>(SEQ ID NO: 27) | XIVXTQXPXXLXXXXGEXXXXXC<br>E M S FS AVSE MVTIN<br>D L T DT PLTL RASLS<br>          L S P P<br>          A | KPSQSLLSSGNRKNYLA | WYXQKPGQXPXLKIY<br>  Q      S K<br>  L      A R<br>          P Q | YASTR |

|  | CDR2 | | CDR3 | |
|---|---|---|---|---|
| SEQ ID NO: 45 | QS | GIPDRFSGSGSGTDFTLTISRLEPEDFAVYYC | LQHFNYPWT | FGGGTKVEIK |
| SEQ ID NO: 47 | QS | GIPARFSGSGSGTDFTLTISSLEPEDFAVYYC | LQHFNYPWT | FGGGTKAEIK |
| SEQ ID NO: 48 | QS | GVPDRFSGSGSGTDFTLKISRVEAEDVGVYYC | LQHFNYPWT | FGQGTKLEIK |
| SEQ ID NO: 46 | QS | GVPDRFSGSGSGTDFTLTISSLQAEDVAVYYC | LQHFNYPWT | FGQGTKLEIK |
| SEQ ID NO: 12 | QS | GVPDRFIGSGSGTDFTLTISDVQAEDLADYYC | LQHFNYPWT | FGGGTKLELK |
|  | ** | *:*  ******. ::... * | ******* |  *** *:* |
| CONSENSUS<br>(SEQ ID NO: 27) | QS | GXPXRFXGSGSGTDFTLXISXXXXEDXXXYYC<br>  V D I           T DVQA LAD<br>  I A S           K SLEP VGV<br>                    R F | LQHFNYPWT | FGXGTKXEXK<br>  G   L L<br>  Q   V I<br>        A |

Figure 7C

```
                                                     CDR1                         CDR2
SEQ ID NO: 45   EIVLTQSPATLSLSPGERATLSC KPSQSLLSSGNRKNYLA WYQQKPGQAPRLLIY YASTR
SEQ ID NO: 46   DIVMTQSPDSLAVSLGERATINC KPSQSLLSSGNRKNYLA WYQQKPGQPPKLLIY YASTR
                :**:**** :*::* *****:.* ***************** ******* *:.**** *****
CONSENSUS       XIVXTQSPXXLXXSXGERATIXC KPSQSLLSSGNRKNYLA WYQQKPGQXPXLLIY YASTR
(SEQ ID NO: 29) E   M    AS AV P     N                                  A K
                D   L    DT SL L     S                                  P R
```

```
                 CDR2                                               CDR3
SEQ ID NO: 45    QS GIPDRFSGSGSGTDFTLTISRLEPEDFAVYYC LQHFNYPWT FGGGTKVEIK
SEQ ID NO: 46    QS GVPDRFSGSGSGTDFTLTISSLQAEDVAVYYC LQHFNYPWT FGQGTKLEIK
                 ** *:**************** *:.** .***** ********* ** ***:***
CONSENSUS        QS GXPDRFSGSGSGTDFTLTISXLXXEDXAVYYC LQHFNYPWT FGXGTKXEIK
                 QS GXPDRFSGSGSGTDFTLTISXLXXEDXAVYYC LQHFNYPWT FGXGTKXEIK
(SEQ ID NO: 29)     V                    R QA F             G   L
                    I                    S EP V             Q   V
```

Figure 7D

SEQ ID NO 49    QVQLVESGGGLVKPGRSLRLSCAAS |CDR1 GFTFSSYAMH| WVRQAPGKGLEWVA |CDR2 VISYDGSNKYY|

SEQ ID NO 49    |CDR2 ADSVKG| RFTISRDNSKNTLYLQMNSLRAEDTAVYYCAK |CDR3 EKGMVRGYGMDV| WGQCTTVTV

SEQ ID NO 49    SS 121

Figure 7E

SEQ ID NO 50    QSVLTQPPSVSGAPGQRVTFSC |CDR1 TGSDSNIGAGYDVH| WYQQFPGRAPKLLIY |CDR2 GTNNRPS|

SEQ ID NO 50    GVPDRFSGSKSGASASLAITGLQVEDEADYYC |CDR3 QTFDTRLIASV| FGGGTQLTVLG

Figure 7F

ANTI-IL-23 HETERODIMER SPECIFIC ANTIBODIES

CROSS REFERENCE TO RELATED APPLICATIONS

This application is the U.S. National Phase of International Application No. PCT/AU2011/000923, filed on Jul. 20, 2011, and claims priority to U.S. Provisional Application No. 61/384,945 filed on Sep. 21, 2010, and Australian Patent Application No. 2010903234 filed on Jul. 20, 2010, the contents of each of these applications are incorporated herein by reference in their entirety and for all purposes.

REFERENCE TO A SEQUENCE LISTING

This application includes a Sequence Listing submitted electronically as a text file named 510922_ST25.txt, created on Jan. 4, 2013 with a size of 128,000 bytes. The Sequence Listing is incorporated by reference herein.

FIELD

The present disclosure relates to proteins that specifically bind to interleukin (IL)-23 and uses thereof.

BACKGROUND

Interleukin (IL)-23 was discovered by searching sequence databases with a computationally derived profil of members of the interleukin-6 helical cytokine family. This search led to the discovery of a novel cytokine subunit which was named IL-23p19 (p19) which was homologous to the IL-12p35 subunit. This IL-12p35 subunit dimerizes with IL-12p40 subunit to form IL-12. Expression of p19 with IL-12p40 led to the secretion of a heterodimeric protein which was called IL-23.

The p40 subunit of IL-23 has three domains labeled D1, D2 and D3. Each domain is a β-sheet structure with the D2 domain containing the C177 interchain disulphide bond. There is also an N-linked glycosylation site on D2.

The p19 subunit resembles IL-12p35 in that it contains a four helix bundle. However, a truncated helical length and a 'tilt' and 'roll' in IL23p19 relative to IL-12p35 results in an altered footprint. IL-23p19 also differs in the manner in which it interacts with IL-12p40 when compared to IL-12p35.

The specific effects of IL-23 on its target cell types are mediated by the IL-23R complex, which comprises IL-12β1 and IL-23R. IL-12β1 binding to IL-23 is mediated via the IL-12p40 subunit.

IL-23p19 of IL-23 is responsible for binding to IL-23R thereby conferring IL-23 selectivity on the IL-23R complex.

IL-23 is secreted by activated human macrophages as well as dendritic cells. IL-23 predominantly acts on memory T-cells and has been postulated to promote autoimmune disease through the regulation of IL-17A and IL-17F as demonstrated in the ability of murine splenocytes to secrete IL-17 in response to IL-23. In humans the IL-23/IL-17 pathway is present, and IL-23 has been shown to be a good inducer of IL-21, IL-22, IFN-γ, and TNF-α along with IL-17, all of which are pro-inflammatory cytokines. In vitro IL-6 and TGF-β1 promote the development of naïve T-cells to the $T_H17$ T-cell pathway. These cells are further driven in an autocrine manner via secretion of IL-21. IL-23 and/or IL-1β are thought to maintain cells in this $T_H17$ response.

Since both IL-12 and IL-23 contain a common subunit, it has been difficult to attribute disease states solely to overproduction of one interleukin or the other. However research indicates that IL-23 dysregulation has been implicated in psoriasis, Crohn's disease and multiple sclerosis, among other autoimmune diseases.

Given that IL-23 is involved in various pathological conditions, antagonists specific for this cytokine are desirable. However, specifically targeting this cytokine has proven difficult since both of the subunits of IL-23 are shared with other dimeric cytokines. For example, the IL-12p40 subunit is also a component of IL-12 and IL-23p19 is also a component of heterodimeric cytokines such as zcyto33f2 as described in U.S. Pat. No. 7,196,172.

SUMMARY

The present inventors have produced a protein that specifically binds to IL-23 but not to either of its component parts (IL-12p40 or IL-23p19) when not part of IL-23, e.g., IL-12p40 or IL-23p19 in isolation or when part of another cytokine (e.g., IL-12, both of which comprise IL-12p40; or zcyto33f2, which comprises IL-23p19). Such a protein is unlikely to cause the undesired effects of inhibiting the activity of cytokines that share the IL-12p40 or IL-23p19 subunit, and thus unlikely to have "off-target" effects in therapy. Moreover, such proteins provide the basis for specific tests to detect IL-23, e.g., in diagnosis/prognosis.

The present disclosure provides an isolated or recombinant IL-23-binding protein comprising an antigen-binding domain of an antibody, wherein the antigen-binding domain specifically binds to IL-23 but does not significantly bind to an IL-12p40 subunit and does not significantly bind to an IL-23p19 subunit when they are not components of IL-23.

The skilled artisan will understand from the foregoing, that the inclusion of the antigen-binding domain in the IL-23-binding protein means that the protein also specifically binds to IL-23 but does not significantly bind to an IL-12p40 subunit and does not significantly bind to an IL-23p19 subunit when they are not components of IL-23.

In one example, the antigen binding domain specifically binds to the heterodimeric interface of IL-23.

The present disclosure additionally or alternatively provides an isolated or recombinant IL-23-binding protein comprising an antigen binding domain of an antibody, wherein the antigen binding domain specifically binds to the heterodimeric interface of IL-23 but does not significantly bind to an IL-12p40 subunit and an IL-23p19 subunit when they are not components of IL-23.

The present disclosure additionally or alternatively provides an isolated or recombinant IL-23-binding protein comprising an antigen binding domain of an antibody, wherein the antigen binding domain:

(i) specifically binds to IL-23 but does not significantly bind to an IL-12p40 subunit and does not significantly bind to an IL-23p19 subunit when they are not components of IL-23;

(ii) binds to IL-23 in which hydrogens therein have been exchanged with deuterium; and (iii) upon binding to IL-23 in which hydrogens therein have been exchanged with deuterium reduces exchange of the deuterium to hydrogen in a region comprising residues 112-144 of SEQ ID NO: 2.

In one example, the reduction in exchange is statistically significant.

In one example, the reduction in exchange is calculated by determining the percentage change in deuterium content of regions of IL-23 before and after exchange and identifying regions having a change greater than 2 or 2.5 or 3 standard deviations greater than the average change for regions having the lowest percentage change (e.g., 50% of the regions tested with the lowest percentage change).

In one example, the antigen binding domain reduces exchange in a region comprising residues 91-144 of SEQ ID NO: 2 or a region comprising comprising residues 91-109 and 112-144 of SEQ ID NO: 2.

In one example, the antigen binding domain additionally reduces exchange in a region comprising residues 135-153 of SEQ ID NO: 1. In accordance with this example, the present disclosure additionally or alternatively provides an isolated or recombinant IL-23-binding protein comprising an antigen binding domain of an antibody, wherein the antigen binding domain:
(i) specifically binds to IL-23 but does not significantly bind to an IL-12p40 subunit and does not significantly bind to an IL-23p19 subunit when they are not components of IL-23;
(ii) binds to IL-23 in which hydrogens therein have been exchanged with deuterium; and
(iii) upon binding to IL-23 in which hydrogens therein have been exchanged with deuterium reduces exchange of the deuterium to hydrogen in a region of the IL-12p40 subunit and in a region of the IL-23p19 subunit.

In one example, the IL-23-binding protein binds specifically to IL-23 but does not significantly bind to an isolated IL-12p40 subunit and does not significantly bind to an isolated IL-23p19 subunit.

In one example, the isolated IL-12p40 subunit comprises an additional sequence, e.g., FLAG tag or a Fc region of an antibody. For example, an IL-12p40 subunit comprises a sequence set forth in SEQ ID NO: 1 fused to a FLAG tag comprising a sequence set forth in SEQ ID NO: 17 or fused to a Fc region of an antibody, the Fc region comprising a sequence set forth in SEQ ID NO: 16.

In one example, the isolated IL-23p19 subunit comprises an additional sequence, e.g., a FLAG tag or a Fc region of an antibody. For example, an IL-23p19 subunit comprises a sequence set forth in SEQ ID NO: 2 fused to a FLAG tag comprising a sequence set forth in SEQ ID NO: 17 or fused to a Fc region of an antibody, the Fc region comprising a sequence set forth in SEQ ID NO: 16.

In one example, the IL-23-binding protein binds specifically to IL-23, wherein IL-12p40 and IL-23p19 subunits of IL-23 comprise an additional sequence, e.g., a FLAG tag or a Fc region of an antibody as described above.

In one example, an IL-23-binding protein of the present disclosure reduces binding of IL-23 to IL-23 receptor (IL-23R) with an $IC_{50}$ of 1 nM or less, such as 750 pM or less, for example 500 pM or less. In one example, the $IC_{50}$ of the IL-23-binding protein is 400 pM or less.

In one example, an IL-23-binding protein of the present disclosure reduces binding of IL-23 to IL-23R with an $IC_{50}$ of between 100 nM and 1 nM, such as between 150 pM and 750 pM, for example between 150 pM and 500 pM. In one example, the $IC_{50}$ of the IL-23-binding protein is between 160 pM and 400 pM.

In one example, an IL-23-binding protein of the present disclosure reduces binding of IL-23 to IL-23R with an $EC_{50}$ of 1 nM or less, for example, 750 pM or less, for example, 500 pM or less, such as 400 pM or less. In one example, the $EC_{50}$ is about 300 pM or less. For example, the $EC_{50}$ is about 260 pM.

Methods for determining binding of IL-23 to IL-23R will be apparent to the skilled artisan. For example, in one method isolated or recombinant IL-23R or a cell expressing IL-23R is immobilized. Labeled IL-23 is then contacted to the immobilized receptor or cell in the presence or absence of a test protein, which is suspect of reducing binding of IL-23 to IL-23R and the amount of bound label detected. A reduction in the amount of bound label in the presence of the IL-23-binding protein when compared to the absence of the protein indicates that the protein reduces or prevents binding of IL-23 to IL-23R. By testing multiple concentrations of the IL-23-binding protein an $IC_{50}$ and/or an $EC_{50}$ is determined.

In another example, an IL-23-binding protein of the disclosure reduces IL-23-induced IL-17 secretion by splenocytes. In one method, cultured splenocytes (such as mouse splenocytes) are contacted with IL-23 in the presence or absence of the IL-23-binding protein. Following sufficient time for IL-17 secretion to occur, IL-17 levels are detected, e.g., using an enzyme linked immunosorbent assay (ELISA). A lower level of the cytokine in the presence of the protein compared to in the absence of the protein indicates that the protein neutralizes IL-23 activity. By testing multiple concentrations of the protein an $IC_{50}$ and/or $EC_{50}$ is determined.

In one example, the $IC_{50}$ is 1 μM or less, for example, 800 μM or less, for example, 750 μM or less, such as 500 μM or less.

In one example, the $IC_{50}$ is about 1 nM or less, for example, 800 pM or less. For example, the $IC_{50}$ is 700 pM or less. In one example, the $IC_{50}$ is between about 1 pM and 800 pM, for example, between about 100 pM and 700 pM, for example, between about 120 pM and 680 pM.

In one example, the $EC_{50}$ is 1 μM or less, for example, 800 μM or less, for example, 750 μM or less, such as 500 μM or less.

In one example, the $EC_{50}$ is 1 nM or less, for example, 500 pM or less, such as 400 pM or less. In one example, the $EC_{50}$ is about 300 pM or less. For example, the $EC_{50}$ is about 290 pM.

In one example, the IL-23-binding protein is capable of specifically binding to IL-23 and competitively inhibiting the binding of an antibody to IL-23, wherein the antibody comprises any one of the following:
(i) a $V_H$ comprising a sequence set forth in SEQ ID NO: 7 and a $V_L$ comprising a sequence set forth in SEQ ID NO: 12; or
(ii) a $V_H$ comprising a sequence set forth in SEQ ID NO: 49 and a $V_L$ comprising a sequence set forth in SEQ ID NO: 50.

Methods for determining competitive inhibition of binding of an antibody to IL-23 are described herein and are to be taken to apply mutatis mutandis to this example of the disclosure.

For example, the IL-23-binding protein binds to an epitope that is the same as or overlaps with the epitope bound by an antibody comprising any one of the following:
(i) a $V_H$ comprising a sequence set forth in SEQ ID NO: 7 and a $V_L$ comprising a sequence set forth in SEQ ID NO: 12; or
(ii) a $V_H$ comprising a sequence set forth in SEQ ID NO: 49 and a $V_L$ comprising a sequence set forth in SEQ ID NO: 50.

In one example, the antigen binding domain of an IL-23-binding protein of the disclosure specifically binds to the IL-23p19 subunit of IL-23 when a component of IL-23. For example, the antigen binding domain specifically binds to the IL-23p19 subunit of IL-23 when a component of IL-23 in a region comprising amino acids 112-144 of SEQ ID NO: 2.

In one example, the antigen binding domain of an IL-23-binding protein of the disclosure specifically binds to both the IL-12p40 subunit and the IL-23p19 subunit when components of IL-23. For example, the antigen binding domain binds to regions of the IL-12p40 subunit and the IL-23p19 subunit comprising atoms within about 50 Angstroms of one another, such as 40 Angstroms of one another, for example, 30 Angstroms of one another. In one example, atoms within the regions are within about 25 Angstroms of one another. For example, the antigen binding domain binds to the IL-23p19 subunit in a region comprising amino acids 112-144 of SEQ ID NO: 2 and to the IL-12p40 subunit in a region comprising amino acids 135-153 of SEQ ID NO: 1.

In one example, an IL-23-binding protein of the disclosure binds to IL-23 with a dissociation constant (kd) of at least about $1\times10^{-2}$, such as, at least about $9\times10^{-3}$, for example, at least about $8\times10^{-3}$, for example, at least about $7\times10^{-3}$.

In one example, an IL-23-binding protein of the disclosure binds to IL-23 with an association constant (ka) of at least about $1\times10^4$, such as, at least about $5\times10^4$, for example, at least about $1\times10^5$.

In one example, an IL-23-binding protein of the disclosure binds to IL-23 with an equilibrium constant ($K_D$) of at least about $1\times10^{-7}$, for example, $5\times10^{-8}$, such as, at least about $1\times10^{-8}$. In one example, an IL-23-binding protein of the disclosure binds to IL-23 with an equlibbrium constant ($K_D$) of between about $1\times10^{-7}$ and about $1\times10^{-9}$, for example, between about $1\times10^{-7}$ and about $1\times10^{-9}$.

The present disclosure additionally or alternatively provides an isolated or recombinant IL-23-binding protein comprising an antigen binding domain of an antibody, which comprises an amino acid sequence set forth in any one of SEQ ID NOs: 21 to 50 or a sequence having at least about 80% identity thereto or an amino acid sequence encoded by a nucleic acid comprising a sequence set forth in any one of SEQ ID NOs: 57 to 77 or a sequence having at least about 80% identity thereto or a nucleic acid that hybridizes thereto under moderate to high stringency conditions.

The present disclosure also provides an isolated or recombinant protein IL-23-binding protein comprising an antigen binding domain of an antibody, which comprises an amino acid sequence set forth in any one of SEQ ID NOs: 26 to 29, 49, 50 or amino acids 1-120 of any one of SEQ ID NOs: 20 or 30 to 33, or amino acids 1-113 of SEQ ID NO: 45 or 46 or a sequence having at least about 80% identity thereto or an amino acid sequence encoded by a nucleic acid comprising a sequence set forth in any one of SEQ ID NOs: 6, 11, 57 to 60, 72, 73, 76 or 77 or a sequence having at least about 80% identity thereto or a nucleic acid that hybridizes under moderate to high stringency conditions.

In one example, the antigen binding domain of an IL-23-binding protein of the disclosure comprises a complementarity determining region (CDR) 3 of a variable region comprising a sequence set forth in any one of SEQ ID NOs: 7, 12, 26, 27, 28, 29, 49 or 50. Exemplary numbering schemes for determining CDRs are known in the art and any of those systems can be used to determine a CDR of an IL-23-binding protein of the present disclosure.

In one example, an IL-23-binding protein of the disclosure comprises a CDR3 defined according to the Kabat numbering system and comprising a sequence set forth in SEQ ID NO: 10, SEQ ID NO: 15, SEQ ID NO: 53 or SEQ ID NO: 56.

In one example, an IL-23-binding protein of the disclosure comprises a CDR3 defined according to the enhanced Chothia numbering system and comprising a sequence labeled as "CDR3" and shown in bold text in any one of FIG. 7A to 7F.

In some examples of the disclosure, the antigen binding domain is an antibody variable region comprising three CDRs of a variable region comprising an amino acid sequence set forth in any one of SEQ ID NOs: 26, 27, 28, 29, 49 or 50.

For example, the antigen binding domain is a $V_H$ comprising three CDRs of an amino acid sequence set forth in any one of SEQ ID NOs: 26, 27, 28, 29 or 49. In one example, the $V_H$ comprises three CDRs of a variable region comprising a sequence set forth in SEQ ID NO: 7. In one example, the $V_H$ comprises three CDRs of a variable region comprising a sequence set forth in SEQ ID NO: 33. In one example, the $V_H$ comprises three CDRs of a variable region comprising a sequence set forth in SEQ ID NO: 49. In one example, the CDRs are defined according to the Kabat numbering system. For example, the IL-23-binding protein comprises a $V_H$ including CDRs as follows:

(i) a CDR1 comprising an amino acid sequence set forth in SEQ ID NO: 8 or 51 (or a sequence labeled as CDR1 and that is underlined in FIG. 7A, 7B or 7E);

(ii) a CDR2 comprising an amino acid sequence set forth in any one of SEQ ID NOs: 9, 22, 24 or 52 (or a sequence labeled as CDR2 and that is underlined in FIG. 7A, 7B or 7E) optionally, wherein any one or more of the five C-terminal amino acids of the CDR2 amino acid sequence are substituted with any other naturally-occurring amino acid; and (iii) a CDR3 comprising an amino acid sequence set forth in SEQ ID NO: 10 or 53 (or a sequence labeled as CDR3 and that is underlined in FIG. 7A, 7B or 7E).

In a further example, the CDRs are defined according to the enhanced Chothia numbering system. For example, the $V_H$ includes CDRs as follows:

(i) a CDR1 comprising an amino acid sequence labeled as CDR1 and shown in bold text in FIG. 7A, 7B or 7E) or comprising an amino acid sequence set forth in SEQ ID NO: 23 or 25;

(ii) a CDR2 comprising an amino acid sequence labeled as CDR2 and shown in bold text in FIG. 7A, 7B or 7E); and (iii) a CDR3 comprising an amino acid sequence labeled as CDR3 and shown in bold text in FIG. 7A, 7B or 7E).

In another example, the antigen binding domain is a $V_L$ comprising three CDRs of an amino acid sequence set forth in any one of SEQ ID NOs: 27, 29 or 50. In one example, the $V_L$ comprises three CDRs of a variable region comprising a sequence set forth in SEQ ID NO: 12. In one example, the $V_L$ comprises three CDRs of a variable region comprising a sequence set forth in SEQ ID NO: 50.

In one example, the CDRs are defined according to the Kabat numbering system. For example, the IL-23-binding protein comprises a $V_L$ including CDRs as follows:

(i) a CDR1 comprising an amino acid sequence set forth in SEQ ID NO: 13 or 54 (or a sequence labeled as CDR1 and that is underlined in FIG. 7C, 7D or 7F);

(ii) a CDR2 comprising an amino acid sequence set forth SEQ ID NO: 14 or 55 (or a sequence labeled as CDR2 and that is underlined in FIG. 7C, 7D or 7F); and (iii) a CDR3 comprising an amino acid sequence set forth in SEQ ID NO: 15 or 56 (or a sequence labeled as CDR3 and that is underlined in FIG. 7C, 7D or 7F).

In a further example, the CDRs are defined according to the enhanced Chothia numbering system. For example, the $V_L$ includes CDRs as follows:

(i) a CDR1 comprising an amino acid sequence labeled as CDR1 and shown in bold text in FIG. 7C, 7D or 7F).

(ii) a CDR2 comprising an amino acid sequence labeled as CDR2 and shown in bold text in FIG. 7B); and (iii) a CDR3 comprising an amino acid sequence labeled as CDR3 and shown in bold text in FIG. 7B).

In one example, the antigen binding domain comprises a $V_H$ and a $V_L$, each comprising three CDRs, e.g., as described above.

In one example, the antigen binding domain comprises six CDRs of one of the following pairs of variable regions:
(i) a heavy chain variable region ($V_H$) comprising a sequence set forth in SEQ ID NO: 26 and a light chain variable region ($V_L$) comprising a sequence set forth in SEQ ID NO: 27;
(ii) a $V_H$ comprising a sequence set forth in SEQ ID NO: 28 and a $V_L$ comprising a sequence set forth in SEQ ID NO: 29; or
(iii) a $V_H$ comprising a sequence set forth in SEQ ID NO: 49 and a $V_L$ comprising a sequence set forth in SEQ ID NO: 50.

For example, the antigen binding domain comprises:
(i) a heavy chain CDR1 comprising a sequence set forth in any one of SEQ ID NOs: 8 or 51 (or a sequence labeled as CDR1 and that is underlined in FIG. 7A, 7B or 7E);
(ii) a heavy chain CDR2 comprising a sequence set forth in any one of SEQ ID NOs: 9, 22 or 52 (or a sequence labeled as CDR2 and that is underlined in FIG. 7A, 7B or 7E) optionally, wherein any one or more of the five C-terminal amino acids of the CDR2 amino acid sequence are substituted with any other naturally-occurring amino acid;
(iii) a heavy chain CDR3 comprising a sequence set forth in any one of SEQ ID NOs: 10 or 53 (or a sequence labeled as CDR3 and that is underlined in FIG. 7A, 7B or 7E);
(iv) a light chain CDR1 comprising a sequence set forth in any one of SEQ ID NOs: 13 or 54 (or a sequence labeled as CDR1 and that is underlined in FIG. 7C, 7D or 7F);
(v) a light chain CDR2 comprising a sequence set forth in any one of SEQ ID NOs: 14 or 55 (or a sequence labeled as CDR2 and that is underlined in FIG. 7C, 7D or 7F); and
(vi) and a light chain CDR3 comprising a sequence set forth in any one of SEQ ID NOs: 15 or 56 (or a sequence labeled as CDR3 and that is underlined in FIG. 7C, 7D or 7F).

Exemplary IL-23-binding proteins of the disclosure comprise an antigen binding domain comprising a $V_H$ comprising an amino acid sequence set forth in any one of SEQ ID NOs: 26, 28 or 49. For example, the $V_H$ comprises an amino acid sequence set forth in any one of SEQ ID NO: 7, SEQ ID NO: 49 or amino acids 1-120 of any one of SEQ ID NOs: 30 to 44, or a sequence having at least about 80% identity to any one of the foregoing. In one example, the $V_H$ comprises an amino acid sequence set forth in any one of SEQ ID NO: 7, SEQ ID NO: 49 or amino acids 1-120 of any one of SEQ ID NOs: 30 to 33.

In another example, the $V_H$ comprises an amino acid sequence encoded by a nucleic acid comprising a sequence set forth in any one of SEQ ID NOs: 6, 19, 57 to 71, 76 or a sequence at least about 80% identical thereto or a nucleic acid that hybridizes thereto under moderate to high hybridization conditions. In one example, the $V_H$ comprises an amino acid sequence encoded by a nucleic acid comprising a sequence set forth in any one of SEQ ID NOs: 6, 19, 57 to 60, 76 or a sequence at least about 80% identical thereto or a nucleic acid that hybridizes thereto under moderate to high hybridization conditions.

In one example, the $V_H$ comprises a sequence set forth in SEQ ID NO: 28. In one example, the $V_H$ comprises a sequence set forth in amino acids 1-120 of SEQ ID NO: 30. In one example, the $V_H$ comprises a sequence set forth in amino acids 1-120 of SEQ ID NO: 31. In one example, the $V_H$ comprises a sequence set forth in amino acids 1-120 of SEQ ID NO: 32. In one example, the $V_H$ comprises a sequence set forth in amino acids 1-120 of SEQ ID NO: 33.

In one example, the $V_H$ comprises a sequence set forth in SEQ ID NO: 49.

In one example, the $V_H$ comprises a sequence set forth in SEQ ID NO: 7 or a humanized, deimmunized or synhumanized form thereof.

Exemplary IL-23-binding proteins of the disclosure comprise an antigen binding domain comprising a $V_L$ comprising an amino acid sequence set forth in any one of SEQ ID NOs: 27, 29 or 50. For example, the $V_L$ comprises an amino acid sequence set for in any one of SEQ ID NO: 12, SEQ ID NO: 50 or amino acids 1-113 of any one of SEQ ID NOs: 45 to 48 or a sequence having at least about 80% identity to any one of the foregoing. For example, the $V_L$ comprises an amino acid sequence set for in any one of SEQ ID NO: 12, SEQ ID NO: 50 or amino acids 1-113 of SEQ ID NO: 45 or 46 or a sequence having at least about 80% identity to any one of the foregoing.

In another example, the $V_L$ comprises an amino acid sequence encoded by a nucleic acid comprising a sequence set forth in any one of SEQ ID NO: 11, 18, 72 to 75 or 77 or a sequence at least about 80% identical thereto or a nucleic acid that hybridizes thereto under moderate to high hybridization conditions. For example, the $V_L$ comprises an amino acid sequence encoded by a nucleic acid comprising a sequence set forth in any one of SEQ ID NO: 11, 18, 72, 73 or 77 or a sequence at least about 80% identical thereto or a nucleic acid that hybridizes thereto under moderate to high hybridization conditions.

In one example, the $V_L$ comprises a sequence set forth in SEQ ID NO: 29. For example, the $V_L$ comprises a sequence set forth in SEQ ID NO: 45. For example, the $V_L$ comprises a sequence set forth in SEQ ID NO: 46.

In one example, the $V_L$ comprises a sequence set forth in SEQ ID NO: 50.

In one example, the $V_L$ comprises a sequence set forth in SEQ ID NO: 11 or a humanized, deimmunized or synhumanized form thereof.

Exemplary IL-23-binding proteins comprise a $V_H$ and a $V_L$, wherein the $V_{14}$ and $V_L$ bind to form a Fv comprising the antigen binding domain.

Exemplary IL-23-binding proteins comprise:
(i) a $V_H$ comprising CDRs 1, 2 and 3 of a variable region comprising a sequence set forth in SEQ ID NO: 26 and a $V_L$ comprising CDRs 1, 2 and 3 of a variable region comprising a sequence set forth in SEQ ID NO: 27;
(ii) a $V_H$ comprising CDRs 1, 2 and 3 of a variable region comprising a sequence set forth in SEQ ID NO: 28 and a $V_L$ comprising CDRs 1, 2 and 3 of a variable region comprising a sequence set forth in SEQ ID NO: 29; or
(iii) a $V_H$ comprising CDRs 1, 2 and 3 of a variable region comprising a sequence set forth in SEQ ID NO: 49 and a $V_L$ comprising CDRs 1, 2 and 3 of a variable region comprising a sequence set forth in SEQ ID NO: 50.

CDRs in these sequences defined according to the Kabat numbering system or the enhanced Chothia numbering system are described herein and are to be taken to apply mutatis mutandis to the present example of the disclosure.

In one exemplary form of the disclosure an IL-23-binding protein comprises:
(i) a $V_H$ comprising a CDR1 having a sequence set forth in SEQ ID NO: 8, a CDR2 having a sequence set forth in SEQ ID NO: 9 or 22 and a CDR3 having a sequence set forth in SEQ ID NO: 10; and
(ii) a $V_L$ comprising a CDR1 having a sequence set forth in SEQ ID NO: 13, a CDR2 having a sequence set forth in SEQ ID NO: 14 and a CDR3 having a sequence set forth in SEQ ID NO 15.

In another exemplary form of the disclosure an IL-23-binding protein comprises:
(i) a $V_H$ comprising a CDR1 having a sequence set forth in SEQ ID NO: 51, a CDR2 having a sequence set forth in SEQ ID NO: 52 and a CDR3 having a sequence set forth in SEQ ID NO: 53; and
(ii) a $V_L$ comprising a CDR1 having a sequence set forth in SEQ ID NO: 54, a CDR2 having a sequence set forth in SEQ ID NO: 55 and a CDR3 having a sequence set forth in SEQ ID NO 56.

In some IL-23-binding proteins the $V_H$ and the $V_L$ are in a single polypeptide chain. Exemplary forms of such IL-23-binding proteins include:
(i) a single chain Fv fragment (scFv);
(ii) a dimeric scFv (di-scFv); or
(iii) at least one of (i) and/or (ii) linked to a constant region, a Fc or a heavy chain constant domain ($C_H$) 2 and/or $C_H$3.

Other exemplary IL-23-binding proteins comprise the $V_L$ and $V_H$ in separate polypeptide chains. Exemplary forms of such IL-23-binding proteins include:
(i) a diabody;
(ii) a triabody;
(iii) a tetrabody;
(iv) a Fab;
(v) a F(ab')$_2$;
(vi) a Fv; or
(iv) one of (i) to (iii) linked to a constant region, a Fc or a heavy chain constant domain ($C_H$) 2 and/or $C_H$3.

An example of an IL-23-binding protein of the disclosure is an antibody.

Some exemplary IL-23-binding proteins of the disclosure are chimeric, de-immunized, humanized, primatized, synhumanized or human.

In one example, the present disclosure provides an antibody comprising an antigen binding domain, wherein the antigen binding domain specifically binds to IL-23 but does not significantly bind to an IL-12p40 subunit and does not significantly bind to an IL-23p19 subunit when they are not components of IL-23, the antigen binding domain comprising a $V_H$ comprising a sequence set forth in SEQ ID NO: 26, 28 or 49 and/or a $V_L$ comprising a sequence set forth in any one of SEQ ID NOs: 27, 29 or 50. For example, the antibody comprises:
(i) a $V_H$ comprising a sequence set forth in any one of SEQ ID NO: 7, SEQ ID NO: 49 or amino acids 1-120 of any one of SEQ ID NOs: 30 to 44 or a sequence having at least about 80% identity to any one of the foregoing; and/or
(ii) a $V_L$ comprising an amino acid sequence set for in any one of SEQ ID NO: 12, SEQ ID NO: 50 or amino acids 1-113 of any one of SEQ ID NOs: 45 to 48. or a sequence having at least about 80% identity to any one of the foregoing.

In one example, the present disclosure provides an antibody comprising an antigen binding domain, wherein the antigen binding domain specifically binds to IL-23 but does not significantly bind to an IL-12p40 subunit and does not significantly bind to an IL-23p19 subunit when they are not components of IL-23, the antigen binding domain comprising:
(i) a $V_H$ comprising a sequence set forth in SEQ ID NO: 26 and a $V_L$ comprising a sequence set forth in SEQ ID NO: 27;
(ii) a $V_H$ comprising a sequence set forth in SEQ ID NO: 28 and a $V_L$ comprising a sequence set forth in SEQ ID NO: 29; or
(iii) a $V_H$ comprising a sequence set forth in SEQ ID NO: 49 and a $V_L$ comprising a sequence set forth in SEQ ID NO: 50.

In one example, the present disclosure provides a humanized antibody comprising an antigen binding domain, wherein the antigen binding domain specifically binds to IL-23 but does not significantly bind to an IL-12p40 subunit and does not significantly bind to an IL-23p19 subunit when they are not components of IL-23, the antigen binding domain comprising a $V_H$ comprising a sequence set forth in SEQ ID NO: 28 and a $V_L$ comprising a sequence set forth in SEQ ID NO: 29.

In one example, the antigen binding domain of the humanized antibody comprises:
(i) a $V_H$ comprising a sequence set forth in amino acids 1-120 of SEQ ID NO: 30 and a $V_L$ comprising a sequence set forth in amino acids 1-113 of SEQ ID NO: 45;
(ii) a $V_H$ comprising a sequence set forth in amino acids 1-120 of SEQ ID NO: 31 and a $V_L$ comprising a sequence set forth in amino acids 1-113 of SEQ ID NO: 45;
(iii) a $V_H$ comprising a sequence set forth in amino acids 1-120 of SEQ ID NO: 32 and a $V_L$ comprising a sequence set forth in amino acids 1-113 of SEQ ID NO: 46;
(iv) a $V_H$ comprising a sequence set forth in amino acids 1-120 of SEQ ID NO: 33 and a $V_L$ comprising a sequence set forth in amino acids 1-113 of SEQ ID NO: 46;
(v) a $V_H$ comprising a sequence set forth in amino acids 1-120 of SEQ ID NO: 34 and a $V_L$ comprising a sequence set forth in amino acids 1-113 of SEQ ID NO: 46;
(vi) a $V_H$ comprising a sequence set forth in amino acids 1-120 of SEQ ID NO: 35 and a $V_L$ comprising a sequence set forth in amino acids 1-113 of SEQ ID NO: 47;
(vii) a $V_H$ comprising a sequence set forth in amino acids 1-120 of SEQ ID NO: 33 and a $V_L$ comprising a sequence set forth in amino acids 1-113 of SEQ ID NO: 48;
(viii) a $V_H$ comprising a sequence set forth in amino acids 1-120 of SEQ ID NO: 34 and a $V_L$ comprising a sequence set forth in amino acids 1-113 of SEQ ID NO: 48;
(ix) a $V_H$ comprising a sequence set forth in amino acids 1-120 of SEQ ID NO: 32 and a $V_L$ comprising a sequence set forth in amino acids 1-113 of SEQ ID NO: 48;
(x) a $V_H$ comprising a sequence set forth in amino acids 1-120 of SEQ ID NO: 36 and a $V_L$ comprising a sequence set forth in amino acids 1-113 of SEQ ID NO: 45;
(xi) a $V_H$ comprising a sequence set forth in amino acids 1-120 of SEQ ID NO: 37 and a $V_L$ comprising a sequence set forth in amino acids 1-113 of SEQ ID NO: 47;
(xii) a $V_H$ comprising a sequence set forth in amino acids 1-120 of SEQ ID NO: 38 and a $V_L$ comprising a sequence set forth in amino acids 1-113 of SEQ ID NO: 46;
(xiii) a $V_H$ comprising a sequence set forth in amino acids 1-120 of SEQ ID NO: 39 and a $V_L$ comprising a sequence set forth in amino acids 1-113 of SEQ ID NO: 46;
(xiv) a $V_H$ comprising a sequence set forth in amino acids 1-120 of SEQ ID NO: 40 and a $V_L$ comprising a sequence set forth in amino acids 1-113 of SEQ ID NO: 45;
(xv) a $V_H$ comprising a sequence set forth in amino acids 1-120 of SEQ ID NO: 41 and a $V_L$ comprising a sequence set forth in amino acids 1-113 of SEQ ID NO: 46;
(xvi) a $V_H$ comprising a sequence set forth in amino acids 1-120 of SEQ ID NO: 42 and a $V_L$ comprising a sequence set forth in amino acids 1-113 of SEQ ID NO: 46;
(xvii) a $V_H$ comprising a sequence set forth in amino acids 1-120 of SEQ ID NO: 43 and a $V_L$ comprising a sequence set forth in amino acids 1-113 of SEQ ID NO: 47;
(xviii) a $V_H$ comprising a sequence set forth in amino acids 1-120 of SEQ ID NO: 38 and a $V_L$ comprising a sequence set forth in amino acids 1-113 of SEQ ID NO: 48;

(xix) a $V_H$ comprising a sequence set forth in amino acids 1-120 of SEQ ID NO: 39 and a $V_L$ comprising a sequence set forth in amino acids 1-113 of SEQ ID NO: 48;

(xx) a $V_H$ comprising a sequence set forth in amino acids 1-120 of SEQ ID NO: 44 and a $V_L$ comprising a sequence set forth in amino acids 1-113 of SEQ ID NO: 47;

(xxi) a $V_H$ comprising a sequence set forth in amino acids 1-120 of SEQ ID NO: 41 and a $V_L$ comprising a sequence set forth in amino acids 1-113 of SEQ ID NO: 48; or (xxii) a $V_H$ comprising a sequence set forth in amino acids 1-120 of SEQ ID NO: 42 and a $V_L$ comprising a sequence set forth in amino acids 1-113 of SEQ ID NO: 48.

In one example, the present disclosure provides a humanized antibody comprising an antigen binding domain, wherein the antigen binding domain specifically binds to IL-23 but does not significantly bind to an IL-12p40 subunit and does not significantly bind to an IL-23p19 subunit when they are not components of IL-23, the antigen binding domain comprising:

(i) a $V_H$ comprising a sequence set forth in amino acids 1-120 of SEQ ID NO: 30 and a $V_L$ comprising a sequence set forth in amino acids 1-113 of SEQ ID NO: 45;

(ii) a $V_H$ comprising a sequence set forth in amino acids 1-120 of SEQ ID NO: 31 and a $V_L$ comprising a sequence set forth in amino acids 1-113 of SEQ ID NO: 45;

(iii) a $V_H$ comprising a sequence set forth in amino acids 1-120 of SEQ ID NO: 32 and a $V_L$ comprising a sequence set forth in amino acids 1-113 of SEQ ID NO: 46; or (iv) a $V_H$ comprising a sequence set forth in amino acids 1-120 of SEQ ID NO: 33 and a $V_L$ comprising a sequence set forth in amino acids 1-113 of SEQ ID NO: 46.

The present disclosure also provides a human antibody comprising an antigen binding domain of an antibody, wherein the antigen binding domain specifically binds to IL-23 but does not significantly bind to an IL-12p40 subunit and does not significantly bind to an IL-23p19 subunit when they are not components of IL-23, the antibody antigen binding domain comprising a heavy chain variable region ($V_H$) comprising a sequence set forth in SEQ ID NO: 49 and a light chain variable region ($V_L$) comprising a sequence set forth in SEQ ID NO: 50.

An exemplary form of an IL-23-binding protein of the disclosure is a chimeric antibody comprising a $V_H$ comprising a sequence set forth in SEQ ID NO: 7 linked to a constant region comprising a sequence set forth in SEQ ID NO: 3 or 16 and a $V_L$ comprising a sequence set forth in SEQ ID NO: 12 linked to a constant region comprising a sequence set forth in SEQ ID NO: 4. In one example, the chimeric antibody comprises a heavy chain comprising a sequence set forth in SEQ ID NO: 20 and a light chain comprising a sequence set forth in SEQ ID NO: 21.

The present disclosure additionally provides a monoclonal antibody comprising an antigen binding domain, wherein the antigen binding domain specifically binds to IL-23 but does not significantly bind to an IL-12p40 subunit and does not significantly bind to an IL-23p19 subunit when they are not components of IL-23, the antibody antigen binding domain comprising a $V_H$ comprising a sequence set forth in SEQ ID NO: 7 and a $V_L$ comprising a sequence set forth in SEQ ID NO: 12 or a chimeric, de-immunized, synhumanized or humanized form of the monoclonal antibody.

In one example, an IL-23-binding protein of the disclosure comprises a human or non-human primate heavy chain immunoglobulin constant region selected from a group consisting of IgG1, IgG2, IgG3, IgG4, IgM, IgD, IgE and IgA. An exemplary heavy chain immunoglobulin constant region is an IgG constant region, e.g., an IgG1 constant region. In one example, a constant region comprises a sequence set forth in SEQ ID NO: 3 or 16.

In another example, an IL-23-binding protein of the disclosure comprises a human or non-human primate light chain immunoglobulin constant region selected from a group consisting of kappa or lambda. In one example a kappa light chain constant region comprises a sequence set forth in SEQ ID NO: 4. In one example a lambda light chain constant region comprises a sequence set forth in SEQ ID NO:83.

In one example, the IL-23-binding protein neutralizes IL-23 activity.

In an example, the IL-23-binding protein is conjugated to a compound selected from the group consisting of a radioisotope, a detectable label, a therapeutic compound, a colloid, a toxin, a nucleic acid, a peptide, a protein, a compound that increases the half life of the protein in a subject and mixtures thereof.

The present disclosure also provides a nucleic acid encoding the IL-23-binding protein of the present disclosure. In this regard, the disclosure is not limited to the specific exemplified nucleic acids described herein, but also encompasses any nucleic acid that encodes an IL-23-binding protein of the disclosure as a result of degeneracy of the genetic code. For example, the nucleic acid may be codon optimized for expression in a particular cell type.

In one example, the nucleic acid comprises a sequence set forth in any one of SEQ ID NOs: 6, 11, 18, 19 or 57 to 77 or a sequence having at least about 80% identity thereto or a sequence that hybridizes thereto under moderate or high stringency conditions. In one example, the nucleic acid comprises a sequence set forth in any one of SEQ ID NOs: 6, 11, 18, 19, 57 to 60, 72, 73, 76 or 77 or a sequence having at least about 80% identity thereto or a sequence that hybridizes thereto under moderate or high stringency conditions.

In one example, such a nucleic acid is included in an expression construct in which the nucleic acid is operably linked to a promoter. Such an expression construct can be in a vector, e.g., a plasmid.

In examples of the disclosure directed to single polypeptide IL-23-binding proteins, the expression construct may comprise a promoter linked to a nucleic acid encoding that polypeptide chain.

In examples directed to multiple polypeptides that form an IL-23-binding protein, an expression construct of the disclosure comprises a nucleic acid encoding one of the polypeptides (e.g., comprising a $V_H$) operably linked to a promoter and a nucleic acid encoding another of the polypeptides (e.g., comprising a $V_L$) operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide.

For example, the first polypeptide comprises a $V_H$ and the second polypeptide comprises a $V_L$, or the first polypeptide comprises a $V_L$ and the second polypeptide comprises a $V_H$.

The present disclosure also contemplates separate expression constructs one of which encodes a first polypeptide (e.g., comprising a $V_H$) and another of which encodes a second polypeptide (e.g., comprising a $V_L$). For example, the present disclosure also provides a composition comprising:
(i) a first expression construct comprising a nucleic acid encoding a polypeptide (e.g., comprising a $V_H$ operably linked to a promoter); and (ii) a second expression construct comprising a nucleic acid encoding a polypeptide (e.g., comprising a $V_L$ operably linked to a promoter), wherein the first and second polypeptides associate to form an IL-23-binding protein of the present disclosure.

The present disclosure also provides an isolated cell expressing an IL-23-binding protein of the disclosure or a recombinant cell genetically-modified to express an IL-23-binding protein of the disclosure.

In one example, the cell comprises the expression construct of the disclosure or:
(i) a first expression construct comprising a nucleic acid encoding a polypeptide (e.g., comprising a $V_H$) operably linked to a promoter; and
(ii) a second expression construct comprising a nucleic acid encoding a polypeptide (e.g., comprising a $V_L$) operably linked to a promoter, wherein the first and second polypeptides associate to form an IL-23-binding protein of the present disclosure.

Examples of cells of the present disclosure include bacterial cells, yeast cells, insect cells or mammalian cells.

The present disclosure additionally provides methods for producing an IL-23-binding protein of the disclosure. For example, such a method involves maintaining the expression construct(s) of the disclosure under conditions sufficient for the IL-23-binding protein to be produced.

In one example, a method for producing an IL-23-binding protein of the disclosure comprises culturing the cell of the disclosure under conditions sufficient for the IL-23-binding protein to be produced and, optionally, secreted.

In one example, the method for producing an IL-23-binding protein of the disclosure additionally comprises isolating the IL-23-binding protein.

The present disclosure also provides a composition comprising an IL-23-binding protein of the disclosure and a suitable carrier or diluent. In one example, the carrier or diluent is pharmaceutically acceptable.

The present disclosure additionally provides a method for treating or preventing symptoms of an IL-23-mediated condition in a cell, tissue, organ or subject, the method comprising administering an IL-23-binding protein of the disclosure or nucleic acid encoding same or cell expressing same or a composition of the disclosure to the cell, tissue, organ or subject.

The present disclosure also provides for use of an IL-23-binding protein of the disclosure or a composition of the disclosure in medicine.

The present disclosure additionally or alternatively provides for use of an IL-23-binding protein of the disclosure in the manufacture of a medicament for the treatment of n IL-23-mediated condition.

In one example, the condition is a $T_H17$ cell-mediated condition. In one example, the condition is an inflammatory condition or an autoimmune condition.

For example, the condition is psoriasis, Crohn's disease or multiple sclerosis. In one exemplary form, the condition is psoriasis.

The present disclosure also provides an IL-23-binding protein, antibody, composition of the disclosure for use in the treatment of psoriasis or Crohn's disease or multiple sclerosis.

The present disclosure additionally provides a method for detecting IL-23 in a sample, the method comprising contacting a sample with an IL-23-binding protein of the disclosure such that an antigen-protein complex forms and detecting the complex, wherein detecting the complex is indicative of IL-23 in the sample.

In one example, the method comprises contacting a sample with an IL-23-binding protein of the present disclosure, which is immobilized on a solid or semi-solid substrate such that a protein-antigen complex forms and detecting the complex. In some examples, detecting the complex comprises contacting the complex with a second protein comprising an antigen binding domain of an antibody that binds to IL-23 and/or IL-23p19 and/or IL-12p40 at a distinct site from an IL-23-binding protein of the disclosure and detecting the second protein.

For example, the second protein is labeled with a detectable label. Alternatively, a further labeled protein is used that binds to the second protein.

In another example, the method comprises
(i) contacting a sample with a protein comprising an antigen binding domain of an antibody that binds to IL-23 and/or IL-23p19 and/or IL-12p40 at a distinct site from an IL-23-binding protein of the disclosure, which is immobilized on a solid or semi-solid substrate such that a protein-antigen complex forms; and
(ii) detecting the complex by contacting the complex with an IL-23-binding protein of the disclosure and detecting the IL-23-binding protein of the disclosure.

For example, the IL-23-binding protein of the disclosure is labeled with a detectable label. Alternatively, a further labeled protein is used that binds to the IL-23-binding protein of the disclosure.

The present disclosure also provides a method for diagnosing or prognosing a condition in a subject, the method comprising performing a method of the disclosure to detect IL-23 in a sample from the subject, wherein detection of IL-23 in the sample is indicative of the condition.

In one example, the method comprises determining the level of IL-23 in the sample, wherein an increased or decreased level of IL-23 in the sample compared to a control sample is indicative of the condition.

Exemplary conditions are described herein and are to be taken to apply mutatis mutandis to the present example of the disclosure.

The ability to specifically bind to IL-23 also permits imaging applications, e.g., to diagnose or prognose conditions. Accordingly, present disclosure additionally provides a method for localizing and/or detecting IL-23 in a subject, the method comprising detecting in vivo the IL-23-binding protein or antibody of the disclosure bound to IL-23, if present, wherein the IL-23-binding protein or antibody is conjugated to a detectable label. In one example, the method additionally comprises administering the IL-23-binding protein or antibody to the subject.

The value (25.867 is the distance in Angstroms between some atoms of the regions in IL-23p19 and IL-12p40)

Figure 3:
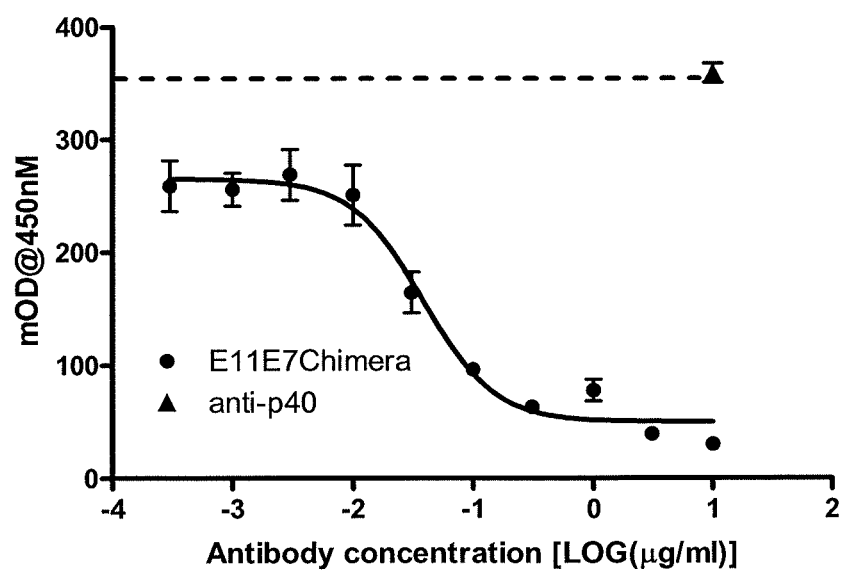

FIG. 3 is a graphical representation showing inhibition of binding of IL-23 to IL-23 receptor (IL-23R) by E11E7Chimera or an anti-IL-12-p40 antibody, as indicated.

Figure 4:
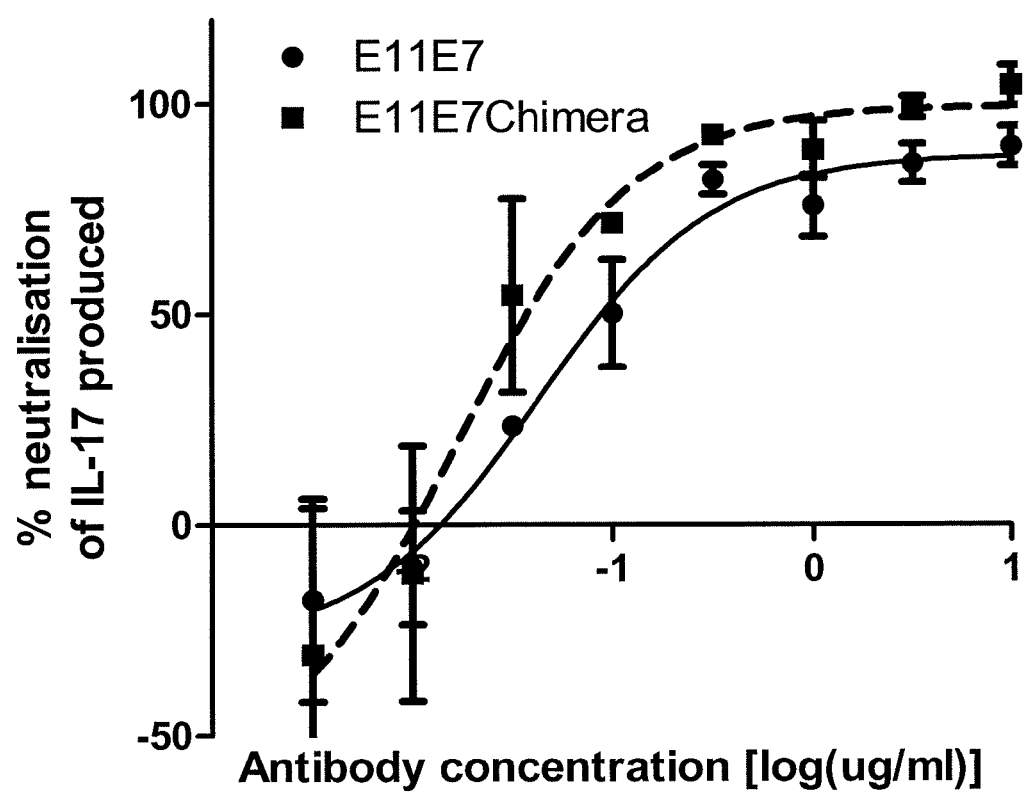

FIG. 4 is a graphical representation showing E11E7 or E11E7Chimera-mediated neutralization of IL-23-induced IL-17 secretion by mouse splenocytes. Values are expressed as percentage inhibition compared to IL-23-induced IL-17 secretion by mouse splenocytes in the absence of antibody.

Figure 5A:
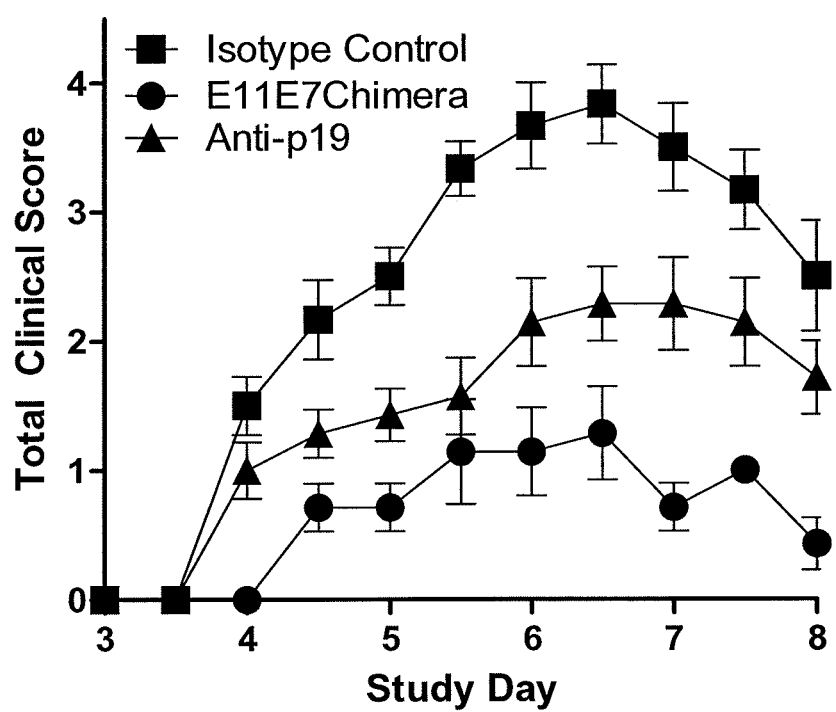

FIG. 5A is a graphical representation showing clinical score over time in an IL-23-mediated mouse model of psoriasis in animals treated with E11 E7Chimera, an anti-IL-23p19 antibody or an isotype control antibody (as indicated).

Figure 5B:
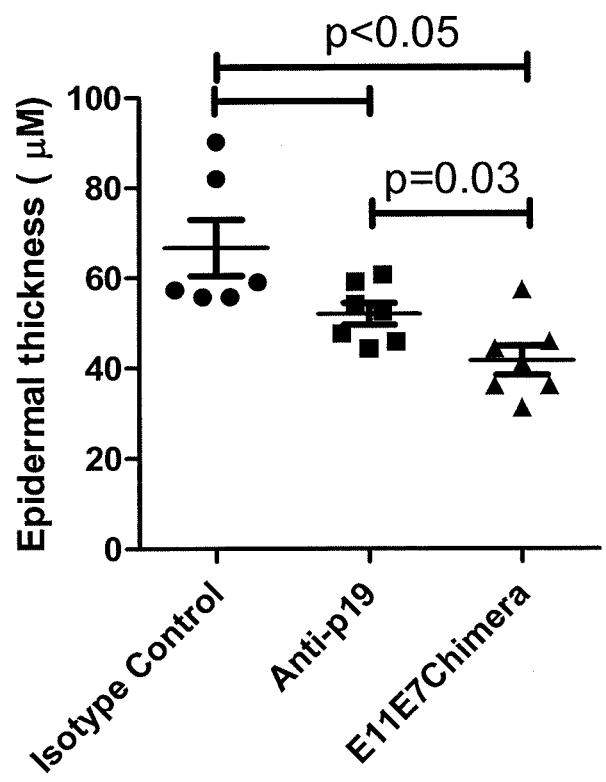

FIG. 5B is a graphical representation showing epidermal thickness in an IL-23-mediated mouse model of psoriasis in animals treated with E11 E7Chimera, an anti-IL-23p19 antibody or an isotype control antibody (as indicated).

Figure 6A:
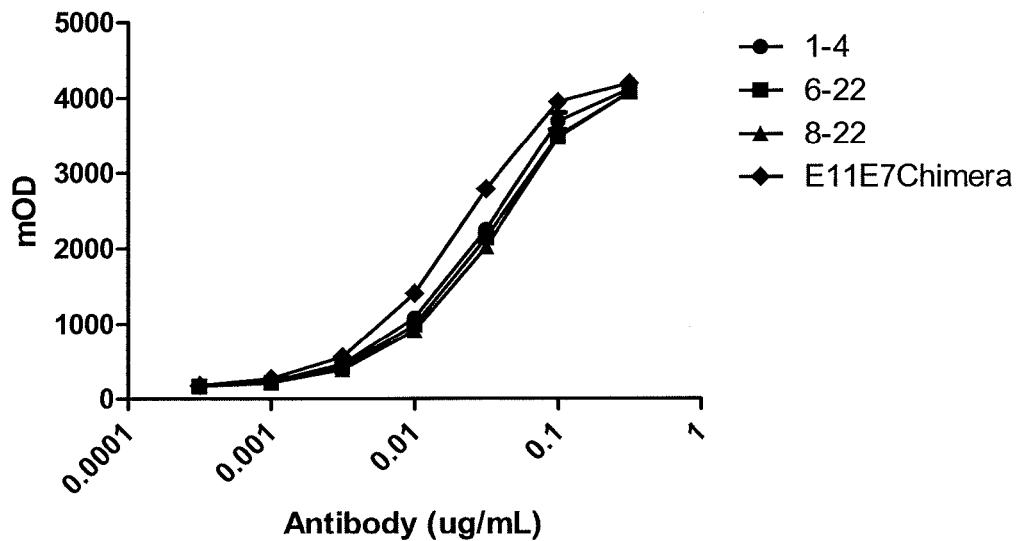
Figure 6B:
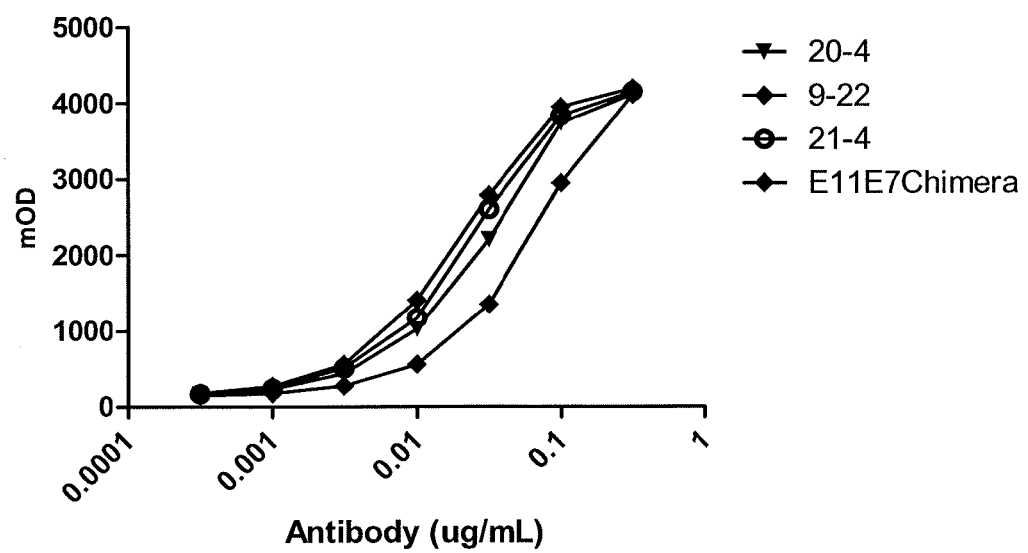

FIGS. 6A and 6B are graphical representations showing binding of E11 E7Chimera and humanized forms of E11E7 to IL-23 as determined using ELISA.

FIGS. 7A to 7F are diagrammatic representations showing sequences and/or alignments of sequences of variable regions of antibodies. FIG. 7A shows an alignment of $V_H$ regions of E11E7 and humanized forms thereof. FIG. 7B shows alignments of $V_H$ regions of selected humanized forms of E11E7. FIG. 7C shows an alignment of $V_L$ regions of E11E7 and humanized forms thereof. FIG. 7D shows alignments of $V_L$ regions of selected humanized forms of E11E7. FIG. 7E shows the amino acid sequence of the $V_H$ of human antibody ST883/885. FIG. 7F shows the amino acid sequence of the $V_L$ of human antibody ST883/885. The symbols beneath the alignments are: "*", meaning the residues in the alignment are identical; ":" meaning that the residues in the alignment are strongly conserved (strongly conserved groups, STA; NEQK; NHQK; NDEQ; QHRK; MILV; MILF; HY; FYW), and "." meaning the residues are weakly conserved (weakly conserved groups, CSA; ATV; SAG; STNK; STPA; SGND; SNDEQK; NDEQHK; NEQHRK; FVLIM; HFY). A consensus sequence is also shown in which is "X" indicates a site of variation. Beneath the "X" is indicated all amino acids that occur at that site in the analyzed sequences. Boxed regions contain CDRs (as indicated) as defined by the Kabat numbering system and the enhanced Chothia numbering system. CDRs defined by the Kabat numbering system are underlined. CDRs defined by the enhanced Chothia numbering system are shown in bold.

Figure 8:
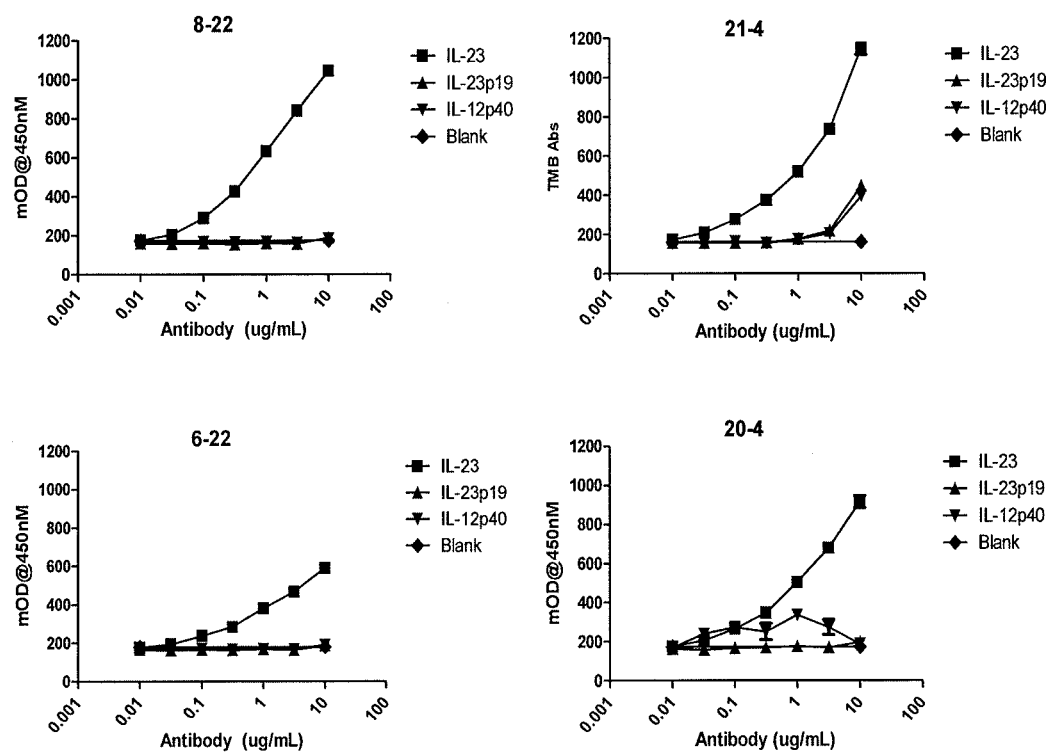

FIG. 8 includes a series of graphical representations showing binding of humanized forms of E11E7 to IL-23 but not significantly binding to IL-12p40 or IL-23p19. Blank refers to assay conditions in which the coating antigen is omitted.

Figure 9:
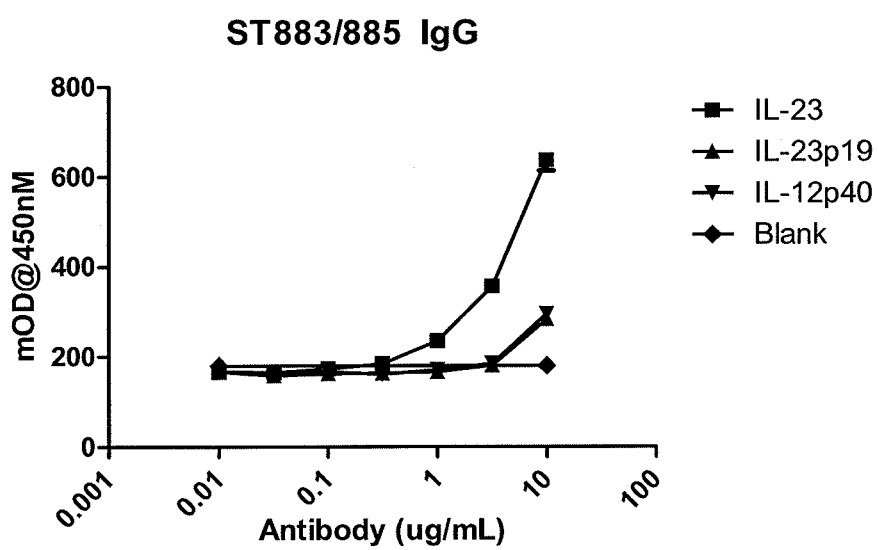

FIG. 9 is a graphical representations showing binding of fully human antibody ST883/885IgG to IL-23 but not significantly binding to IL-12p40 or IL-23p19. Blank refers to assay conditions in which the coating antigen is omitted.

Figure 10A:
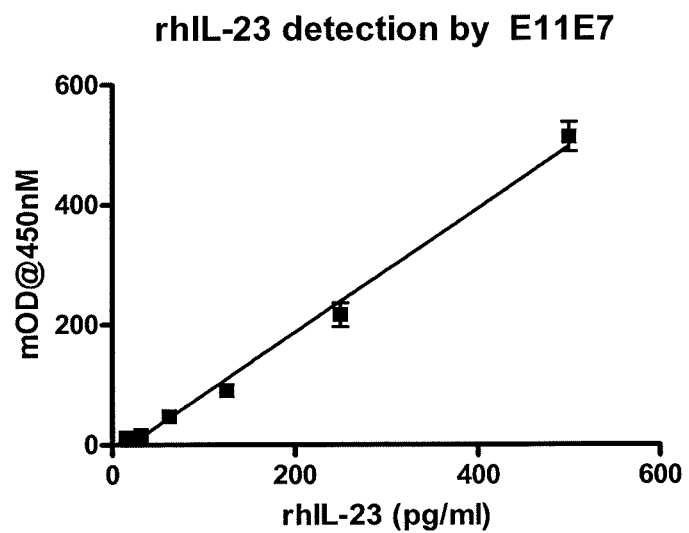
Figure 10B:
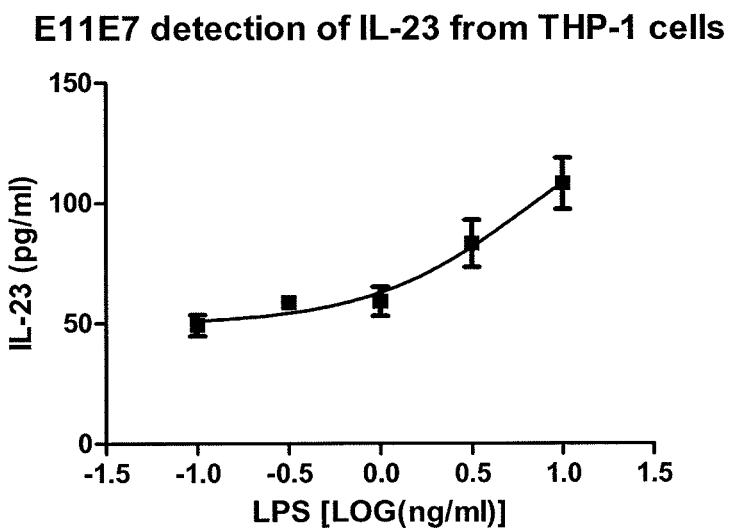

FIGS. 10A and 10B are graphical representations showing detection of recombinant IL-23 using E11E7 as a capture antibody as performed via ELISA (A) and the detection of native IL-23, by E11E7, produced by the cell line THP-1 when stimulated with Pokeweed Mitogen (PWM) and lipopolysaccharide (LPS), as measured by ELISA (B).

Figure 11:
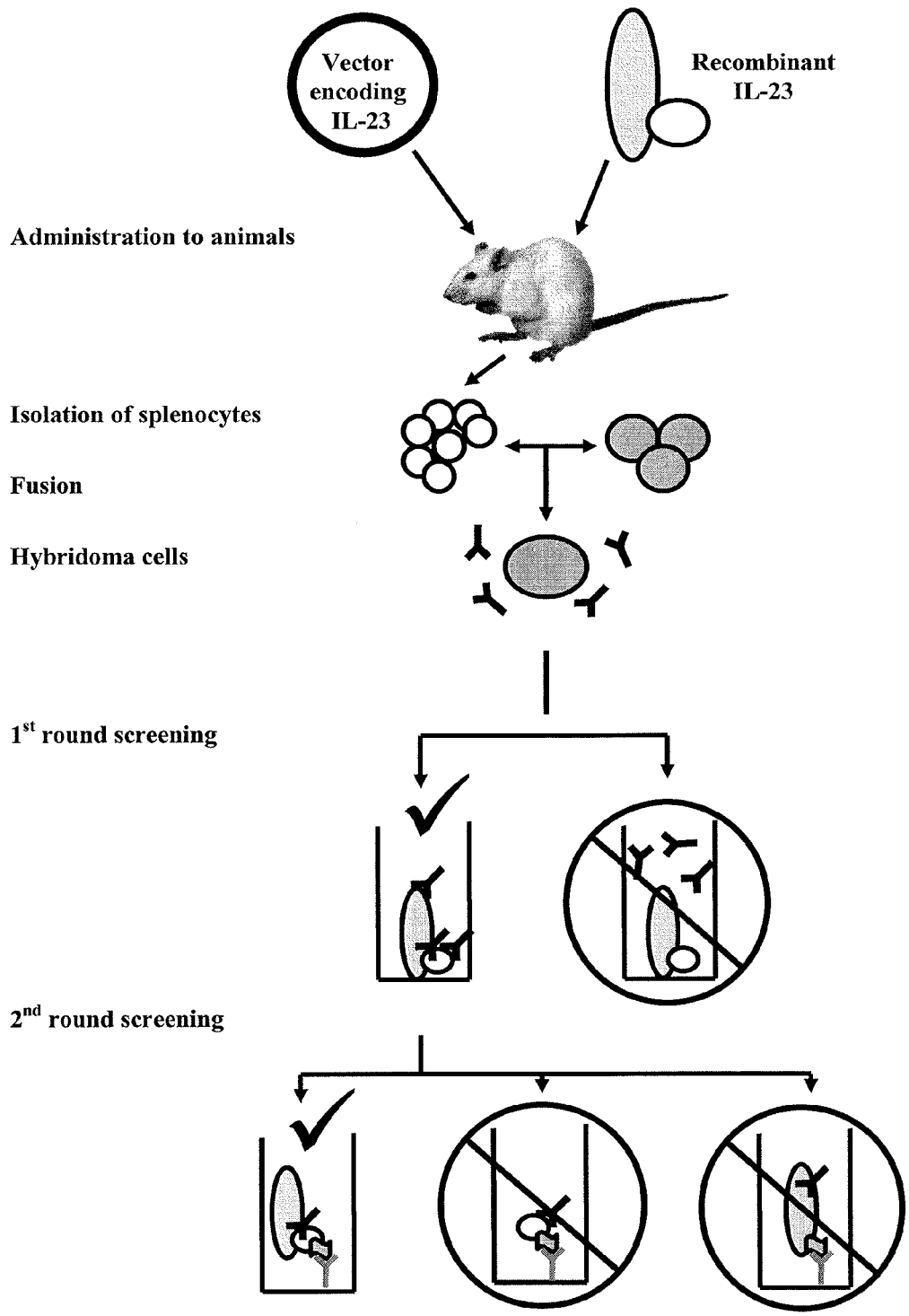

FIG. 11 is a diagrammatic representation showing methods for producing anti-IL-23 antibodies by immunizing animals.

Figure 12:
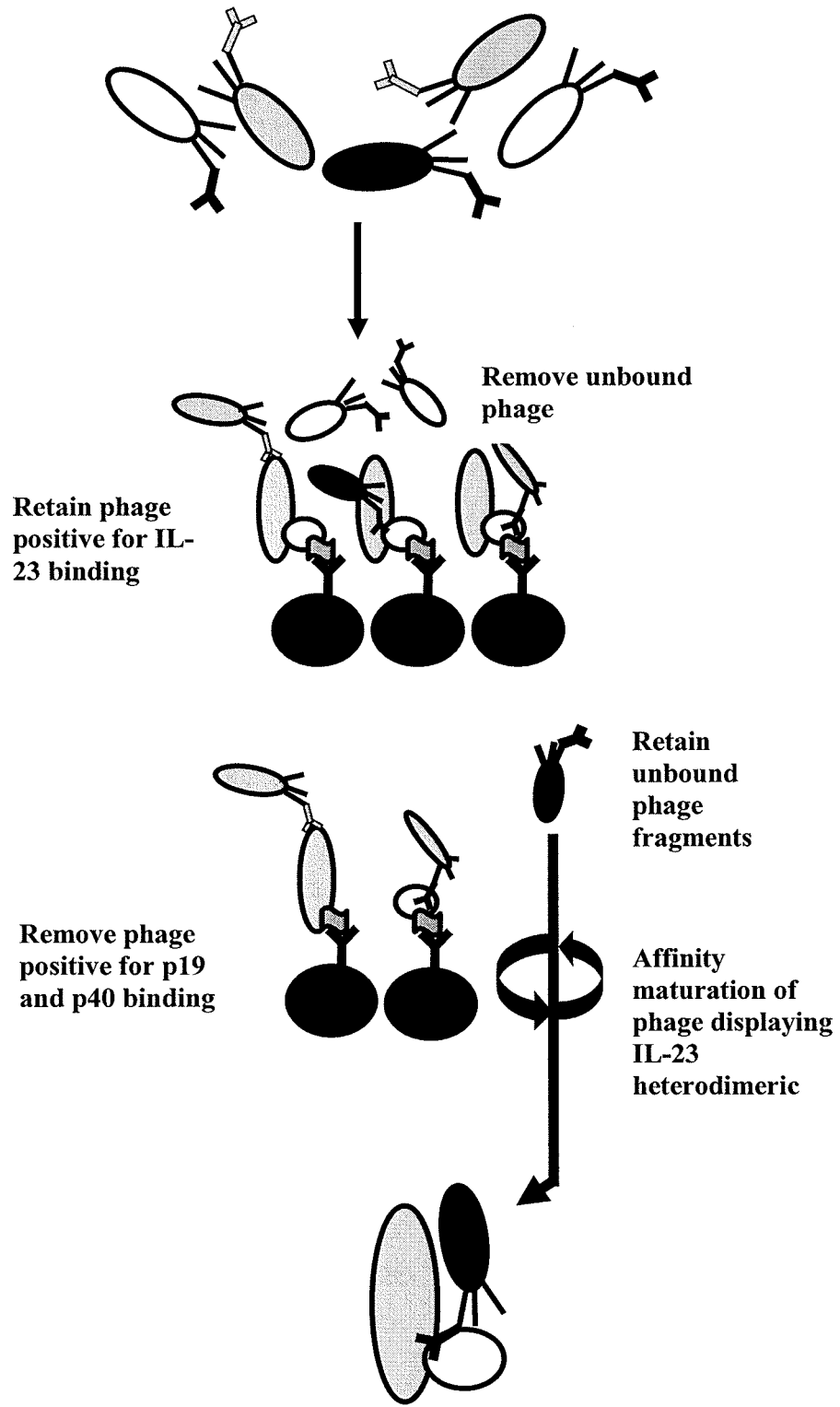

FIG. 12 is a diagrammatic representation showing methods for producing anti-IL-23 antibodies by phage display.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth. Each example of the disclosure is to be applied mutatis mutandis to each and every other embodiment unless specifically stated otherwise.

Each example of the disclosure is to be applied mutatis mutandis to a protein comprising a an antigen binding domain of an antibody, the antigen binding domain comprising a $V_H$ comprising a sequence set forth in SEQ ID NO: 49 and a $V_L$ comprising a sequence set forth in SEQ ID NO: 50.

Each example of the disclosure is to be applied mutatis mutandis to a protein comprising a an antigen binding domain of an antibody, the antigen binding domain comprising a $V_H$ comprising a sequence set forth in SEQ ID NO: 7 and a $V_L$ comprising a sequence set forth in SEQ ID NO: 12 or a humanized form thereof, e.g., comprising a $V_H$ and a $V_L$ of an antibody described in any one of rows 2-23 of Table 1.

Each example of the disclosure is to be applied mutatis mutandis to a protein comprising a an antigen binding domain of an antibody, the antigen binding domain comprising a $V_H$ and a $V_L$ of an antibody described in any one of rows 2, 3, 6 or 7 of Table 1.

Those skilled in the art will appreciate that the disclosure herein is susceptible to variations and modifications other than those specifically described. It is to be understood that the disclosure encompasses all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

The compositions of matter and methods described herein are produced or performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J F Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). Biochem. *Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

The term "and/or", e.g., "X and/or Y" shall be understood to mean either "X and Y" or "X or Y" and shall be taken to provide explicit support for both meanings or for either meaning.

As used herein, the term "between" in the context of a range between two values or a residue in a protein or polypeptide between two residues shall be read in an inclusive manner, i.e., as including any values/residues located between the two recited values/residues and the two recited values/residues. For example, the term "between 1 and 10" shall be understood to include 1, 2, 3, 4, 5, 6, 7, 8, 9 and 10.

In the context of the present specification refers to "any one of [or any one or more of] SEQ ID NOs: XX to YY" will be understood to provide literal support for a statement or claim defining any one (or one or more) of the sequences falling between (as defined herein) the recited SEQ ID NOs.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Key to Sequence Listing

SEQ ID NO: 1 is an amino acid sequence of a human IL-12p40 subunit.

SEQ ID NO: 2 is an amino acid sequence of a human IL23p19 subunit.

SEQ ID NO: 3 is an amino acid sequence of a human IgG1 heavy chain constant region.

SEQ ID NO: 4 is an amino acid sequence of a human light chain kappa constant region.

SEQ ID NO: 5 is a nucleotide sequence encoding a fusion protein comprising an IL-12p40 subunit and an IL-23p19 subunit separated by a flexible linker.

SEQ ID NO: 6 is a nucleotide sequence encoding a $V_H$ of antibody E11E7.

SEQ ID NO: 7 is an amino acid sequence of a $V_H$ of antibody E11E7.

SEQ ID NO: 8 is an amino acid sequence of a CDR1 of a $V_H$ of antibody E11E7 (according to the Kabat numbering system).

SEQ ID NO: 9 is an amino acid sequence of a CDR2 of a $V_H$ of antibody E11E7 (according to the Kabat numbering system).

SEQ ID NO: 10 is an amino acid sequence of a CDR3 of a $V_H$ of antibody E11E7 (according to the Kabat numbering system).

SEQ ID NO: 11 is a nucleotide sequence encoding a $V_L$ of antibody E11E7.

SEQ ID NO: 12 is an amino acid sequence of a $V_L$ of antibody E11E7. SEQ ID NO: 13 is an amino acid sequence of a CDR1 of a $V_L$ of antibody E11E7 (according to the Kabat numbering system).

SEQ ID NO: 14 is an amino acid sequence of a CDR2 of a $V_L$ of antibody E11E7 (according to the Kabat numbering system).

SEQ ID NO: 15 is an amino acid sequence of a CDR3 of a $V_L$ of antibody E11 E7 (according to the Kabat numbering system).

SEQ ID NO: 16 is an amino acid sequence of a human heavy chain constant region.

SEQ ID NO: 17 is an amino acid sequence of a FLAG tag.

SEQ ID NO: 18 is a nucleotide sequence encoding a $V_L$ of the E11E7 chimeric antibody.

SEQ ID NO: 19 is a nucleotide sequence encoding a $V_H$ of the E11E7 chimeric antibody.

SEQ ID NO: 20 is an amino acid sequence of a heavy chain of a chimeric antibody comprising E11E7 $V_H$ and human constant region (designated E11E7Chimera).

SEQ ID NO: 21 is an amino acid sequence of a light chain of a chimeric antibody comprising E11E7 $V_L$ and human constant region (designated E11E7Chimera).

SEQ ID NO: 22 is an amino acid sequence of an alternative CDR2 of a $V_H$ of an antibody that binds to IL-23 as described herein.

SEQ ID NO: 23 is an amino acid sequence of a consensus sequence of a CDR1 of a $V_H$ of an anti-IL-23 antibody (according to the enhanced Chothia numbering system).

SEQ ID NO: 24 is an amino acid sequence of a consensus sequence of a CDR2 of a $V_H$ of an anti-IL-23 antibody (according to the Kabat numbering system).

SEQ ID NO: 25 is an amino acid sequence of a consensus sequence of a CDR1 of a $V_H$ of a humanized anti-IL-23 antibody (according to the enhanced Chothia numbering system).

SEQ ID NO: 26 is an amino acid sequence of a consensus sequence of a $V_H$ of an anti-IL-23 antibody.

SEQ ID NO: 27 is an amino acid sequence of a consensus sequence of a $V_L$ of an anti-IL-23 antibody.

SEQ ID NO: 28 is an amino acid sequence of a consensus sequence of a $V_H$ of a humanized anti-IL-23 antibody.

SEQ ID NO: 29 is an amino acid sequence of a consensus sequence of a $V_L$ of a humanized anti-IL-23 antibody.

SEQ ID NO: 30 is an amino acid sequence of humanized antibody heavy chain number 20.

SEQ ID NO: 31 is an amino acid sequence of humanized antibody heavy chain number 21.

SEQ ID NO: 32 is an amino acid sequence of humanized antibody heavy chain number 6.

SEQ ID NO: 33 is an amino acid sequence of humanized antibody heavy chain number 8.

SEQ ID NO: 34 is an amino acid sequence of humanized antibody heavy chain number 9.

SEQ ID NO: 35 is an amino acid sequence of humanized antibody heavy chain number 16.

SEQ ID NO: 36 is an amino acid sequence of humanized antibody heavy chain number 1.

SEQ ID NO: 37 is an amino acid sequence of humanized antibody heavy chain number 13.

SEQ ID NO: 38 is an amino acid sequence of humanized antibody heavy chain number 7.

SEQ ID NO: 39 is an amino acid sequence of humanized antibody heavy chain number 11.
SEQ ID NO: 40 is an amino acid sequence of humanized antibody heavy chain number 18.
SEQ ID NO: 41 is an amino acid sequence of humanized antibody heavy chain number 5.
SEQ ID NO: 42 is an amino acid sequence of humanized antibody heavy chain number 10.
SEQ ID NO: 43 is an amino acid sequence of humanized antibody heavy chain number 14.
SEQ ID NO: 44 is an amino acid sequence of humanized antibody heavy chain number 15.
SEQ ID NO: 45 is an amino acid sequence of humanized antibody light chain number 4.
SEQ ID NO: 46 is an amino acid sequence of humanized antibody light chain number 22.
SEQ ID NO: 47 is an amino acid sequence of humanized antibody light chain number 12.
SEQ ID NO: 48 is an amino acid sequence of humanized antibody light chain number 23.
SEQ ID NO: 49 is an amino acid sequence of $V_H$ of human antibody number ST883/885.
SEQ ID NO: 50 is an amino acid sequence of $V_L$ of human antibody number ST883/885.
SEQ ID NO: 51 is an amino acid sequence of a CDR1 of a $V_H$ of human antibody number ST883/885.
SEQ ID NO: 52 is an amino acid sequence of a CDR2 of a $V_H$ of human antibody number ST883/885.
SEQ ID NO: 53 is an amino acid sequence of a CDR3 of a $V_H$ of human antibody number ST883/885.
SEQ ID NO: 54 is an amino acid sequence of a CDR1 of a $V_L$ of human antibody number ST883/885.
SEQ ID NO: 55 is an amino acid sequence of a CDR2 of a $V_L$ of human antibody number ST883/885.
SEQ ID NO: 56 is an amino acid sequence of a CDR3 of a $V_L$ of human antibody number ST883/885.
SEQ ID NO: 57 is a nucleotide sequence encoding a $V_H$ of humanized antibody heavy chain number 20.
SEQ ID NO: 58 is a nucleotide sequence encoding a $V_H$ of humanized antibody heavy chain number 21.
SEQ ID NO: 59 is a nucleotide sequence encoding a $V_H$ of humanized antibody heavy chain number 6.
SEQ ID NO: 60 is a nucleotide sequence encoding a $V_H$ of humanized antibody heavy chain number 8.
SEQ ID NO: 61 is a nucleotide sequence encoding a $V_H$ of humanized antibody heavy chain number 9.
SEQ ID NO: 62 is a nucleotide sequence encoding a $V_H$ of humanized antibody heavy chain number 16.
SEQ ID NO: 63 is a nucleotide sequence encoding a $V_H$ of humanized antibody heavy chain number 1.
SEQ ID NO: 64 is a nucleotide sequence encoding a $V_H$ of humanized antibody heavy chain number 13.
SEQ ID NO: 65 is a nucleotide sequence encoding a $V_H$ of humanized antibody heavy chain number 7.
SEQ ID NO: 66 is a nucleotide sequence encoding a $V_H$ of humanized antibody heavy chain number 11.
SEQ ID NO: 67 is a nucleotide sequence encoding a $V_H$ of humanized antibody heavy chain number 18.
SEQ ID NO: 68 is a nucleotide sequence encoding a $V_H$ of humanized antibody heavy chain number 5.
SEQ ID NO: 69 is a nucleotide sequence encoding a $V_H$ of humanized antibody heavy chain number 10.
SEQ ID NO: 70 is a nucleotide sequence encoding a $V_H$ of humanized antibody heavy chain number 14.
SEQ ID NO: 71 is a nucleotide sequence encoding a $V_H$ of humanized antibody heavy chain number 15.
SEQ ID NO: 72 is a nucleotide sequence encoding a $V_L$ of humanized antibody light chain number 4.
SEQ ID NO: 73 is a nucleotide sequence encoding a $V_L$ of humanized antibody light chain number 22.
SEQ ID NO: 74 is a nucleotide sequence encoding a $V_L$ of humanized antibody light chain number 12.
SEQ ID NO: 75 is a nucleotide sequence encoding a $V_L$ of humanized antibody light chain number 23.
SEQ ID NO: 76 is a nucleotide sequence encoding $V_H$ of human antibody number ST883/885.
SEQ ID NO: 77 is a nucleotide sequence encoding $V_L$ of human antibody number ST883/885.
SEQ ID NO: 78 is an amino acid sequence of a fusion protein comprising the following
linked components: IL-12p40-linker-IL-23p19.
SEQ ID NO: 79 is an amino acid sequence of a HIS tag.
SEQ ID NO: 80 is an amino acid sequence of an AviHIS tag.
SEQ ID NO: 81 is an amino acid sequence of a leader sequence of a heavy chain of an antibody.
SEQ ID NO: 82 is an amino acid sequence of a leader sequence of a light chain of an antibody.
SEQ ID NO: 83 is an amino acid sequence of a human light chain lambda constant region Selected Definitions The term "isolated protein" or "isolated polypeptide" is a protein or polypeptide that by virtue of its origin or source of derivation is not associated with naturally-associated components that accompany it in its native state or is substantially free of other proteins from the same species. A protein may be rendered substantially free of naturally associated components by isolation, using protein purification techniques known in the art. The term "recovering" as used herein, refers to the process of rendering a chemical species, such as a polypeptide, substantially free of naturally associated components by isolation, e.g., using protein purification techniques known in the art. In one example, an isolated protein is substantially purified. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody variable region. Similarly, if a nucleic acid encoding the protein is isolated and expressed using recombinant means, the resulting protein is a recombinant protein comprising an antibody antigen binding domain A recombinant protein also encompasses a protein expressed by artificial recombinant means when it is within a cell, tissue or subject, e.g., in which it is expressed.

The term "IL-23-binding protein" shall be taken to include a single polypeptide chain (i.e., a series of contiguous amino acids linked by peptide bonds), or a series of polypeptide chains covalently or non-covalently linked to one another (i.e., a polypeptide complex) capable of binding to IL-23 in the manner described and/or claimed herein. For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide chain" from the foregoing paragraph will be understood to mean a series of contiguous amino acids linked by peptide bonds.

As used herein, the term "antigen binding domain" shall be taken to mean a region of an antibody that is capable of specifically binding to an antigen, i.e., a $V_H$ or a $V_L$ or a Fv. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., IL-23) by virtue of an antigen binding site contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half antibodies, bispecific antibodies). An antibody generally comprises constant domains, which can be arranged into a constant region or constant fragment or fragment crystallisable (Fc). Exemplary forms of antibodies comprise a four-chain structure as their basic unit. Full-length antibodies comprise two heavy chains (~50-70 kD) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H1$ which is 330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (such as, human) antibody. In one example, the antibody is humanized, synhumanized, chimeric, CDR-grafted or deimmunized.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. In one example, the amino acid positions assigned to CDRs and FRs are defined according to Kabat *Sequences of Proteins of Immunological Interest*, National Institutes of Health, Bethesda, Md., 1987 and 1991 (also referred to herein as "the Kabat numbering system". In another example, the amino acid positions assigned to CDRs and FRs are defined according to the Enhanced Chothia Numbering Scheme (http://www.bioinfo.org.uk/mdex.html). According to the numbering system of Kabat, $V_H$ FRs and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). The present disclosure is not limited to FRs and CDRs as defined by the Kabat numbering system, but includes all numbering systems, including the canonical numbering system or of Chothia and Lesk *J. Mol. Biol.* 196:901-917, 1987; Chothia et al. Nature 342, 877-883, 1989; and/or Al-Lazikani et al., *J Mol Biol* 273, 927-948, 1997; the numbering system of Honnegher and Plükthun *J. Mol. Biol.*, 309: 657-670, 2001; or the IMGT system discussed in Giudicelli et al., *Nucleic Acids Res.*, 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In an additional, or alternative, option, light chain CDR1 does not comprise the four N-terminal amino acids listed herein or any one or more of those amino acids are substituted with another naturally-occurring amino acid. In this regard, Padlan et al., *FASEB J.*, 9: 133-139, 1995 established that the five C-terminal amino acids of heavy chain CDR2 and/or the four N-terminal amino acids of light chain CDR1 are not generally involved in antigen binding.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore an Fv of the disclosure (as well as any protein of the disclosure) may have multiple antigen binding sites which may or may not bind the same antigen. This term shall be understood to encompass fragments directly derived from an antibody as well as recombinant forms of such proteins. In some examples, the $V_H$ is not linked to the heavy chain constant domain $C_H1$ and/or the $V_L$ is not linked to a light chain constant domain $C_L$. Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. An "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. An "F(ab')$_2$ fragment" of an antibody consists of a dimer of two Fab' fragments held together by two disulfide bonds, and is obtained by treating a whole antibody molecule with the enzyme pepsin, without subsequent reduction. An "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker. A detailed discussion of exemplary Fv containing proteins falling within the scope of this term is provided herein below.

As used herein, the term "specifically binds" or "binds specifically" shall be taken to mean that an IL-23-binding protein of the disclosure reacts or associates more frequently, more rapidly, with greater duration and/or with greater affinity with a particular antigen or antigens or cell expressing same than it does with alternative antigens or cells. For example, a protein that "specifically binds" to an antigen binds that antigen with greater affinity, avidity, more readily, and/or with greater duration than it binds to other antigens. It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". In one example, "specific binding" an IL-23-binding protein of the disclosure to an antigen, means that the protein binds to the antigen with an affinity constant of 100 nM or less, such as 50 nM or less, for example 20 nM or less, such as, 1 nM or less.

As used herein, the term "does not significantly bind" shall be taken to mean that an IL-23-binding protein of the disclosure displays 10 fold, or 20 fold or 50 fold or 60 fold or 70 fold or 80 fold or 90 fold or 100 fold, less binding to the IL-23p19 subunit and to the IL-12p40 subunit when they are not components of IL-23 than it does to IL-23, when tested under the same conditions. In some examples, an IL-23-binding protein of the disclosure has an equilibrium constant ($K_D$) for the IL-23p19 subunit and for the IL-12p40 subunit when they are not components of IL-23 of $1 \times 10^{-6}$ or less and, for example, the protein has a $K_D$ for IL-23 of at least about $1 \times 10^{-8}$, such as $5 \times 10^{-9}$. This decreased level of binding may be measured by ELISA or biosensor analysis (e.g., Biacore). In one example, an IL-23-binding protein of the disclosure does not detectably bind to IL-23p19 or IL-12p40 when they are not components of IL-23, e.g., as measured by ELISA or Biacore or Western Blot or FACS. In this regard, "does not detectably bind" shall be understood to mean that the level of binding is not significantly greater than background, e.g., as determined using an isotype control antibody.

The term "the IL-12p40 subunit and IL-23p19 subunit when they are not components of IL-23" encompasses the IL-23p19 subunit or the IL-12p40 subunit in isolation or when they are complexed with another polypeptide (i.e., the IL-12p40 subunit may be complexed with a polypeptide other than IL-23p19, such as IL-12p35).

The term "IL-23" as used herein includes a heterodimeric human cytokine belonging to a family of five such heterodimeric cytokines including IL-12 and IL-27 (Trinchieri, Pflanz et al. 2003 Immunity 19 641-4). The term includes a heterodimeric protein comprising the subunits IL-23p19 and IL-12p40 which are linked together, e.g., with a disulfide bridge. The term IL-23 is intended to include recombinant IL-23 (rIL-23), which can be prepared by standard recombinant expression methods. In some examples, the disclosure encompasses human IL-23 (abbreviated herein as hIL-23, or IL-23), including recombinant forms thereof (i.e., rhIL-23). The term "IL-12/23" as used herein, refers to IL-12 and IL-23 collectively.

The term "IL-12p40", identical to "IL-23p40", and also referred to simply as "p40" and "p40 subunit" or "IL-12p40 subunit", as used herein, includes the 40 kDa subunit of the cytokine IL-12 and the 40 kDa subunit of the cytokine IL-23 (e.g., of human IL-12 and/or IL-23). For the purposes of nomenclature and not limitation an amino acid sequence of an IL-12p40 subunit is set forth in SEQ ID NO: 1. In one example, an IL-12p40 subunit as discussed herein comprises a sequence set forth in SEQ ID NO: 1.

The term "isolated IL-12p40 subunit" shall betaken to mean the IL-12p40 subunit as defined above in a form in which it does not form a component of a heterodimer, e.g., with another interleukin protein. This term does not mean that the "isolated IL-12p40 subunit" contains no other protein or polypeptide sequences. For example, the IL-12p40 subunit can be fused to another polypeptide, e.g., a FLAG tag or a Fc region of an antibody. This term also is not limited to the IL-12p40 subunit in monomeric form (however this is one example of the "isolated IL-12p40 subunit" encompassed by the definition), since if it is fused to a Fc region of an antibody it may form homodimers.

The term "IL-23p19", also referred to simply as "p19" or "p19 subunit", as used herein, includes the 19 kDa subunit of the cytokine IL-23 (e.g., of human IL-23). For the purposes of nomenclature and not limitation an amino acid sequence of an IL-23p19 subunit is set forth in SEQ ID NO: 2. In one example, an IL-23p19 subunit as discussed herein comprises a sequence set forth in SEQ ID NO: 2.

The term "isolated IL-23p19 subunit" shall betaken to mean the IL-23p19 subunit as defined above in a form in which it does not form a component of a heterodimer, e.g., with another interleukin protein. This term does not mean that the "isolated IL-23p19 subunit" contains no other protein or polypeptide sequences. For example, the IL-23p19 subunit can be fused to another polypeptide, e.g., a FLAG tag or a Fc region of an antibody. This term also is not limited to the IL-23p19 subunit in monomeric form (however this is one example of the "isolated IL-23p19 subunit" encompassed by the definition), since if it is fused to a Fc region of an antibody it may form homodimers.

As used herein, the term "heterodimer" shall be understood to mean a protein complex comprising two different cytokine subunits, e.g. IL-23p19 and IL-12p40 forms an IL-23 heterodimer; and IL-12p40 and IL-12p35 form an IL-12 heterodimer. As used herein, the term "monomeric" shall be taken to mean that a subunit of IL-12 is not in direct contact with another cytokine subunit.

"Biological activity" as used herein, refers to one or more biological properties of IL-23. Biological properties of IL-23 include but are not limited to binding IL-12Rβ1 on a cell and/or IL-23R on a cell, inducing IFN-γ production following binding to a cell, inducing IL-17 production following binding to a cell, inducing IL-21 production following binding to a cell, inducing IL-22 production following binding to a cell, inducing $T_H17$ cell differentiation and activating the antigen-presenting functions of dendritic cells, and selectively inducing proliferation of memory T cells.

Figure 2:
FIG. 2 is a diagrammatic representation showing the position of regions of IL-23 protected by binding of E11E7 during hydrogen/deuterium exchange experiments. Black atoms represent amino acids on IL-23p19 that demonstrated high % deuterium difference across overlapping peptides. Gray atoms represent amino acids on IL-12p40 that demonstrated high % deuterium difference across overlapping peptides.

As used herein, the term "heterodimeric interface" shall be taken to mean a region of IL-23 surrounding sites at which IL-12p40 and IL-23p19 contact one another and/or are linked to one another and/or are sufficiently close to permit binding of a protein such that it binds to IL-23 while not significantly binding to an IL-12p40 subunit and/or an IL-23p19 subunit when they are not components of IL-23. In this regard, this term does not limit to only those residues in IL-12p40 and IL-23p19 that actually contact one another. Rather, the residues need only be within the region of the proteins involved in heterodimerization (e.g., as depicted in FIG. 2) and exposed as to permit protein binding and to permit specific binding to IL-23 heterodimer In one example, the "heterodimeric interface" is an epitope that is produced by dimerization of the protein, e.g., comprises amino acids of IL-12p40 and IL-23p19.

As used herein, the term "epitope" (syn. "antigenic determinant") shall be understood to mean a region of IL-23 to which a protein comprising an antigen binding domain of an antibody binds. This term is not necessarily limited to the specific residues or structure to which the protein makes contact. For example, this term in intended to encompass a region which includes amino acids contacted by the protein and/or 10 or more or 5-10 or 2-5 or 1-3 amino acids outside of this region. In some examples, the epitope is a linear series of amino acids produced upon dimerization of IL-12p40 and IL-23p19. However, an epitope can also comprise a series of discontinuous amino acids that are positioned close to one another (e.g., within about 50 Angstroms of one another, such as 40 Angstroms of one another, for example, 30 Angstroms of one another, such as within about 25 Angstroms of one another) when IL-23 is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain embodiments, may have specific three dimensional structural characteristics, and/or specific charge characteristics. An epitope or peptide or polypeptide comprising same can be administered to an animal to generate antibodies against the epitope.

The term "competitively inhibits" shall be understood to mean that an IL-23-binding protein of the disclosure reduces or prevents binding of an antibody comprising a heavy chain variable region comprising a sequence set forth in SEQ ID NO: 7 and a light chain variable region comprising a sequence set forth in SEQ ID NO: 12 to IL-23. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, the antibody is exposed to IL-23 either in the presence or absence of the protein. If less antibody binds in the presence of the protein than in the absence of the protein, the protein is considered to competitively inhibit binding of the antibody. For example, the protein and antibody are exposed to IL-23 substantially simultaneously. In one example, the competitive inhibition of binding is caused by the antigen binding domain of the protein on IL-23 overlapping with the antigen binding domain of the antibody.

"Overlapping" in the context of two epitopes shall be taken to mean that two epitopes share a sufficient number of amino acid residues to permit a protein that binds to one epitope to competitively inhibit the binding of a protein that binds to the other epitope. For example, the present disclosure encompasses a protein that binds to an epitope sharing a sufficient number of residues to prevent binding of an antibody comprising a heavy chain variable region comprising a sequence set forth in SEQ ID NO: 7 and a light chain variable region comprising a sequence set forth in SEQ ID NO: 12 to its epitope.

A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

As used herein, a "condition" is a disruption of or interference with normal function, and is not to be limited to any specific condition, and will include diseases or disorders.

As used herein, the terms "preventing", "prevent" or "prevention" include administering a therapeutically effective amount of an IL-23-binding protein of the disclosure sufficient to stop or hinder the development of at least one symptom of a specified disease or condition.

As used herein, the terms "treating", "treat" or "treatment" include administering a therapeutically effective amount of a protein described herein sufficient to reduce or eliminate at least one symptom of a specified disease or condition.

As used herein, the term "subject" shall be taken to mean any animal, such as, a mammal. In one example, the mammal is a human or non-human primate. For example, the mammal is a human.

Reference herein to a "sample" should be understood as a reference to any sample derived from a subject such as, but not limited to, a body fluid (e.g., blood or synovial fluid or cerebrospinal fluid), cellular material (e.g. tissue aspirate), tissue biopsy specimens or surgical specimens. The "sample" includes extracts and/or derivatives and/or fractions of said sample, e.g., serum, plasma, peripheral blood mononuclear cells (PBMC), or a buffy coat fraction.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease, including the chance of recovery or recurrence or the outcome of treatment.

Proteins Comprising Antibody Variable Regions
Antibodies
Immunization-Based Methods To generate antibodies, IL-23 or a modified form thereof (e.g., a fusion protein comprising IL12p40 subunit fused to IL-23p19 subunit) or nucleic acid encoding same, optionally formulated with any suitable or desired carrier, adjuvant, or pharmaceutically acceptable carrier, is conveniently administered to a subject (such as, a non-human subject, such as, a mouse, a rat, a chicken etc.) in the form of an injectable composition. Injection may be intranasal, intramuscular, subcutaneous, intravenous, intradermal, intraperitoneal, or by other known route. Optionally, the IL-23 or DNA encoding same is administered numerous times. Means for preparing and characterizing antibodies are known in the art. (See, e.g., Antibodies: A Laboratory Manual, Cold Spring Harbor Laboratory, 1988).

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (Mabs).

Monoclonal antibodies are exemplary antibodies contemplated by the present disclosure. Generally, such a method involves, immunizing a subject (e.g., a rodent, e.g., mouse or rat) with IL-23 or nucleic acid encoding same under conditions sufficient to stimulate antibody producing cells. In some examples, a mouse genetically-engineered to express human immunoglobulin proteins and not express murine immunoglobulin proteins, is immunized to produce an antibody (e.g., as described in PCT/US2007/008231 and/or Lonberg et al., *Nature* 368 (1994): 856-859). Following immunization, antibody producing somatic cells (e.g., B lymphocytes) are fused with immortal cells, e.g., immortal myeloma cells. Various methods for producing such fused cells (hybridomas) are known in the art and described, for example, in Kohler and Milstein, *Nature* 256, 495-497, 1975. The hybridoma cells can then be cultured under conditions sufficient for antibody production.

The present disclosure contemplates other methods for producing antibodies, e.g., ABL-MYC technology (as described, for example in Largaespada et al, *Curr. Top. Microbiol. Immunol*, 166, 91-96. 1990).

Library-Based Methods

The present disclosure also encompasses screening of libraries of antibodies or proteins comprising variable regions thereof to identify an IL-23-binding protein of the disclosure.

Examples of this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. Nos. 5,885,793; 6,204,023; 6,291,158; or 6,248,516.

The IL-23-binding proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, e.g., as described in U.S. Pat. Nos. 6,300, 064; 5,885,793; 6,204,023; 6,291,158; or 6,248,516. Other phage display methods are known in the art and are contemplated by the present disclosure. Similarly, methods of cell display are contemplated by the disclosure, e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the present disclosure is screened using affinity purification, e.g., as described in Scopes (In: Protein purification: principles and practice, Third Edition, Springer Verlag, 1994). Methods of affinity purification typically involve contacting proteins comprising antigen binding domains displayed by the library with a target antigen (e.g., IL-23) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., *J Immunol Methods*. 354:85-90, 2010; or Jostock et al., *J Immunol Methods*, 289: 65-80, 2004. Alternatively, or additionally, standard cloning methods are used, e.g., as described in Ausubel et al (In: Current Protocols in Molecular Biology. Wiley Interscience, ISBN 047 150338, 1987), and/or (Sambrook et al (In: Molecular Cloning: Molecular Cloning: A Laboratory Manual, Cold Spring Harbor Laboratories, New York, Third Edition 2001).

Selection of Proteins that Specifically Bind to IL-23

Suitable methods for selecting a protein comprising an antibody binding domain that specifically binds to IL-23 are available to those skilled in the art.

For example, a screen may be conducted to identify proteins capable of binding to IL-23 of the disclosure. Any proteins that bind to IL-23 are then screened to identify those that are incapable of binding to IL-23p19 or IL-12p40 when not components of IL-23 (e.g., in isolation or part of another cytokine, e.g., IL-12). Of course, the order of these screens can also be reversed.

An example of this type of screen is depicted in FIG. 11 and/or exemplified herein. Following repeated administration of recombinant IL-23 or genetic immunization of a vector expressing IL-23 to mice, a fusion of murine splenocytes with myeloma cells is performed resulting in hybridoma cells. Antibodies secreted by these hybridoma cells are then screened in a first round against native IL-23. Positive hybridomas are then tested in the second round against FLAG-tagged IL-23, IL-23p19 and IL-12p40. Antibodies that are positive for IL-23-binding but not IL-23p19 and IL-12p40 are heterodimeric specific antibodies.

In the case of displayed proteins, panning can be used to subtract those proteins that do not bind specifically to IL-23. For example, phage displaying proteins that bind to IL-23 are then exposed to IL-23p19 or IL-12p40 when not components of the IL-23 (e.g., in isolation or part of another cytokine) thereby removing binding proteins that bind discreetly to IL-12p40 or IL-23p19, i.e., cross-reactive proteins.

An example of this type of method is depicted in FIG. 12 and/or exemplified herein. In this example, phage are first screened (or panned) for binding to IL-23, with unbound phage removed and bound phage retained. The bound phage are then tested for binding to IL-12p40 and IL-23p19 subunits with bound phage removed and unbound phage retained. After several rounds of panning an antibody fragment having the requisite specificity for IL-23 is obtained.

Another method involves identifying an epitope formed or exposed upon dimerization of IL-23p19 and IL-12p40 that is not present or exposed when those polypeptides are not dimerized and using a peptide or polypeptide comprising said epitope as an antigen to produce proteins of the disclosure.

Deimmunized, Chimeric, Humanized, Synhumanized, Primatized and Human Proteins

The IL-23-binding proteins of the present disclosure may be may be a humanized protein.

The term "humanized protein" shall be understood to refer to a protein comprising a human-like variable region including CDRs from an antibody from a non-human species (e.g., mouse or rat or non-human primate) grafted onto or inserted into FRs from a human antibody (this type of antibody is also referred to a "CDR-grafted antibody"). As exemplified herein, humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or 5,585,089. The term "humanized protein" also encompasses a super-humanized protein, e.g., as described in U.S. Pat. No. 7,732,578.

In one example, the present disclosure provides a humanized antibody comprising:

(i) a heavy chain comprising a sequence set forth in SEQ ID NO: 30 and a light chain comprising a sequence set forth in SEQ ID NO: 45;
(ii) a heavy chain comprising a sequence set forth in SEQ ID NO: 31 and a light chain comprising a sequence set forth in SEQ ID NO: 45;
(iii) a heavy chain comprising a sequence set forth in SEQ ID NO: 32 and a light chain comprising a sequence set forth in SEQ ID NO: 46;
(iv) a heavy chain comprising a sequence set forth in SEQ ID NO: 33 and a light chain comprising a sequence set forth in SEQ ID NO: 46;
(v) a heavy chain comprising a sequence set forth in SEQ ID NO: 34 and a light chain comprising a sequence set forth in SEQ ID NO: 46;
(vi) a heavy chain comprising a sequence set forth in SEQ ID NO: 35 and a light chain comprising a sequence set forth in SEQ ID NO: 47;
(vii) a heavy chain comprising a sequence set forth in SEQ ID NO: 33 and a light chain comprising a sequence set forth in SEQ ID NO: 48;
(viii) a heavy chain comprising a sequence set forth in SEQ ID NO: 34 and a light chain comprising a sequence set forth in SEQ ID NO: 48;
(ix) a heavy chain comprising a sequence set forth in SEQ ID NO: 32 and a light chain comprising a sequence set forth in SEQ ID NO: 48;
(x) a heavy chain comprising a sequence set forth in SEQ ID NO: 36 and a light chain comprising a sequence set forth in SEQ ID NO: 45;
(xi) a heavy chain comprising a sequence set forth in SEQ ID NO: 37 and a light chain comprising a sequence set forth in SEQ ID NO: 47;
(xii) a heavy chain comprising a sequence set forth in SEQ ID NO: 38 and a light chain comprising a sequence set forth in SEQ ID NO: 46;
(xiii) a heavy chain comprising a sequence set forth in SEQ ID NO: 39 and a light chain comprising a sequence set forth in SEQ ID NO: 46;
(xiv) a heavy chain comprising a sequence set forth in SEQ ID NO: 40 and a light chain comprising a sequence set forth in SEQ ID NO: 45;
(xv) a heavy chain comprising a sequence set forth in SEQ ID NO: 41 and a light chain comprising a sequence set forth in SEQ ID NO: 46;
(xvi) a heavy chain comprising a sequence set forth in SEQ ID NO: 42 and a light chain comprising a sequence set forth in SEQ ID NO: 46;
(xvii) a heavy chain comprising a sequence set forth in SEQ ID NO: 43 and a light chain comprising a sequence set forth in SEQ ID NO: 47;
(xviii) a heavy chain comprising a sequence set forth in SEQ ID NO: 38 and a light chain comprising a sequence set forth in SEQ ID NO: 48;
(xix) a heavy chain comprising a sequence set forth in SEQ ID NO: 39 and a light chain comprising a sequence set forth in SEQ ID NO: 48;
(xx) a heavy chain comprising a sequence set forth in SEQ ID NO: 44 and a light chain comprising a sequence set forth in SEQ ID NO: 47;
(xxi) a heavy chain comprising a sequence set forth in SEQ ID NO: 41 and a light chain comprising a sequence set forth in SEQ ID NO: 48; or
(xxii) a heavy chain comprising a sequence set forth in SEQ ID NO: 42 and a light chain comprising a sequence set forth in SEQ ID NO: 48.
(i) a heavy chain comprising a sequence set forth in SEQ ID NO: 30 and a light chain comprising a sequence set forth in SEQ ID NO: 45;
(ii) a heavy chain comprising a sequence set forth in SEQ ID NO: 31 and a light chain comprising a sequence set forth in SEQ ID NO: 45;
(iii) a heavy chain comprising a sequence set forth in SEQ ID NO: 32 and a light chain comprising a sequence set forth in SEQ ID NO: 46; or
(iv) a heavy chain comprising a sequence set forth in SEQ ID NO: 33 and a light chain comprising a sequence set forth in SEQ ID NO: 46.

In one example, a humanized protein comprises the regions between 27d and 34, 50 and 55, and 89 and 96 in a light chain sequence disclosed herein; and 31 and 35b, 50 and 58, and 95 and 101 in a heavy chain sequence disclosed herein (numbering according to the Kabat numbering system). In this regard, Padlan et al., FASEB 1, 9: 133-139, 1995 presents evidence that these regions are those most likely to bind or contact antigen.

The IL-23-binding proteins of the present disclosure may be human proteins. The term "human protein" as used herein refers to proteins having variable and, optionally, constant antibody regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein. These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. A human protein will also be considered to include a protein comprising FRs from a human antibody or FRs comprising sequences from a consensus sequence of human FRs and in which one or more of the CDRs are random or semi-random, e.g., as described in U.S. Pat. Nos. 6,300,064 and/or 6,248,516.

The IL-23-binding proteins of the present disclosure may be synhumanized proteins. The term "synhumanized protein" refers to a protein prepared by a method described in WO2007/019620. A synhumanized IL-23-binding protein includes a variable region of an antibody, wherein the variable region comprises FRs from a New World primate antibody variable region and CDRs from a non-New World primate antibody variable region. For example, a synhumanized IL-23-binding protein includes a variable region of an antibody, wherein the variable region comprises FRs from a New World primate antibody variable region and CDRs from a mouse or rat antibody, e.g., E11E7 as described herein. In one example, the synhumanized IL-23-binding protein is an IL-23-binding antibody in which one or both of the variable regions are synhumanized.

The IL-23-binding proteins of the present disclosure may be primatized proteins. A "primatized protein" comprises variable region(s) from an antibody generated following immunization of a non-human primate, e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example an IL-23-binding protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397).

The present disclosure also contemplates a deimmunized protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein. For example, an IL-23-binding protein of the disclosure is analyzed to identify one or more B or T cell epitopes and one or more amino acid residues within the epitope is mutated to thereby reduce the immunogenicity of the IL-23-binding protein.

Other IL-23-Binding Proteins Comprising an Antigen Binding Domain

The present disclosure also contemplates other antigen binding domain-containing proteins, such as:
(i) a single-domain antibody, which is a single polypeptide chain comprising all or a portion of the $V_H$ or a $V_L$ of an antibody (see, e.g., U.S. Pat. No. 6,248,516);
(ii) diabodies, triabodies and tetrabodies, e.g., as described in U.S. Pat. No. 5,844,094 and/or US2008152586;
(iii) scFvs, e.g., as described in U.S. Pat. No. 5,260,203;
(iv) minibodies, e.g., as described in U.S. Pat. No. 5,837,821;
(v) "key and hole" bispecific proteins as described in U.S. Pat. No. 5,731,168;
(vi) heteroconjugate proteins, e.g., as described in U.S. Pat. No. 4,676,980;
(vii) heteroconjugate proteins produced using a chemical cross-linker, e.g., as described in U.S. Pat. No. 4,676,980;
(viii) Fab'-SH fragments, e.g., as described in Shalaby et al, *J. Exp. Med.*, 175: 217-225, 1992; or
(ix) Fab$_3$ (e.g., as described in EP19930302894).

Constant Domain Fusions

The present disclosure encompasses a protein comprising an antigen binding domain of an antibody and a constant region (e.g., Fc) or a domain thereof, e.g., $C_H2$ and/or $C_H3$ domain. Suitable constant regions and/or domains will be apparent to the skilled artisan and/or the sequences of such polypeptides are readily available from publicly available databases, such as is available from the National Center for Biotechnology Information. Kabat et al also provide description of some suitable constant regions/domains In some examples, the constant region or portion thereof of the IL-23-binding protein is derived from a human antibody. The constant region or portion thereof may be derived from any antibody class, including IgM, IgG, IgD, IgA and IgE, and any antibody isotype, including IgG1, IgG2, IgG3 and IgG4. Exemplary sequences of constant regions are included in US20070148167.

Constant regions and/or domains thereof are useful for providing or modifying or enhancing biological activities such as, dimerization, extended serum half life (e.g., by binding to FcRn), antigen dependent cell cytotoxicity (ADCC), complement dependent cytotoxicity (CDC), and/or antigen dependent cell phagocytosis (ADCP).

The present disclosure also contemplates proteins comprising mutant constant regions or domains, e.g., as described in U.S. Pat. Nos. 7,217,797; 7,217,798; or US20090041770 (having increased half-life) or US2005037000 (increased ADCC).

For example, the IL-23-binding protein comprises one or more amino acid substitutions that increase the half-life of the protein. For example, the IL-23-binding protein comprises a constant region comprising one or more amino acid substitutions that increase the affinity of the constant region for the neonatal Fc region (FcRn). For example, the constant region has increased affinity for FcRn at lower pH, e.g., about pH 6.0, to facilitate Fc/FcRn binding in an endosome. In one example, the constant region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Neutralizing proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., *Proc. Natl. Acad. USA,* 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Mutant Proteins

As discussed herein, the present disclosure provides a protein or nucleic acid having at least 80% identity to the sequence of the disclosure.

In one example, an IL-23-binding protein of the disclosure comprises a $V_H$ comprising a sequence at least about 80% or 85% or 90% or 95% or 97% or 98% or 99% identical to a sequence set forth in set forth in any one of SEQ ID NO: 7 or amino acids 1-120 of any one of SEQ ID NOs: 30 to 44, or SEQ ID NO: 49, wherein the protein is capable of specifically binding to IL-23 but not significantly binding to an IL-12p40 subunit and not significantly binding to an IL-23p19 subunit when they are not components of IL-23. Alternatively, or additionally, the protein comprises a CDR (e.g., three CDRs) at least about 80% or 85% or 90% or 95% or 97% or 98% or 99% identical to CDR(s) of a $V_H$ as described herein according to any example, and capable of specifically binding to IL-23 but not significantly binding to an IL-12p40 subunit and not significantly binding to an IL-23p19 subunit when they are not components of IL-23. Methods for determining binding of a protein to IL-23, IL-23p19 and IL-12p40 are described herein.

For example, the inventors have produced a series of $V_H$ regions having variation at about 30% of residues. Thus, a protein can comprise a $V_H$ comprising a sequence at least about 70% identical to a $V_H$ sequence disclosed herein. In one example, the sequence is at least 85% or 95% identical.

The inventors have also produced a series of humanized $V_H$ regions having variation at about 11% of residues. Thus, a protein can comprise a $V_H$ comprising a sequence at least about 89% identical to a $V_H$ sequence disclosed herein. In one example, the sequence is at least 90% or 95% identical.

The inventors have also identified residues in heavy chain CDR2 according to the Kabat numbering system that can be mutated while maintaining the specific binding to IL-23 without significantly binding to an IL-12p40 subunit and without significantly binding to an IL-23p19 subunit when they are not components of IL-23. For example, two of 16 residues can be mutated (12.5% of residues). Thus, a protein can comprise a CDR2 having at least about 87.5% identity to a heavy chain CDR2 sequence disclosed herein.

As discussed herein, it is also known in the art that the five C-terminal residues of heavy chain CDR2 can be mutated to conservative or non-conservative amino acid substitutions (31% of residues) (Padlan et al., *FASEB J.,* 9: 133-139, 1995). Thus, a protein can comprise a CDR2 having at least about 69% identity to a heavy chain CDR2 sequence disclosed herein.

The inventors have also identified residues in heavy chain CDR1 according to the enhanced Chothia numbering system that can be mutated while maintaining the specific binding to IL-23 without significantly binding to an IL-12p40 subunit and without significantly binding to an IL-23p19 subunit when they are not components of IL-23. For example, two of seven residues can be mutated (28% or 43% of residues) or three of seven residues can be mutated (43% of residues). Thus, a protein can comprise a CDR2 having at least about 72% identity to a heavy chain CDR1 sequence disclosed herein.

In another example, a nucleic acid of the disclosure comprises a sequence at least about 80% or 85% or 90% or 95% or 97% or 98% or 99% identical to a sequence set forth in any one of SEQ ID NOs: 6, 19, 57 to 71 or 76. The present disclosure also encompasses nucleic acids encoding a protein comprising a sequence set forth in any one of SEQ ID NOs: SEQ ID NO: 7, 26, 28, or amino acids 1-120 of any one of SEQ ID NOs: 30 to 44, or SEQ ID NO: 49, which differs from a sequence exemplified herein as a result of degeneracy of the genetic code.

In one example, an IL-23-binding protein of the disclosure comprises a $V_L$ comprising a sequence at least about 80% or 85% or 90% or 95% or 97% or 98% or 99% identical to a sequence set forth in any one of SEQ ID NO: 12 or amino acids 1-113 of any one of SEQ ID NOs: 45 to 48 or SEQ ID NO: 50, wherein the protein is capable of specifically binding to IL-23 but not significantly binding to an IL-12p40 subunit and not significantly binding to an IL-23p19 subunit when they are not components of IL-23. Alternatively, or additionally, the protein comprises a CDR (e.g., three CDRs) at least about 80% or 85% or 90% or 95% or 97% or 98% or 99% identical to CDR(s) of a $V_L$ as described herein according to any example, and capable of specifically binding to IL-23 but not significantly binding to an IL-12p40 subunit and not significantly binding to an IL-23p19 subunit when they are not components of IL-23.

For example, the inventors have produced a series of $V_L$ regions having variation at about 32% of residues. Thus, a protein can comprise a $V_L$ comprising a sequence at least about 68% identical to a $V_L$ sequence disclosed herein. In one example, the sequence is at least 85% or 95% identical.

The inventors have also produced a series of humanized $V_L$ regions having variation at about 14% of residues. Thus, a protein can comprise a $V_H$ comprising a sequence at least about 86% identical to a $V_H$ sequence disclosed herein. In one example, the sequence is at least 90% or 95% identical.

In another example, a nucleic acid of the disclosure comprises a sequence at least about 80% or 85% or 90% or 95% or 97% or 98% or 99% identical to a sequence set forth in any one of SEQ ID NOs: 11, 18, 72 to 75 or 77. The present disclosure also encompasses nucleic acids encoding a protein comprising a sequence set forth in any one of SEQ ID NO: 12, 27, 29 or amino acids 1-113 of any one of SEQ ID NOs: 45 to 48 or SEQ ID NO: 50, which differs from a sequence exemplified herein as a result of degeneracy of the genetic code.

The % identity of a nucleic acid or polypeptide is determined by GAP (Needleman and Wunsch. *Mol. Biol.* 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. In one example, the two sequences are aligned over their entire length.

The present disclosure contemplates mutant forms of an IL-23-binding protein of the disclosure. For example, such a mutant protein comprises one or more conservative amino acid substitutions compared to a sequence set forth herein. In some examples, the IL-23-binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle *J. Mol. Biol.*, 157: 105-132, 1982 and hydrophylic indices are described in, e.g., U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the protein comprises 10 or fewer, e.g., 9 or 8 or 7 or 6 or 5 or 4 or 3 or 2 or 1 non-conservative amino acid substitutions.

A mutant form of a protein described herein according to any example retains the ability to specifically bind to IL-23 while not significantly binding to an IL-12p40 subunit and/or an IL-23p19 subunit when they are not components of IL-23. Methods for determining specific binding to IL-23 are described herein. For example, a labeled protein is brought into contact with immobilized IL-23 or IL-12p40 subunit or IL-23p19 subunit.

Following washing, bound label is detected. The labeled protein is also brought into contact with immobilized IL-23p19 and/or IL-12p40 and, following washing, bound label is detected. Detection of label bound to IL-23 but not to IL-23p19 or IL-12p40 indicates that the mutant protein retains the ability to specifically bind to IL-23. An optional additional step in the foregoing methods comprises detecting label bound to the IL-23p19 subunit or and/IL-12p40 subunit. If label is detected bound to IL-23 but not significantly bound to IL-12p40 and/or IL-23p19, the protein is considered to specifically bind to IL-23 while not significantly binding to an IL-12p40 subunit and/or an IL-23p19 subunit when they are not components of IL-23.

In one example, the mutation(s) occur within a FR of an IL-23-binding protein of the disclosure. In another example, the mutation(s) occur within a CDR of an IL-23-binding protein of the disclosure.

Exemplary methods for producing mutant forms of protein include:

mutagenesis of DNA (Thie et al., *Methods Mol. Biol.* 525: 309-22, 2009) or RNA (Kopsidas et al., *Immunol. Lett.* 107(2):163-8, 2006; WO1999/058661);

introducing a nucleic acid encoding the polypeptide into a mutator cell, e.g., XL-1Red, XL-mutS and XL-mutS-Kanr bacterial cells (Stratagene);

DNA shuffling, e.g., as disclosed in Stemmer, *Nature* 370: 389-91, 1994; and site directed mutagenesis, e.g., as described in Dieffenbach (ed) and Dveksler (ed) (In: PCR Primer: A Laboratory Manual, Cold Spring Harbor Laboratories, NY, 1995).

Exemplary methods for determining biological activity of the mutant proteins of the disclosure will be apparent to the skilled artisan and/or described herein. For example, methods for determining antigen binding, competitive inhibition of binding, affinity, association, dissociation and therapeutic efficacy are described herein.

In one example, a mutant protein is produced by or following affinity maturation.

Exemplary Proteins

Exemplary variable region containing proteins produced by the inventors and their encoding nucleic acids are described in Table 1.

TABLE 1

Sequences of proteins and encoding nucleic acids

|   | Antibody Name | Heavy chain amino acid SEQ ID NO | Variable heavy chain nucleotide SEQ ID NO | Light chain amino acid SEQ ID NO | Variable light chain nucleotide SEQ ID NO |
|---|---|---|---|---|---|
| 1 | E11E7Chimera | 20 | 6 | 21 | 11 |
| 2 | 8-22 | 33 | 60 | 46 | 73 |
| 3 | 21-4 | 31 | 58 | 45 | 72 |
| 4 | 9-22 | 34 | 61 | 46 | 73 |
| 5 | 16-12 | 35 | 62 | 47 | 74 |
| 6 | 20-4 | 30 | 57 | 45 | 72 |
| 7 | 6-22 | 32 | 59 | 46 | 73 |
| 8 | 8-23 | 33 | 60 | 48 | 75 |
| 9 | 9-23 | 34 | 61 | 48 | 75 |
| 10 | 6-23 | 32 | 59 | 48 | 75 |
| 11 | 1-4 | 36 | 63 | 45 | 72 |
| 12 | 13-12 | 37 | 64 | 47 | 74 |
| 13 | 7-22 | 38 | 65 | 46 | 73 |
| 14 | 11-22 | 39 | 66 | 46 | 73 |
| 15 | 18-4 | 40 | 67 | 45 | 72 |
| 16 | 5-22 | 41 | 67 | 46 | 73 |
| 17 | 10-22 | 42 | 69 | 46 | 73 |
| 18 | 14-12 | 43 | 70 | 47 | 74 |
| 19 | 7-23 | 38 | 65 | 48 | 75 |
| 20 | 11-23 | 39 | 66 | 48 | 75 |
| 21 | 15-12 | 44 | 71 | 47 | 74 |
| 22 | 5-23 | 41 | 68 | 48 | 75 |
| 23 | 10-23 | 42 | 69 | 48 | 75 |
| 24 | ST883/885 | 49[1] | 76 | 50[1] | 77 |

[1]variable region sequence only.

Methods for Producing Proteins

Recombinant Expression

As discussed herein, a nucleic acid encoding an IL-23-binding protein of the disclosure (and/or polypeptides included in such a protein) is introduced into an expression construct, such that it is operably linked to a promoter to thereby facilitate its expression. Methods for producing expression constructs, e.g., cloning into expression constructs/vectors are known in the art and/or described in Ausubel et al (In: Current Protocols in Molecular Biology. Wiley Interscience, ISBN 047 150338, 1987), and (Sambrook et al (In: Molecular Cloning: Molecular Cloning: A Laboratory Manual, Cold Spring Harbor Laboratories, New York, Third Edition 2001) and U.S. Pat. No. 7,270,969.

In one example, the IL-23-binding protein of the disclosure is expressed in a bacterial cell. Typical promoters suitable for expression in bacterial cells such as for example a bacterial cell selected from the group comprising *E. coli, Staphylococcus* sp, *Corynebacterium* sp., *Salmonella* sp., *Bacillus* sp., and *Pseudomonas* sp., include, but are not limited to a promoter such as lacz, Ipp, a temperature-sensitive ($_L$ or $_R$ promoters, T7, T3, SP6 or semi-artificial promoters such as the IPTG-inducible tac promoter or lacUV5 promoter.

In another example, the IL-23-binding protein is expressed in a yeast cell. Typical promoters suitable for expression in yeast cells such as, *Pichia pastoris, Saccharomyces cerevisiae* and *S. pombe*, include, but are not limited to promoters from the following genes ADH1, GAL1, GAL4, CUP1, PHO5, nmt, RPR1, or TEF1.

In a further example, the IL-23-binding protein is expressed in an insect cell. Typical promoters suitable for expression in insect cells, or in insects, include, but are not limited to, the OPEI2 promoter, the insect actin promoter isolated from *Bombyx* muri, the *Drosophila* sp. dsh promoter (Marsh et al *Hum. Mol. Genet.* 9, 13-25, 2000).

An IL-23-binding protein of the disclosure can also be expressed in plant cells. Promoters for expressing peptides in plant cells are known in the art, and include, but are not limited to, the *Hordeum vulgare* amylase gene promoter, the cauliflower mosaic virus 35S promoter, the nopaline synthase (NOS) gene promoter, and the auxin inducible plant promoters P1 and P2.

In one example, an IL-23-binding protein of the disclosure is expressed in a mammalian cell or in a mammal. Typical promoters suitable for expression in a mammalian cell include, for example a promoter selected from the group consisting of, retroviral LTR elements, the SV40 early promoter, the SV40 late promoter, the CMV IE (cytomegalovirus immediate early) promoter, the $EF_1$ (promoter (from human elongation factor 1), the EM7 promoter, the UbC promoter (from human ubiquitin C). Examples of useful mammalian host cell lines include monkey kidney CV1 line transformed by SV40 (COS-7); human embryonic kidney line (HEK-293 cells); baby hamster kidney cells (BHK); Chinese hamster ovary cells (CHO); African green monkey kidney cells (VERO-76); or myeloma cells (e.g., NS/0 cells). In one example, the cells are CHO cells.

Other elements of expression constructs/vectors are known in the art and include, for example, enhancers, transcriptional terminators, polyadenylation sequences, nucleic acids encoding selectable or detectable markers and origins of replication.

In one example, an expression construct is a bicistronic expression construct. By "bicistronic" is meant a single nucleic acid molecule that is capable of encoding two distinct polypeptides from different regions of the nucleic acid, for example, a single nucleic acid capable of encoding a $V_H$ containing polypeptide and a $V_L$ containing polypeptide as distinct polypeptides. Generally, the regions encoding each distinct polypeptide are separated by an internal ribosome entry site (IRES) and the region 5' of the IRES does not comprise a transcription termination sequence. Exemplary IRESs are described, for example, in US20090247455.

Following production of a suitable expression construct, it is introduced into a suitable cell using any method known in the art. Exemplary methods include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

The cells used to produce the IL-23-binding protein of this disclosure are then cultured under conditions known in the art to produce an IL-23-binding protein of the disclosure.

Cell free expression systems are also contemplated by the present disclosure, e.g., the TNT T7 and TNT T3 systems (Promega), the pEXP1-DEST and pEXP2-DEST vectors (Invitrogen).

Protein Purification

Following production/expression, an IL-23-binding protein of the disclosure is purified using a method known in the art. Such purification generally provides the IL-23-binding protein of the disclosure substantially free of nonspecific protein, acids, lipids, carbohydrates, and the like. For example, the IL-23-binding protein will be in a preparation wherein more than about 90% (e.g. 95%, 98% or 99%) of the protein in the preparation is an IL-23-binding protein of the disclosure.

Standard methods of peptide purification are employed to obtain an isolated protein of the disclosure, including but not limited to various high-pressure (or performance) liquid chromatography (HPLC) and non-HPLC polypeptide isolation protocols, such as size exclusion chromatography, ion exchange chromatography, phase separation methods, electrophoretic separations, precipitation methods, salting in/out methods, immunochromatography, and/or other methods.

Alternatively, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) may be immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a protein comprising a Fc region of an antibody, protein A or protein G or modified fours thereof can be used for affinity purification. Protein A is useful for isolating purified proteins comprising a human γ1, γ2, or γ4 heavy chain Fc region. Protein G is recommended for all mouse Fc isotypes and for human γ3.

Conjugates

The present disclosure also provides an IL-23-binding protein of the disclosure conjugated to another compound, e.g., a conjugate (or immunoconjugate). The other compound can be directly or indirectly bound to the IL-23-binding protein (e.g., can comprise a linker in the case of indirect binding). The compound can be covalently or non-covalently linked to the IL-23-binding protein. Examples of compounds include, a radioisotope (e.g., iodine-131, yttrium-90 or indium-111), a detectable label (e.g., a fluorophore or a fluorescent nanocrystal), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), a compound that increases the half life of the protein in a subject (e.g., polyethylene glycol or other water soluble polymer having this activity) and mixtures thereof. Exemplary compounds that can be conjugated to an IL-23-binding protein of the disclosure and methods for such conjugation are known in the art and described, for example, in WO2010/059821.

Anti-Idiotype Antibodies

In addition to the IL-23-binding proteins of the disclosure that bind specifically to IL-23, the present disclosure also provides an anti-idiotypic (anti-Id) antibody specific for the protein of the disclosure. An anti-Id antibody is an antibody that recognizes unique determinants generally associated with the antigen-binding domain of an IL-23-binding protein of the disclosure. The anti-Id can be prepared by immunizing an animal with the protein of the disclosure or antigen binding domain thereof. The immunized animal will recognize and respond to the idiotypic determinants of the immunizing protein and produce an anti-Id antibody. The anti-Id antibody may also be used as an "immunogen" to induce an immune response in yet another animal, producing a so-called anti-anti-Id antibody.

Screening Assays

Proteins comprising antibody variable regions of the disclosure are readily screened for biological activity, e.g., as described below.

Binding Assays

One form of such an assay is an antigen binding assay, e.g., as described in Scopes (In: Protein purification: principles and practice, Third Edition, Springer Verlag, 1994). Such a method generally involves labeling the IL-23-binding protein and contacting it with immobilized antigen. Following washing to remove non-specific bound protein, the amount of label and, as a consequence, bound protein is detected. Of course, the IL-23-binding protein can be immobilized and the antigen labeled. Panning-type assays, e.g., as described or exemplified herein can also be used.

Neutralization Assays

An exemplary in vitro method for determining the effect (or neutralization activity) of an IL-23-binding protein of the disclosure is to contact IL-23 to a population of cells comprising immune cells upon which the IL-23 acts in the presence or absence of an IL-23-binding protein of the disclosure. Cell proliferation is then measured using a standard method, e.g., $^{13}$H thymidine incorporation or 5,6-carboxy fluorescein diacetate succinimidyl ester (CFSE) labeling and/or cytokine secretion. An increase or decrease in cell proliferation and/or cytokine secretion compared to a sample incubated in the absence of the protein indicates that the IL-23-binding protein modulates IL-23 activity. Such a method is exemplified herein.

Another method for determining the ability of an IL-23-binding protein of the disclosure to neutralize IL-23 activity is a receptor binding assay. In such a method, an IL-23 receptor or cell expressing same is immobilized. Labeled IL-23 (e.g., between 50 ng/ml and 150 ng/ml, such as 100 ng/ml) is then contacted to the immobilized receptor or cell in the presence or absence of a test protein and the amount of bound label detected. The IL-23-binding protein and the IL-23 can be contacted with one another prior to contacting the receptor or can be contacted to the receptor substantially simultaneously. A reduction in the amount of bound label in the presence of the IL-23-binding protein compared to in the absence of the protein indicates that the protein reduces or prevents binding of IL-23 to IL-23R.

By testing multiple concentrations of the IL-23-binding protein an $IC_{50}$ is determined, i.e., a concentration of the protein that reduces the amount of IL-23 that binds to IL-23R. In one example, the $IC_{50}$ is about 1 nM or less, such as 750 pM or less, for example, 500 pM or less. For example, the $IC_{50}$ is 400 pM or less. In one example, the $IC_{50}$ is between about 1 pM and 500 pM, for example, between about 50 pM and 450 pM. For example, the $IC_{50}$ is between about 100 pM and 400 pM, for example, between about 150 pM and 400 pM.

Similarly, an $EC_{50}$ can be determined, i.e., a concentration of the protein that achieves 50% of the maximum inhibition of binding of IL-23 to IL-23R achieved by the protein. In one example, the $EC_{50}$ is 1 nM or less, for example, 750 pM or less, for example, 500 pM or less, such as 400 pM or less. In one example, the $EC_{50}$ is about 300 pM or less. For example, the $EC_{50}$ is about 260 pM.

Another method for determining the ability of an IL-23-binding protein of the disclosure to neutralize IL-23 activity is to contact splenocytes with IL-23 in the presence or absence of the IL-23-binding protein and to detect secretion of a cytokine, such as, IL-17. A lower level of the cytokine in the presence of the protein compared to in the absence of the protein indicates that the protein neutralizes IL-23 activity. By testing multiple concentrations of the protein an $IC_{50}$ is determined, i.e., a concentration at which 50% of the maximum inhibition of cytokine secretion occurs.

By testing multiple concentrations of the IL-23-binding protein an $IC_{50}$ is determined, i.e., a concentration of the protein that reduces the amount of cytokine (e.g., IL-17) secreted. In one example, the $IC_{50}$ is about 1 nM or less, such as 900 pM or less, for example, 800 pM or less. For example, the $IC_{50}$ is 700 pM or less. In one example, the $IC_{50}$ is between about 1 pM and 800 pM, for example, between about 50 pM and 700 pM. For example, the $IC_{50}$ is between about 100 pM and 700 pM, for example, between about 120 pM and 680 pM.

Similarly, an $EC_{50}$ can be determined, i.e., a concentration of the protein that achieves 50% of the maximum inhibition of cytokine (e.g., IL-17) secretion achieved by the protein. In one example, the $EC_{50}$ is 1 nM or less, for example, 500 pM or less, such as 400 pM or less. In one example, the $EC_{50}$ is about 300 pM or less. For example, the $EC_{50}$ is about 290 pM.

Cell Killing Assays

In another example, the ability of an IL-23-binding protein of the disclosure (e.g., linked to a toxic compound or a constant region) is assessed by determining their ability to induce death of a cell. In the case of a Fc linked protein it is desirable to perform such an assay in the presence of immune effector cells and/or complement (e.g., to facilitate ADCC/CDC).

In Vivo Therapeutic Efficacy Assays

In another example, the activity of an IL-23-binding protein of the disclosure is determined by administering the IL-23-binding protein to an animal model. For example, the IL-23-binding protein is administered to NOD mice to test its ability to suppress, prevent, treat or delay diabetes (e.g., as described in Tang et al., *J. Exp. Med.,* 199: 1455-1465, 2004) and/or to a mouse model of GVHD (e.g., as described in Trenado et al., *J. Clin. Invest.,* 112: 1688-1696, 2002) and/or to a mouse model of psoriasis (e.g., Wang et al., *J Clin Invest.* 118(7): 2629-2639, 2008) and/or to a model of rheumatoid arthritis e.g., a SKG strain of mouse (Sakaguchi et al., Nature, 426: 454-460, 1995), rat type II collagen arthritis model, mouse type II collagen arthritis model or antigen induced arthritis models in several species (Bendele *J Musculoskel Neuron Interact;* 1(4):377-385, 2001) and/or a model of multiple sclerosis (for example, experimental autoimmune encephalomyelitis (EAE) and/or inflammatory airway disease (for example, OVA challenge or cockroach antigen challenge).

In one example, the activity of an IL-23-binding protein of the disclosure is determined in an IL-23-induced animal model of psoriasis, e.g., as exemplified herein. For example, a non-human mammal (e.g., a mouse) is administered IL-23 subcutaneously such that a localized inflammatory response is induced. Proteins are tested for their ability to prevent or treat the inflammatory response by administering before or after administration of IL-23. Animals are then assessed for erythema and/or induration and/or skin samples are collected from each mouse and fixed for histological assessment.

Competitive Binding Assays

Assays for determining a protein that competitively inhibits binding of an antibody of the disclosure will be apparent to the skilled artisan. For example, the antibody of the disclosure is conjugated to a detectable label, e.g., a fluorescent label or a radioactive label. The labeled antibody and the test protein are then mixed and contacted with IL-23 or an epitope thereof. The level of labeled antibody is then determined and compared to the level determined when the labeled antibody is contacted with the IL-23 or epitope in the absence of the protein. If the level of labeled antibody is reduced in the presence of the test protein compared to the absence of the protein, the protein competitively inhibits binding of the antibody.

Optionally, the test protein is conjugated to a different label than the antibody. This permits detection of the level of binding of the test protein to the protein or epitope.

In another example, the test protein is permitted to bind to IL-23 or a region thereof prior to contacting the IL-23 with an antibody described herein. A reduction in the amount of bound antibody in the presence of the protein compared to in the absence of the protein indicates that the protein competitively inhibits binding of the antibody to IL-23. A reciprocal assay can also be performed using labeled protein and first allowing the antibody to bind to IL-23. In this case, a reduced amount of labeled protein bound to IL-23 in the presence of the antibody compared to in the absence of antibody indicates that the protein competitively inhibits binding of the antibody to IL-23.

Epitope Mapping Assays

In another example, the epitope bound by a protein described herein is mapped. Epitope mapping methods will be apparent to the skilled artisan. For example, a series of overlapping peptides spanning the IL-23 sequence or a region thereof comprising an epitope of interest, e.g., peptides comprising 10-15 amino acids are produced. The IL-23-binding protein is then contacted to each peptide or a combination thereof and the peptide(s) to which it binds determined. This permits determination of peptide(s) comprising the epitope to which the IL-23-binding protein binds. If multiple non-contiguous peptides are bound by the protein, the protein may bind a conformational epitope.

Alternatively, or in addition, amino acid residues within IL-23 are mutated, e.g., by alanine scanning mutagenesis, and mutations that reduce or prevent protein binding are determined. Any mutation that reduces or prevents binding of the IL-23-binding protein is likely to be within the epitope bound by the protein.

A further method involves binding IL-23 or a region thereof to an immobilized protein of the present disclosure and digesting the resulting complex with proteases. Peptide that remains bound to the immobilized protein are then isolated and analyzed, e.g., using mass spectrometry, to determine their sequence.

A further method involves converting hydrogens in IL-23 or a region thereof to deuterium atoms and binding the resulting protein to an immobilized protein of the present disclosure. The deuterium atoms are then converted back to hydrogen, the IL-23 or region thereof isolated, digested with enzymes and analyzed, e.g., using mass spectrometry to identify those regions comprising deuterium, which would have been protected from conversion to hydrogen by the binding of a protein described herein. A form of this method is exemplified herein.

Affinity Assays

Optionally, the dissociation constant (Kd) or association constant (Ka) or affinity constant ($K_D$) of a protein for IL-23 or an epitope thereof is determined. These constants for a IL-23-binding protein is in one example measured by a radio-labeled or fluorescently-labeled IL-23-binding assay. This assay equilibrates the protein with a minimal concentration of labeled IL-23 in the presence of a titration series of unlabeled IL-23. Following washing to remove unbound IL-23, the amount of label is determined.

Affinity measurements can be determined by standard methodology for antibody reactions, for example, immunoassays, surface plasmon resonance (SPR) (Rich and Myszka *Curr. Opin. Biotechnol* 11: 54, 2000; Englebienne *Analyst.* 123: 1599, 1998), isothermal titration calorimetry (ITC) or other kinetic interaction assays known in the art.

In one example, the constants are measured by using surface plasmon resonance assays, e.g., using BIAcore surface plasmon resonance (BIAcore, Inc., Piscataway, N.J.) with immobilized IL-23 or a region thereof. Exemplary SPR methods are described in U.S. Pat. No. 7,229,619.

Half Life Assays

Some proteins encompassed by the present disclosure have an improved half-life, e.g., are modified to extend their half-life compared to proteins that are unmodified. Methods for determining a protein with an improved half-life will be apparent to the skilled person. For example, the ability of a protein to bind to a neonatal Fc receptor (FcRn) is assessed. In this regard, increased binding affinity for FcRn increased the serum half-life of the molecule (see for example, Kim et al., *Eur J. Immunol.*, 24:2429, 1994).

The half-life of an IL-23-binding protein of the disclosure can also be measured by pharmacokinetic studies, e.g., according to the method described by Kim et al, *Eur J of Immunol* 24:542, 1994. According to this method radiolabeled protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Stability Assays

Stability of an IL-23-binding protein of the disclosure can be assessed by any of a variety of assays. For example, the protein is exposed to a condition, e.g., heat or acid or stored for a period of time (e.g., 1 month) at room temperature. Aggregation of the protein can then be assessed by determining turbidity (with an increase in turbidity following exposure to the condition indicating instability), size exclusion chromatography, non-reducing gel electrophoresis or a binding or neutralization study described herein.

Pharmaceutical Compositions

The IL-23-binding protein of the present disclosure or nucleic acid encoding same or cell expressing same (syn. active ingredient) is useful for parenteral, topical, oral, or local administration, aerosol administration, or transdermal administration, for prophylactic or for therapeutic treatment. In one example, the IL-23-binding protein of the present disclosure or nucleic acid encoding same or cell expressing same is for parenteral administration, such as intravenous or subcutaneous administration.

Formulation of a protein or nucleic acid encoding same or cell expressing same to be administered will vary according to the route of administration and formulation (e.g., solution, emulsion, capsule) selected. An appropriate pharmaceutical composition comprising protein or nucleic acid encoding same or cell expressing same to be administered can be prepared in a physiologically acceptable carrier. A mixture of proteins can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The IL-23-binding protein of this disclosure can be lyophilized for storage and reconstituted in a suitable carrier prior to use according to art-known lyophilization and reconstitution techniques.

The optimum concentration of the active ingredient(s) in the chosen medium can be determined empirically, according to procedures well known to the skilled artisan, and will depend on the ultimate pharmaceutical formulation desired.

The dosage ranges for the administration of the IL-23-binding protein of the disclosure are those large enough to produce the desired effect. For example, the composition comprises a therapeutically or prophylactically effective amount of the IL-23-binding protein or nucleic acid encoding same or cell expressing same.

As used herein, the term "effective amount" shall be taken to mean a sufficient quantity of the IL-23-binding protein, nucleic acid or cells to induce/increase or inhibit/reduce/prevent signaling of IL-23 in a subject. The skilled artisan will be aware that such an amount will vary depending on, for example, the protein, nucleic acid or cells and/or the particular subject and/or the type or severity of a condition being treated. Accordingly, this term is not to be construed to limit the disclosure to a specific quantity, e.g., weight or number of proteins, nucleic acids or cells.

As used herein, the term "therapeutically effective amount" shall be taken to mean a sufficient quantity of protein, nucleic acid or cells to reduce or inhibit one or more symptoms of a condition.

As used herein, the term "prophylactically effective amount" shall be taken to mean a sufficient quantity of protein, nucleic acid or cells to prevent or inhibit or delay the onset of one or more detectable symptoms of a condition.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

One or more proteins of the present disclosure can be administered to an individual by an appropriate route, either alone or in combination with (before, simultaneous with, or after) another drug or agent. For example, the IL-23-binding protein of the present disclosure can also be used in combination with proteins, e.g., a TNF antagonist, an anti-IL-12/23 antibody, an anti-inflammatory or a painkiller. The IL-23-binding protein of the present disclosure can be used as separately administered compositions given in conjunction with antibiotics and/or antimicrobial agents. It will be appreciated by those skilled in the art that the IL-23-binding proteins of the present disclosure may be introduced into a subject by administering an expression construct of the disclosure or a cell expressing an IL-23-binding protein of the disclosure. A variety of methods can be used for introducing a nucleic acid encoding the antibody into a target cell in vivo. For example, the naked nucleic acid may be injected at the target site, may be encapsulated into liposomes, or may be introduced by way of a viral vector.

Diagnostic Assays

The following assays can be performed with an IL-23-binding protein of the disclosure.

An immunoassay is an exemplary assay format for diagnosing a condition in a subject or detecting IL-23 in a sample. The present disclosure contemplates any form of immunoassay, including Western blotting, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, and fluorescence activated cell sorting (FACS)-based assays.

One form of a suitable immunoassay is, for example, an ELISA or FLISA.

In one form such an assay involves immobilizing an IL-23-binding protein of the disclosure onto a solid matrix, such as, for example a polystyrene or polycarbonate microwell or dipstick, a membrane, or a glass support (e.g. a glass slide). A test sample is then brought into direct contact with the IL-23-binding protein and any antigen in the sample is bound or captured. Following washing to remove any unbound protein in the sample, a protein that binds to IL-23 at a distinct epitope (e.g., binds to IL-23p19 or IL-12p40) is brought into direct contact with the captured antigen. This detector protein is generally labeled with a detectable reporter molecule, such as for example, an enzyme (e.g. horseradish peroxidase (HRP)), alkaline phosphatase (AP) or (3-galactosidase. Alternatively, a second labeled protein can be used that binds to the detector protein. Following washing to remove any unbound protein the detectable marker is detected by the addition of a substrate, such as for example hydrogen peroxide, TMB, or toluidine, or 5-bromo-4-chloro-3-indol-beta-D-galaotopyranoside (x-gal). Of course, the immobilized (capture) protein and the detector protein may be used in the opposite manner.

The level of the antigen in the sample is then determined using a standard curve that has been produced using known quantities of the marker or by comparison to a control sample.

In the case of FLISA, a fluorescent label is used to determine the level of a labeled protein in a sample rather than an enzyme.

The assays described above are readily modified to use chemiluminescence or electrochemiluminescence as the basis for detection.

As will be apparent to the skilled artisan, other detection methods based on an immunosorbent assay are useful in the performance of the present disclosure. For example, an immunosorbent method based on the description supra using a radiolabel for detection, or a gold label (e.g. colloidal gold) for detection, or a liposome, for example, encapsulating NAD+ for detection or an acridinium linked immunosorbent assay.

In some examples of the disclosure, the level of IL-23 is determined using a surface plasmon resonance detector (e.g., BIAcore™, GE Healthcare, Piscataway, N.J.), a flow through device, for example, as described in U.S. Pat. No. 7,205,159; a micro- or nano-immunoassay device (e.g., as described in US20030124619); a lateral flow devices (e.g., as described in US20040228761 or US20040265926); a fluorescence polarization immunoassay (FPIA e.g., as described in U.S. Pat. Nos. 4,593,089 or 4,751,190); or an immunoturbidimetric assay (e.g., as described in U.S. Pat. Nos. 5,571,728 or 6,248,597.

Imaging Methods

As will be apparent to the skilled artisan from the foregoing, the present disclosure also contemplates imaging methods using an IL-23-binding protein of the disclosure. For imaging, a protein is generally conjugated to a detectable label, which can be any molecule or agent that can emit a signal that is detectable by imaging. However, a secondary labeled compound that specifically binds to an IL-23-binding protein of the disclosure may also be used. Exemplary detectable labels include a protein, a radioisotope, a fluorophore, a visible light emitting fluorophore, infrared light emitting fluorophore, a metal, a ferromagnetic substance, an electromagnetic emitting substance a substance with a specific magnetic resonance (MR) spectroscopic signature, an X-ray absorbing or reflecting substance, or a sound altering substance.

The IL-23-binding protein of the disclosure (and, if used the labeled secondary compound) can be administered either systemically or locally to an organ, or tissue (or tumor, in the case of a cancer) to be imaged, prior to the imaging procedure. Generally, the IL-23-binding protein is administered in doses effective to achieve the desired optical image of a tumor, tissue, or organ. Such doses may vary widely, depending upon the particular protein employed, condition to be imaged, tissue, or organ subjected to the imaging procedure, the imaging equipment being used, and the like.

In some examples of the disclosure, the IL-23-binding protein is used as in vivo optical imaging agents of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like.

Examples of imaging methods include magnetic resonance imaging (MRI), MR spectroscopy, radiography, computerized tomography (CT), ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

In some examples, an imaging agent is tested using an in vitro or in vivo assay prior to use in humans, e.g., using a model described herein.

Samples and Control Samples

As will be apparent to the skilled artisan, some of the examples described herein require some degree of quantification to determine the level of IL-23. Such quantification may be determined by the inclusion of a suitable control sample in an assay of the disclosure.

In one example, a suitable control sample is a sample that is derived from a healthy subject or a normal subject.

In the present context, the term "healthy subject" shall be taken to mean an individual who is known not to suffer from a condition associated with IL-23, e.g., an inflammatory condition.

The term "normal subject" shall be taken to mean an individual having a normal level of IL-23 in a sample compared to a population of individuals.

The present disclosure also contemplates the control sample as being a data set obtained from a normal and/or healthy subject or a population of normal and/or healthy subjects.

In one example, a method of the disclosure additionally comprises determining the level of IL-23 in a control sample, e.g., using a method described herein.

In one example, a sample from the subject and a control sample are assayed at approximately or substantially the same time.

In one example, the sample from the subject and the control sample are assayed using the same method of the disclosure as described herein in any one or more embodiments to allow for comparison of results.

Conditions

Exemplary conditions which may be treated/prevented/diagnosed/prognosed by performing a method of the disclosure include inflammatory conditions, GVHD, infection and cancer.

Exemplary inflammatory conditions include inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tiibulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis. For example, the inflammatory condition is inflammatory arthritis, e.g., RA or juvenile chronic arthritis.

In another example, the inflammatory condition is an inflammatory neurological condition, e.g., a myelin associated condition, e.g., multiple sclerosis.

In another example, the inflammatory condition is an inflammatory skin disease (e.g., an autoimmune or immune-mediated skin disease), e.g., a bullous skin diseases, erythema multiforme, contact dermatitis. Alternatively, the skin disease is psoriasis.

In another example, the inflammatory condition is an inflammatory mucosal condition, e.g., an inflammatory disease of the bowel (e.g., inflammatory bowel disease, Crohn's disease or ulcerative colitis), or an inflammatory disease of the lung (e.g., airway hyperreactivity or asthma).

In one example, a condition is a $T_H17$ cell-mediated condition. As used herein, the term "$T_H17$ cell-mediated condition" shall be taken to mean any condition characterized or caused by excessive numbers or activity of $T_H17$ cells. The skilled artisan will be aware that a $T_H17$ cell is a CD4$^+$ T cell that expresses IL-17. Exemplary $T_H17$ cell-mediated conditions include autoimmune/inflammatory conditions (e.g., psoriasis, inflammatory bowel disease, arthritis (e.g., rheumatoid arthritis), multiple sclerosis and inflammatory bowel disease (e.g., Crohn's disease)) and graft versus host disease.

In one example, a condition is psoriasis.

In another example, a condition is Crohn's disease.

In a further example, a condition in multiple sclerosis.

In one example, the multiple sclerosis is relapsing-remitting multiple sclerosis, and the IL-23-binding protein or antibody is administered while the condition is in remission to there by prevent a relapse.

Kits

The present disclosure additionally comprises a kit comprising one or more of the following:
(i) an IL-23-binding protein of the disclosure or expression construct(s) encoding same;
(ii) a cell of the disclosure; or
(iii) a pharmaceutical composition of the disclosure.

In the case of a kit for detecting IL-23, the kit can additionally comprise a detection means, e.g., linked to an IL-23-binding protein of the disclosure.

In the case of a kit for therapeutic/prophylactic use, the kit can additionally comprise a pharmaceutically acceptable carrier or diluent.

Optionally a kit of the disclosure is packaged with instructions for use in a method described herein according to any embodiment.

The present disclosure is described further in the following non-limiting Examples.

General Methods

HEK293/pTT5 Expression System

For all transfections involving the HEK293E/pTT5 expression system, HEK293E cells were cultured in complete cell growth media (1 L of F17 medium (Invitrogen™), 9 ml of Pluronic F68 (Invitrogen™), 2 mM Glutamine containing 20% (w/v) Tryptone NI (Organotechnie™) with Geneticin (50 mg/ml, Invitrogen™) at 50 μl/100 ml culture). Briefly, the day before transfection cells were harvested by centrifugation and resuspended in fresh media without Geneticin. The following day cells were transfected by dropwise addition of a transfection mixture comprising DNA and FuGENE (Roche) according to manufacturer's directions. Transfected cultures were incubated overnight at 37° C., 5% $CO_2$ with gentle shaking (120 rpm) prior to the addition of Tryptone and Geneticin (12.5 mL and 250 uL per 500 mL of culture volume respectively). The following day 12.5 ml of Tryptone and 250 μl of Geneticin were added per 500 ml culture. The culture was incubated at 37° C., 5% $CO_2$ and 120 rpm for seven days, then the supernatants were harvested and purified.

IL-23 Protein

Human IL-23 (comprising of IL-12p40 (SEQ ID NO: 1) covalently linked to IL-23p19 (SEQ ID NO: 2) was purchased (Ebiosciences or RnD Systems). Alternatively, IL-23, IL-12p40 and IL-23p19 were produced in the mammalian HEK293E/pTT5 expression system through transfection of DNA expression constructs as described previously. The following proteins were produced:

TABLE 2

List of IL-23 proteins used in these experiments.

| Name | Subunit A (SEQ ID) | TAG A (SEQ ID) | Subunit B (SEQ ID) | TAG B (SEQ ID) |
|---|---|---|---|---|
| IL-23Fc | p40 (SEQ ID NO: 1) | human Fc (SEQ ID NO: 16) | p19 (SEQ ID NO: 2) | FLAG (SEQ ID NO: 17) |
| IL-23His | p40-linker-p19 (SEQ ID NO:78) | HIS (SEQ ID NO: 79) | N/A | N/A |
| IL-23AviHis | p40 (SEQ ID NO: 1) | None | p19 (SEQ ID NO: 2) | AviTag&HIS (SEQ ID NO: 80) |
| IL-12p40Fc | p40 (SEQ ID NO: 1) | human Fc (SEQ ID NO: 16) | N/A | N/A |
| IL-12p19Fc | p19 (SEQ ID NO: 2) | human Fc (SEQ ID NO: 16) | | |

Culture supernatants containing the secreted proteins were harvested by centrifugation at 2000×g for 10 mins to remove the cells. Proteins containing a HIS Tag were purified from the supernatant via the $His_8$ affinity tag using a HisTrap™ HP column (GE Healthcare). Proteins containing a Fc region were purified using Protein A chromatography as described below for the purification of antibodies. Eluted proteins were buffer-exchanged into PBS using a concentrator (Amicon) or via desalting or via size-exclusion chromatography.

For phage display the Avitag™ sequence of the recombinant human IL-23AviHIS was biotinylated using the enzyme BirA. This resulted in specific biotinylation at a single amine containing amino acid in the AviTag sequence. Free biotin was removed from the protein preparation either by dialysis against PBS using a Slide-A-Lyzer dialysis cassette (Pierce) with a 3.5 kDa molecular weight cut-off or a desalting column (GE Healthcare).

Construction of Vectors Expressing Antibodies

Heavy chain variable region ($V_H$) amino acid sequences were formatted in silico onto a human IgG1 constant region comprising $C_H1$, hinge, $C_H2$ and $C_H3$ domains (see for example NCBI accession number P01857.1). Similarly, light chain variable region sequences were formatted in silico onto either a human kappa or lambda constant region (see for example NCBI accession numbers AAI10395 (kappa) and AAI07853 (lambda)) according to the isotype of the parental variable region. Amino acid sequences were subsequently back-translated into DNA sequences (GeneArt, Germany). The resulting genes were synthesized de novo by assembly of synthetic oligonucleotides (GeneArt, Germany). Heavy and light-chain genes were subsequently cloned into variants of the expression vector pTT5 (Durocher et al., Nucleic Acids Research 30, E9, 2002) containing either a heavy- or a light-chain leader sequence, respectively (SEQ ID NOs: 81 and 82, respectively).

Expression and Purification of Antibodies

Antibodies were produced through co-transfection of heavy- and light-chain containing pTT5 plasmids into the cell line HEK293E using the transfection reagent FuGENE (Roche) as described above. After seven days supernatants were harvested by centrifugation and adjusted to pH 7.4 prior to loading onto a HiTrap™ Protein A column (5 ml, GE Healthcare). The column was washed with 50 ml of 1×PBS (pH 7.4). Elution was performed using 0.1M citric acid pH 2.5. The eluted antibody was desalted using Zeba Desalting columns (Pierce) into 1×PBS (pH 7.4). The antibodies were analyzed using SDS-PAGE. The concentration of the antibody was determined using a BCA assay kit (Pierce) according to manufacturer's instrcutions.

Detecting Binding of Antibodies to IL-23 by ELISA

A NuncMaxisorp 96-well plate was coated with human IL-23 diluted to 1 µs/ml in carbonate coating buffer and overnight incubation at 4° C. The plate was washed (three times in 1×PBS-Tween20 (0.05%)) then blocked for an hour with 1% BSA in PBS at room temperature. Biotinylated antibody was prepared starting from 10 µg/ml and serial half log dilutions were performed then 100 µl was added to the plate and incubated for an hour. The plate was washed and Streptavidin-HRP at 1:2000 dilution was added to all wells and further incubated for an hour. The plate was washed and subsequently developed using TMB (Sigma). The color development reaction was stopped by addition of an equal volume of 1M HCl. Absorbance of the resulting reaction was determined using a plate-based spectrophotometer.

Surface Plasmon Resonance (SPR) Analysis of IL-23-binding Antibodies

Using a Biacore 3000, Protein A (Pierce) was immobilized on a CM5 chip using amine coupling chemistry to give 3000 Response Units (RU). Antibody was captured on the surface of the chip in flow cell 2 or 4 with a control surface in flow cell 1 or 3. Human IL-23 was then passed over both flow cells and the response units measured. The surface was then regenerated with 10 mM glycine pH 2.5. For a kinetic run this process was repeated with 5 dilutions of IL-23. Data was double referenced using an injection of running buffer before being fitted using a 1:1 Langmuir equation to determine ka, kd and $K_D$.

Antibody Inhibition of IL-23-Induced IL-17 Production in Murine Splenocytes

Spleens were obtained from C57BL/6 mice and prepared by first homogenizing the spleens followed by lysis of the red blood cells using $NH_4Cl$. The splenocytes were then washed in media (RPMI, 10% FBS, 2 mM L-Glutamine, 100U of Pen/Strep) by resuspension and centrifugation. The antibody was diluted in culture media sufficient to generate a titration curve across a 96-well plate. 100 ng/mL of human IL-23 (EBiosciences) was added to each well and incubated at 37° C. with 5% $CO_2$ humidity for 1 hour. The cells were added to the wells giving a cell concentration of $5\times10^6$ cells/mL in a total volume of 200 µl/well. Cultures were incubated at 37° C. with 5% $CO_2$ with humidity for 4 days. The supernatants were harvested at the end of incubation and a Duoset ELISA murine IL-17 kit (R&D Systems) was used to detect murine IL-17 produced.

EXAMPLE 1

Production of Monoclonal Antibodies That Specifically Bind IL-23

Hybridoma Generation

Monoclonal antibodies against heterodimeric IL-23 were generated by genetic immunization with corresponding conventional protein immunization of rats. For genetic immunization, the DNA sequence for human IL-23 (containing a GS linker to facilitate the expression of the molecule from one promoter; SEQ ID NO: 5) was cloned into a plasmid for genetic immunization using restriction enzyme technology. The resulting plasmids allow the secretion of soluble IL-23 tagged by a c-myc epitope at the N- or C-terminus. The c-myc epitope was utilized to confirm expression of the soluble IL-23.

Rats were then immunized six times with the plasmid using a Helios gene gun (Bio-Rad, Germany) according to a published procedure (Kilpatrick et al., *Hybridoma* 17: 569-576, 1998). One week after the last application of the immunization plasmid each rat is boosted by intradermal injection of recombinant human IL-23 protein (Ebiosciences).

Four days later, the rats were killed and their lymphocytes fused with myeloma cells using polyethylene glycol (HybriMax™; Sigma-Aldrich, Germany), seeded at 100,000 cells per well in 96- well microtiter plates and grown in DMEM medium supplemented with 10% fetal bovine serum and HAT additive for hybridoma selection ((Kilpatrick et al., 1998, supra)).

Screening of Hybridoma for Antibody Specificity

Full-length native IL-23 (Ebioscience) was coated onto a 96-well plate (Maxisorp, Nunc). Hybridoma supernatant from each hybridoma was added to the IL-23 coated wells and bound antibody detected using secondary antibodies specific for murine (rat) antibodies with a HRP conjugate facilitating a color reaction. Hybridomas which displayed positive binding for IL-23 were subcloned via limiting dilution, in which cells were diluted in culture media and deposited into fresh 96-well plates at a ratio of less than 1 cell/well. After the clones recovered additional ELISAs were performed on the hybridoma supernatant.

Anti-FLAG M2 antibody (Sigma-Aldrich) was coated onto ELISA plates overnight. These plates were then used to capture individually: FLAG-tagged IL-23p19, FLAG-tagged IL-12p40 and FLAG-tagged IL-23. Hybridoma supernatant from the clones was added and hybridomas that were positive for binding to IL-23 but not IL-12p40 or IL-23p19 were expanded.

Identification and Molecular Characterization of Rat Antibody E11E7 with IL-23 Heterodimer Specificity Using the above method of immunization and screening one rat hybridoma out of approximately 83 hybridomas screened secreted an antibody that bound strongly to IL-23 but not significantly to IL-12p40 or IL-23p19. This antibody, termed E11E7 was sequenced by reverse transcriptase polymerase chain reaction using RNA isolated from E11E7-expressing hybridoma cells. Briefly, RNA was prepared using TRI reagent (Sigma) according to the manufacturer's protocol. cDNA synthesized from 100-200 ng RNA using the AccuScript® High Fidelity 1st Strand cDNA Synthesis Kit (Stratagene) was subsequently used as a template for PCR. Primers from the Novagen Mouse IgG Primer Set were used to amplify putative E11E7 heavy- and light-chain sequences from the cDNA using the polymerase UltraPfuII-HS essentially according to manufacturer's instructions (Stratagene).

Thermocycling was performed using an Eppendorf Mastercycler and the following cycling parameters:
(94° C. 2 min) 1 cycle; followed by;
(94° C. 30 sec, 60° C. 30 sec, 72° C. 45 sec) 30 cycles; followed by
(72° C. 5 min) 1 cycle Following electrophoresis on an agarose gel (0.7-1.0%), PCR products were excised and cleaned using the Qiaquick gel extraction kit (Qiagen). A-tailing was performed through incubation of Taq-polymerase (Invitrogen™) and dATP at 72° C. for 15 minutes. A-tailed PCR products were then ligated into pGEM-T Easy (Promega) and transformed into TOP10 competent cells (Invitrogen™) according to manufacturer's instructions. PCR screening of transformants using vector-specific primers identified clones possessing a plasmid containing an insert of ~500 bp. Plasmid DNA was subsequently isolated from insert-containing clones using a QIAprep spin miniprep kit (QIAgen) and sequenced (AGRF, Brisbane). The nucleotide sequences for the variable heavy (SEQ ID NO: 6) and variable light chains (SEQ ID NO: 11) were then translated into primary amino acid sequence (SEQ ID NO: 7 for $V_H$ and SEQ ID NO: 12 for $V_L$).

A rat-human chimeric antibody was generated through formatting the rat E11E7 heavy- and light-chain variable region amino acid sequences onto human constant regions. Genes were synthesized following back-translation and subsequently cloned into the expression vector pTT5 as described in the general methods. The nucleotide sequence of the $V_H$ comprises a sequence set forth in SEQ ID NO: 19. The nucleotide sequence of the $V_L$ comprises a sequence set forth in SEQ ID NO: 18. Amino acid sequences of these full length heavy- and light chains are given in SEQ ID NOs: 20 and 21, respectively.

Figure 1:
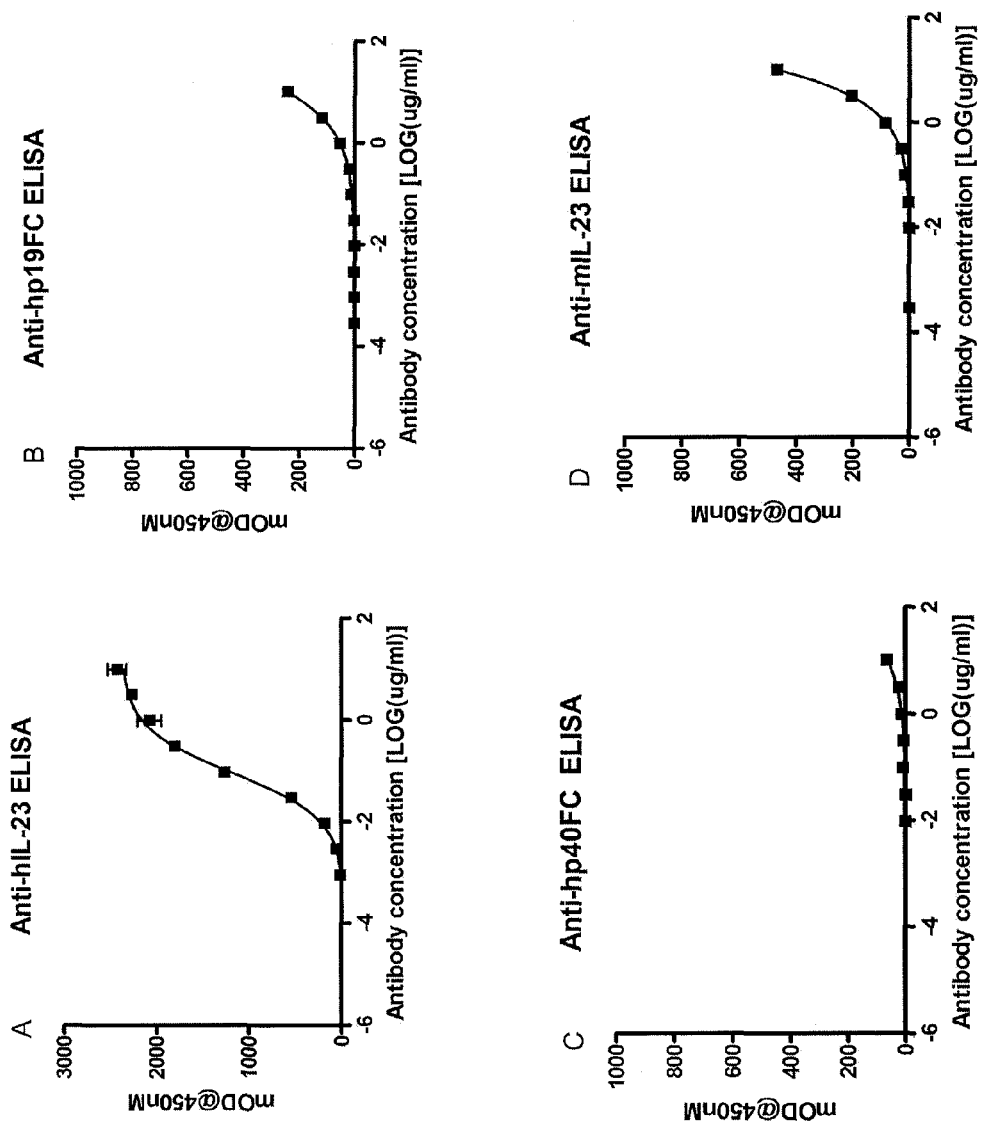
FIG. 1 comprises a series of graphical representations showing the specificity of chimeric antibody E11E7Chimera for IL-23. Panel A shows reactivity of E11E7Chimera for human IL-23. Panel B shows reactivity of E11E7Chimera for human IL-23p19-Fc fusion protein. Panel C shows reactivity of E11E7Chimera for human IL-12p40-Fc fusion protein. Panel D shows reactivity of E11E7Chimera for mouse IL-23.

E11E7Chimera was biotinylated (Pierce EZ-Link Sulfo-NHS) and screened for binding to IL-23Fc, IL-23p19Fc, IL-12p40Fc and murine IL-23 (Ebiosciences) using ELISA techniques described in the general methods. Biotinylated E11E7Chimera bound to IL-23 strongly and showed little to no binding to the individual subunits or to murine IL-23 (FIG. 1). This demonstrated that E11E7Chimera was specific for the human IL-23 complex but not the individual subunits.

Mapping of the Epitope of E11E7

Epitope mapping was performed on the E11E7Chimera to determine the location on IL-23 to which the antibody binds. Using hydrogen/deuterium exchange experiments (essentially as described in U.S. Pat. No. 06,797,482B2), critical regions on IL-23 involved in the binding to E11E7 were identified. Hydrogen was exchanged in solution for deuterium on IL-23. This deuterated IL-23 was then bound by a FAb fragment of E11E7Chimera in solution. The complex was exchanged back to hydrogen, except for the regions on IL-23 that were in contact with the antibody and therefore protected from exchange. The IL-23:Antibody complex was then digested and analyzed via mass spectroscopy to identify regions containing deuterium. The following results were obtained:

TABLE 3

Deuterium difference of IL-23 peptides before and after incubation with E11E7

| IL-12p40 | | | IL-23p19 | | |
|---|---|---|---|---|---|
| Sequence Start | Sequence End | % Deuterium Difference | Sequence Start | Sequence End | % Deuterium Difference |
| 3 | 9 | 8% | 17 | 23 | 13% |
| 3 | 12 | 7% | 17 | 24 | 11% |
| 12 | 23 | 6% | 26 | 37 | 17% |
| 15 | 23 | 4% | 27 | 37 | 13% |
| 26 | 54 | 7% | 40 | 68 | 18% |
| 29 | 54 | 9% | 40 | 69 | 19% |
| 29 | 80 | 5% | 71 | 80 | 1% |
| 57 | 80 | 6% | 72 | 81 | 5% |
| 62 | 80 | 4% | 81 | 88 | 6% |
| 83 | 90 | 9% | 83 | 88 | 6% |
| 85 | 90 | 5% | 91 | 105 | 17% |
| 93 | 109 | 6% | 91 | 109 | 25% |
| 112 | 121 | 9% | 112 | 115 | 13% |
| 112 | 122 | 5% | 112 | 140 | 36% |
| 124 | 125 | 5% | 112 | 144 | 32% |
| 128 | 132 | 12% | 115 | 140 | 36% |
| 131 | 132 | 8% | 143 | 144 | 11% |
| 135 | 150 | 12% | 143 | 153 | 5% |
| 135 | 153 | 12% | 145 | 153 | 6% |
| 156 | 170 | 8% | 155 | 170 | 5% |
| 158 | 170 | 9% | 160 | 170 | 12% |
| 173 | 187 | 5% | | | |
| 173 | 189 | 2% | | | |
| 187 | 189 | 1% | | | |
| 208 | 231 | 7% | | | |
| 208 | 233 | 8% | | | |
| 234 | 247 | 8% | | | |
| 236 | 246 | 11% | | | |
| 249 | 251 | 1% | | | |
| 250 | 251 | 2% | | | |
| 253 | 274 | 9% | | | |
| 254 | 274 | 2% | | | |
| 277 | 296 | 8% | | | |
| 278 | 296 | 7% | | | |
| 299 | 306 | 5% | | | |
| 302 | 306 | 6% | | | |

The sequences used for this analysis corresponds to SEQ ID NO: 1 for the IL-12p40 subunit and SEQ ID NO: 2 for the IL-23p19 subunit. For each individual subunit the mean±standard deviation (S.D.) % deuterium difference was calculated across 50% of the peptides with the lowest deuterium content. A value greater then the mean+3 S.D. was considered significantly. The mean (50%)+3 S.D. % deuterium difference across the p40 subunit was 10.2%. The mean (50%)+3 S.D. % deuterium difference across the p19 subunit was 18.1%. Overlapping peptides sequences in which the % deuterium difference was greater then the mean (50%)±3 S.D. are highlighted in bold in Table 3. These data demonstrates that residues on IL-12p40 and IL-23p19 were protected from deuterium exchange upon binding of E11E7Chimera.

Peptides with the highest deuterium content (p40: 135-153; p19: 112-144) were mapped on a crystal structure of IL-23 (FIG. 2). The FAb arm of an antibody having a diameter ~50 Angstroms (as measured across the crystal structure 3HMX) could well bind across the 25 Angstrom span between atoms within the highlighted regions of p40 and p19.

E11E7Chimera Inhibits IL-23-binding to IL-23R hIL23R-HIS was diluted to 1 µg/ml in carbonate coating buffer and added to each well of a 96 well plate and incubated at 4° C. overnight. The plate was then washed three times. The wells were then blocked by adding 200 µl of blocking buffer to each well and incubating the plate at 25° C. for 1 hour. E11E7Chimera or anti-p40 antibody was diluted in antibody diluent sufficient to generate a titration curve starting at 10

µg/ml. Biotinylated hIL-23 (E-bioscience) was diluted to 100 ng/ml final concentration in antibody diluent. hIL-23 was pre-incubated with the antibody in a deep well container for 2 hours. The plate was washed as previously described and wells subsequently incubated with the antibody/hIL-23 solution for 2 hours at 25° C. The plate was then washed as previously described and 100 µl of Streptavidin HRP (BD Phamingen) at 1:5000 in antibody diluent was used to detect bound biotinylated cytokine. After incubation at 25° C. for 1 hour the plate was washed again as previously described. 100 µl TMB substrate solution (Sigma-Aldrich) was added to each well and the color allowed to develop for 15 minutes. 100 µl of 1M HCl was added to stop the color development reaction and absorbance was determined at 450 nm (ref. 620 nm).

E11E7 was able to inhibit the binding of IL-23 to IL-23R when compared to the anti-p40 antibody which was unable to inhibit IL-23-binding to IL-23R at the highest concentration tested (FIG. 2).

E11E7 is a Potent Inhibitor and IL-23 Bioactivity In-Vitro

In SPR assays, the affinity of E11E7Chimera exceeded the sensitivity of the Biacore 3000 and has a $K_D$ less then 100 pM. E11E7 and its chimera, E11E7Chimera, were screened for their IL-23 neutralization ability using the murine splenocyte assay. Both antibodies displayed strong neutralization of human IL-23 induced murine IL-17 secretion (FIG. 4). These results demonstrate that an antibody that binds to the heterodimeric complex but not the individual subunits of IL-23 is a potent neutralizer of IL-23 bioactivity.

E11E7Chimera is Efficacious in the IL-23-Driven Murine Model of Psoriasis

Treatment of C57B1/6J mice with IL-23 intradermally to the back for 6 days induced a localized inflammatory response characterized by erythema and induration, with histological evidence of epidermal hyperplasia, parakeratosis, and localized inflammatory infiltrate. Antibodies were tested for their ability to decrease the inflammatory response at a single dose on the day before cytokine treatment commenced. One day before the start of cytokine injection they were given a single intraperitoneal injection of E11E7Chimera, a human p19 specific antibody (Antibody 7G10 from U.S. Pat. No. 7,807,160) or an isotype control antibody at a dose of 10 mg/kg. Mice were scored daily for erythema and induration in the test area. All treatments and observations were performed blinded. At the termination of the study, skin samples were collected from each mouse and fixed for histological processing and Haematoxylin and Eosin (H&E) staining by standard protocols.

Values for epidermal thickness were determined by printing off a paper copy of the lower power images of the sections of skin from each mouse. The skin section on each image was divided into four quadrants by the use of three vertical lines. The epidermal thickness was then measured at the point of intersection for the three lines used to delineate the quadrants, i.e. three thickness measurements per photograph. The actual distances in mm were then converted to microns using the scale on each image. In those instances where the measuring point intersected a region considered to be non-representative of epidermal thickness such as a hair follicle or sweat gland the location of the measuring point was adjusted to an adjacent section of skin. Measurements were done blinded by two independent observers.

Both groups that received E11E7Chimera and the Anti-p19 antibody had a reduced clinical score, from day 5 onwards, relative to an isotype control, demonstrating efficacy of the antibodies in this study (FIG. 5A). It was also observed that E11E7Chimera demonstrated improved efficacy over the Anti-p19 antibody from day 6 onwards.

E11E7Chimera and anti-p19 antibodies demonstrated a statistically significant decrease in epidermal thickness relative to the isotype control (FIG. 5B). Treatment with E11E7Chimera led to significantly lower epidermal thickness score then treatment with anti-p19 antibodies. This correlates well with the clinical scoring demonstrating that E11E7Chimera is a potent inhibitor of IL-23, more potent that the anti-p19 antibody, when tested in this murine psoriasis model.

Humanization of Rat Antibody E11E7

Parallel strategies of Superhumanisation™ (US 2003/0039649) and 3D modeling (Lo *Methods Mol Biol* 248: 135-159, 2004) were employed to select suitable human frameworks capable of supporting the CDRs of the rat E11E7 antibody.

Selection of Human Framework Acceptors Using 3D Modeling

Independent 3D models of the rat $V_H$ and $V_L$ were constructed using the database of crystal structures (Worldwide Protein Data Bank pdb), http://www.wwpdb.org) and software package Discovery Studio v3.0 (Accelrys®, USA). Briefly, the protein data bank database was interrogated by Basic Local Alignment Search Tool (BLAST) searches using either the rat heavy chain variable region or light chain variable region to identify antibodies of similar (>70% homology) polypeptide sequence with accompanying crystal structure information. These structures were subsequently used to build homology models based on the amino acid sequence homology shared by the rat variable regions and that of the identified crystal structures.

Rat $V_H$ and $V_L$ models were used to predict which framework region amino acids were likely to interact with amino acids in the CDRs and thus require preserving in the chosen human acceptors for optimal activity of the humanized antibodies. These models were also used to identify suitable human $V_H$ and $V_L$ acceptor frameworks from the protein data bank based on their framework structural homology with those of the rodent antibody. To ensure correct heavy- and light-chain pairing, $V_H$ and $V_L$ human acceptor frameworks of same antibody crystal structure were progressed through the humanization process. Human acceptor antibodies with better rodent-human heavy chain framework region structural homology were preferred over those with better rodent-human light chain framework homology. For the rat antibody E11E7 the selected human acceptor frameworks were pdb accession codes 3B2U, 3L5Y, 1U6A and 1QLR. Of the selected frameworks, 3L5Y and 1U6A were not progressed due to containing multiple amino acid residue changes verses the human germline sequences.

Superhumanisation™ of Rat E11E7

Briefly, canonical structures were assigned to rat E11E7 heavy- and light-chains through inspection of their respective amino acid sequences. E11E7 was assigned the canonical structure 3-1-1/1-1 ($V_L/V_H$). Human germline sequences sharing the same canonical structure were used as acceptor frameworks for the grafting of donor CDRs.

Humanization Data Summary

As a result of the humanization processes 22 humanized antibodies were produced and tested for their ability to bind human IL-23 (Table 4). Briefly, 2 mL transfections of the 22 humanized antibodies were screened for antibody expression level and binding activity via SPR. Protein A was immobilized onto FC1 and FC2 (or alternatively FC3 and FC4) of a CM5 research grade sensor chip using amine coupling, giving approximately 3000 RU. FC1 was used as a blank throughout the experiments. The experiments were run in HBS-P buffer (SPR). Antibody-containing cell culture supernatants were diluted in 10× HBS-P buffer at a ratio of 9:1. The diluted antibody was injected over FC2 at a flow rate of 20 µl/min. IL-23 (HEK293E-derived) was passed over the surface of FC1 and FC2 at a concentrations of 5 µg/ml as a kinetic injection with 5 min dissociation time across both FC. Regeneration of the surface was performed using 10 mM Glycine, pH 1.5. The sensorgram data from FC2 were subtracted from FC1 and a buffer only control. Antibodies that captured at a level greater than 50RU and had an IL23 capture/antibody capture ratio greater than 0.1 were scaled-up and purified for further testing.

The Sequence IDs of the variable heavy and light chains for each antibody are given in the Table 4 along with kd (off-rates) of selected tested antibodies.

TABLE 4

Humanized E11E7 based antibodies

| Antibody | Heavy Chain SEQ ID NO | Light Chain SEQ ID NO | SEQ ID kd (l/s) |
|---|---|---|---|
| E11E7Chimera | 20 | 21 | 5.98E−05 |
| 8-22 | 33 | 46 | 1.17E−04 |
| 21-4 | 31 | 45 | 1.91E−04 |
| 9-22 | 34 | 46 | 1.98E−04 |
| 16-12 | 35 | 47 | 2.24E−04 |
| 20-4 | 30 | 45 | 2.31E−04 |
| 6-22 | 32 | 46 | 2.41E−04 |
| 8-23 | 33 | 48 | 2.85E−04 |
| 9-23 | 34 | 48 | 5.60E−04 |
| 6-23 | 32 | 48 | 5.66E−04 |
| 1-4 | 36 | 45 | 6.16E−04 |
| 13-12 | 37 | 47 | 8.55E−04 |
| 7-22 | 38 | 46 | 1.02E−03 |
| 11-22 | 39 | 46 | 1.21E−03 |
| 18-4 | 40 | 45 | 1.33E−03 |
| 5-22 | 41 | 46 | 1.98E−03 |
| 10-22 | 42 | 46 | 3.13E−03 |
| 14-12 | 43 | 47 | 3.49E−03 |
| 7-23 | 38 | 48 | 3.91E−03 |
| 11-23 | 39 | 48 | 4.62E−03 |
| 15-12 | 44 | 47 | 6.00E−03 |
| 5-23 | 41 | 48 | 6.39E−03 |
| 10-23 | 42 | 48 | 0.013 |

All tested humanized antibodies demonstrated binding to IL-23 via surface plasmon resonance (Table 4). Antibodies 1-4, 6-22, 8-22, 20-4, 9-22 and 21-4 were tested for binding to IL-23 with ELISA (FIG. 6). All antibodies tested demonstrated binding to IL-23 similar to that of E11E7Chimera. These data confirm successful retention of binding activity in the humanized E11E7 antibodies.

Sequences of humanized antibodies and E11E7 $V_D$ and $V_L$ are shown in FIG. 7. This figure also shows regions of conservation/identity and a consensus sequence.

Several antibodies were further tested for their ability to bind to IL-23 via Biacore (Table 5). Four out of the 5 of the humanized antibodies tested bound IL-23 with a picomolar range affinity ($K_D$). The antibodies had a faster off-rate when compared to E11E7Chimera.

TABLE 5

Binding of E11E7Chimera and humanized antibodies to IL-23 as measured by SPR

| Antibody | ka (1/Ms) | kd (1/s) less then | $K_D$ (M) less then | Chi$^2$ |
|---|---|---|---|---|
| E11E7Chimera | 5.42E+05 | 1.00E−05** | 1.00E−10** | 0.852 |
| 21-4 | 5.21E+05 | 2.02E−04 | 3.88E−10 | 1.33 |

TABLE 5-continued

Binding of E11E7Chimera and humanized antibodies to IL-23 as measured by SPR

| Antibody | ka (1/Ms) | kd (1/s) less then | $K_D$ (M) less then | Chi$^2$ |
|---|---|---|---|---|
| 8-22 | 4.68E+05 | 1.97E−04 | 4.21E−10 | 1.32 |
| 6-22 | 4.65E+05 | 4.00E−04 | 8.60E−10 | 1.31 |
| 1-4 | 3.48E+05 | 7.33E−04 | 2.11E−09 | 1.65 |
| 20-4 | 4.29E+05 | 2.02E−04 | 4.70E−10 | 1.25 |

**These values are below the limit of sensitivity of the Biacore 3000 which is kd = 1.00E−05 1/s and for $K_D$ is 1.00E−10M).

Specificity of the Humanized Antibodies for IL-23

Four antibodies were selected, based on the results presented in Table 5, to be further screened for their ability to bind selectively to IL-23. Antibodies 21-4, 8-22, 6-22 and 20-4 all demonstrated specific binding to IL-23 and did not significantly bind to either IL-12p40 or IL-23p19 as demonstrated by ELISA (FIG. 8).

EXAMPLE 2

Production of Human Monoclonal Antibodies That Specifically Bind IL-23

Phage Display

A naive bacteriophage (phage) library (XOMA corporation, Berkeley) comprising a plurality of individual human FAb fragments was screened in an attempt to isolate antibodies that bind IL23 but do not significantly bind the individual subunits of IL23, p19 and p40.

Crosslinking Antigens to Dynal M450 Magnetic Epoxy Beads

One mL of Dynal M450 epoxy beads was washed once with 1 mL of 100 mM sodium phosphate pH8.0. The washed beads were resuspended in a further 0.5 mL of 100 mM sodium phosphate pH8.0 and 1.4 moles of the ligand to be coupled added; the final coupling volume being made up to 1 mL with 100 mM sodium phosphate pH8.0. The coupling reaction was allowed to proceed overnight (~16 hours) at room temperature with slow rotation. Beads were subsequently blocked by addition of 200 of 1M tris pH7.4 and slow rotation for 30 minutes at room temperature. Beads were washed 3× in PBS and re-suspended in 1 mL PBS.

Phage Library Biopanning

Following several unsuccessful phage display campaigns using different reagents and/or panning conditions, anti-IL-23 antibodies with the aforementioned specificity were isolated from the phage display library. The general protocol followed the method outlined by Marks et al. (Marks and Bradbury Methods Mol Biol 248: 161-176, 2004). Briefly, each phage display campaign involved three rounds of biopanning with independent screening of both kappa chain- and lambda chain containing libraries. For each round of biopanning phage particles taken from each library were blocked by mixing 1:1 with blocking buffer (5% skim milk in phosphate buffered saline pH 7.4) and incubating for 1 hr at room temperature. The blocked phage library was then pre-depleted where applicable for 1 hr at room temperature using antigens which were blocked as described for the library.

Library panning was conducted by mixing the blocked and pre-depleted library with the selection complexes (pre-blocked) in 1.5 mL microcentrifuge tubes and rotating for 1 hr at room temperature. Non-specifically bound phage were removed using a series of washes. Each wash involved pulling the bead complexes from the solution onto the tube wall using a magnetic rack, aspirating the supernatant and then re-suspending the beads in fresh wash buffer. This was repeated a number of times with either PBS wash buffer (PBS with 0.5% skim milk) or PBS-T wash buffer (PBS with 0.05% TWEEN-20 (Sigma-Aldrich) and 0.5% skim milk). Phage that remained bound after the washing process were eluted.

At the end of the first and second rounds of panning, the output phage were added to a 10 mL culture of exponentially growing TG1 E. coli (yeast-tryptone (YT) growth media) and allowed to infect the cells by incubating for 30 mins at 37° C. without shaking, then with shaking at 250 rpm for 30 mins. The phagemids encoding the phage display output were then rescued as phage particles following a standard protocol (Marks and Bradbury, 2004, supra). At the end of the third panning round TG1 cells were infected with output phage, but the cells were plated on solid YT growth media (supplemented with 2% glucose and 100 μg/mL carbenicillin) at a sufficient dilution to produce discrete E. coli colonies.

Expression of Fabs for Screening

Discrete E. coli colonies from the third round of biopanning the phage library were used to inoculate 1 mL aliquots of 2YT growth media (supplemented with 2% glucose and 100 μg/mL carbenicillin) in 96 well deep well plates. Plates were grown overnight at 30° C. shaking at 380 rpm (Innova 44R shaker, 1 inch orbit) to produce a masterplate. For Fab induction bacteria were diluted 1:100 in a further 96 well deep well plate containing fresh 2YT media (supplemented with 100 μg/mL carbenicillin) and grown at 37° C. 380 rpm until $OD_{600}$ reached 0.5. A final concentration of 1.25 mM IPTG was added and plates were subsequently grown overnight (~16 hours) at 25° C. shaking as before.

Preparation of Soluble Fabs:

Bacterial pellets from induction plates were harvested by centrifugation at 2000 g for 10 minutes (room temperature). Spent media was discarded and pellets resuspended in 200 μl per well of lysozyme buffer composed of 160 μg/mL lysozyme, 10 μg/mL RNAse, 5 μg/mL DNAse and protease inhibitor cocktail (cOmplete, Roche). Plates were incubated at 21° C. 400 rpm for 30 minutes prior to the addition of a further 100 μl per well of lysozyme buffer and further incubation at 21° C. 400 rpm for 30 minutes. Plates were subsequently centrifuged at 3000 g for 15 minutes (room temperature) prior to usage of the Fab extracts in assays.

ELISA Screens for Fab Expression, and Binding to Antigens IL-23, IL-23p19-Fc and IL-12p40-Fc A NuncMaxisorp 96-well plate was coated with untagged human IL-23 at 1 μg/ml in carbonate coating buffer and incubated overnight at 4° C. Further plates were coated as described for IL-23 using the antigens human p19-Fc, human p40-Fc and either anti-kappa or anti-lambda antibodies. Plates were washed then blocked for an hour with 1% BSA in PBS at room temperature. Plates were washed again prior to the addition of 50 μl per well of Fab extract and incubation for a further hour at room temperature. Plates were washed prior to the addition of 50 μl per well of 1:2000 diluted anti-v5-HRP antibody conjugate (Invitrogen™) and incubated for a further hour at room temperature. Plates were washed, developed and read as described previously.

Results of Phage Display of Lead Fabs Showing IL-23-binding Specificity Following numerous screening approaches one Fab (named ST883/885) out of 768

Fabs screened from campaigns 4 and 5, bound IL-23 with little or no binding observed to IL-23p19-Fc or IL-12p40-Fc. Bacteria containing phagemids encoding ST883/885 Fabs with this specificity were regrown overnight in 5 mLs of LB broth (supplemented with 100 μg/ml ampicillin) and used to isolate plasmid DNA for sequencing. The variable heavy chain of ST883/885 is given as SEQ ID NO: 49 and the variable light chain as SEQ ID NO: 50.

The $V_H$ and $V_L$ of ST883/885 were PCR amplified and subcloned into their respective pTT5 heavy and light chain expression vectors. The full-length antibody termed ST883/885IgG was then expressed as a human IgG1 lambda isotype antibody in HEK293E cells as described above. Antibody was purified by Protein A chromatography (as described previously) following removal of the cells from the suspension by centrifugation. As shown in FIG. 9, the antibody was found to be specific for IL-23 with no significant binding to IL-12p40 and IL-23p19.

EXAMPLE 3

Detection of Endogenous IL-23 by an IL-23 specific antibody

IL-23 specific antibodies such as E11E7 are useful in the detection of IL-23 in biological samples.

To demonstrate the effectiveness of E11E7 to detect IL-23 a standard sandwich ELISA was developed. E11E7 at 2 ug/ml in PBS was coated onto a Maxisorp plate (Nunc) and incubated at 4° C. The following day, the plate was washed using PBS with 0.05% Tween-20 (PBS-T) and blocked in 10% feotal calf serum in PBS for 1 hr. rhIL23 was added at a maximum concentration of 3 ng/ml and serial dilutions performed across the plate. The plate was incubated for 1 hour then washed 3x with PBS-T. The complex was detected using biotinylated IL-23 detection Ab followed by 3xPBS-T washed and then Strepavidin HRP detection. Recombinant IL-23 was detected in a dose-titration using E11E7 as a capture antibody (FIG. 10A).

To determine whether E11E7 could be used to detect native IL-23, THP-1 cells were stimulated with 1 ug/mL of Pokeweed Mitogen (PWM) and different concentrations of Lipopolysaccharide (LPS) in culture for 24 hours. The supernatants were then collected and assayed in the above described ELISA format. E11E7 was able to detect native IL-23 at several concentrations of LPS that were tested (FIG. 10B).

EXAMPLE 4

Production of Further Antibodies and Antibody Fragments 4.1 Generation of Hybridoma Cell Lines Monoclonal antibodies against heterodimeric IL-23 are generated by conventional protein immunization or using genetic immunization essentially as described in Example 1. This method is modified in some forms to immunize mice rather than rats.

Hybridoma screening and DNA sequencing are performed essentially as described in Example 1 and/or depicted in FIG. 11.

4.2 Isolation of Further IL-23 Heterodimer Antibodies from Display Libraries

For primary selections, libraries of phage displaying antibody fragments are panned against FLAG-tagged IL-23 protein and positive binding phage retained. Then depletion of phage positive for IL-23p19 subunit binding is performed using Anti-FLAG M2 coated beads (Sigma) and FLAG-tagged p19 in conjunction with depletion of phage positive for IL-12p40 subunit binding using Anti-FLAG M2 coated beads (Sigma) and FLAG-tagged IL-12p40. This will leave phage displaying antibody fragments that are specific for the heterodimeric interface of IL-23 (FIG. 11) (Henderikx et al, Selection of antibodies against biotinylated antigens. Antibody Phage Display: Methods and protocols, Ed. O'Brien and Atkin, Humana Press (2002)). Further affinity maturation of these antibody fragments is performed by screening against Anti-FLAG M2 coated beads (Sigma) and FLAG-tagged IL-23. Phage vectors from selection outputs are then isolated by plasmid preps (Qiagen) and antibody fragment inserts released by restriction digest. These inserts are ligated into a phage expression vector and used to transform *E. coli* strain HB2151 for soluble expression and screening of antibody fragments. Alternatively the antibody fragment inserts are sequenced and are expressed with a truncated human constant region.

EXAMPLE 5

Construction of Vectors Expressing Antibodies and Expression and Purification of Antibodies Vectors expressing antibodies are produced essentially as described above. Antibodies are then expressed and purified essentially as described above.

EXAMPLE 6

Characterization of Purified Antibodies

Antibodies expressed and purified as described in Example 5 are characterized using an ELISA assay, a IL-23/IL-23R inhibition assay and an IL-17 release assay using mouse splenocytes essentially as described above.

EXAMPLE 7

Characterization of the Epitope for Heterodimer Specific Antibodies

Using point mutation technology an alanine is introduced into the protein sequence of IL-23 at each position in which a side chain is predicted to be in contact with solution based on the three dimensional X-ray crystal structures (3D85). Each IL-23 protein containing a single alanine point mutation is then expressed and purified using the methods described above for the expression and purification of IL-23. Using SPR technology the candidate antibody is immobilized on the surface of a Protein A chip and each IL-23 variant protein is passed over the surface and the binding kinetics measured. Protein variants that fail to bind or bind weakly to the immobilized antibody may contain a point mutation at the antibody's epitope on IL-23.

In a further experiment, each IL-23 variant is coated onto an ELISA plate. After blocking, the candidate antibody is then added along with a polyclonal antibody specific to IL-23. Both antibodies are then detected using their corresponding secondary antibodies. Situations in which the candidate antibody fails to bind to the IL-23 variant, but when the polyclonal antibody binds to the IL-23 variant, may indicate that the amino acid position of the alanine mutation on the IL-23 variant serves as an amino acid position that interacts with the candidate antibody.

The invention claimed is:

1. An isolated or recombinant antibody or antigen-binding fragment thereof that specifically binds to IL-23, comprising a heavy chain CDR1comprising the amino acid sequence of SEQ ID NO: 8, a heavy chain CDR2 comprising the amino acid sequence of SEQ ID NO: 9 or 22, a heavy chain CDR3 comprising the amino acid sequence of SEQ ID NO: 10, a light chain CDR1 comprising the amino acid sequence of SEQ ID NO: 13, a light chain CDR2comprising the amino acid sequence of SEQ ID NO: 14, and a light chain CDR3 comprising the amino acid sequence of SEQ ID NO: 15.

2. The antibody or antigen-binding fragment thereof of claim 1, wherein the antibody or antigen-binding fragment thereof specifically binds to an IL-23heterodimeric complex, but does not specifically bind to an IL-12p40 subunit or an IL-23p19subunit individually.

3. The antibody or antigen-binding fragment thereof of claim 1, wherein the antibody or antigen-binding fragment thereof specifically binds to:
  (a) the heterodimeric interface of IL-23;
  (b) the IL-23p19 subunit of IL-23 when said subunit is a component of an IL-23 heterodimeric complex; or
  (c) the IL-23p19 subunit of IL-23 in a region comprising amino acids 112-144 of SEQ ID NO:2 when said subunit is a component of an IL-23 heterodimeric complex.

4. The antibody or antigen-binding fragment thereof of claim 1, wherein the antibody or antigen-binding fragment thereof reduces binding of IL-23 to the IL-23receptor (IL-23R) with an $IC_{50}$ of 1nM or less or an $EC_{50}$ of 1nM or less.

5. The antibody or antigen-binding fragment thereof of claim 1, wherein the antibody or antigen-binding fragment thereof is chimeric, deimmunized, CDR-grafted, humanized, primatized or synhumanized.

6. The antibody or antigen-binding fragment thereof of claim 1, wherein the antibody or antigen-binding fragment thereof is a single chain Fv (scFv) or a dimeric scFv (di-scFv) that is optionally linked to an Fc, a heavy chain constant domain 2($C_H2$), or heavy chain constant domain 3($C_H3$).

7. The antibody or antigen-binding fragment thereof of claim 1, wherein the antibody or antigen-binding fragment thereof is an Fab, F(ab')$_2$, Fv, or a diabody, triabody, or tetrabody that is optionally linked to an Fc, a heavy chain constant domain 2 ($C_H2$), or heavy chain constant domain 3($C_H3$).

8. The antibody or antigen-binding fragment thereof of claim 7, wherein the antibody or antigen-binding fragment thereof is chimeric, de-immunized, humanized, primatized, or synhumanized.

9. The antibody or antigen-binding fragment thereof of claim 8, wherein the antibody or antigen-binding fragment thereof is a humanized antibody comprising:
  (a) a $V_H$ comprising amino acids 1-120 of SEQ ID NO: 30 and a $V_L$ comprising amino acids 1-113 of SEQ ID NO: 45;
  (b) a $V_H$ comprising amino acids 1-120 of SEQ ID NO: 31 and a $V_L$ comprising amino acids 1-113 of SEQ ID NO: 45;
  (c) a $V_H$ comprising amino acids 1-120 of SEQ ID NO: 32 and a $V_L$ comprising amino acids 1-113 of SEQ ID NO: 46; or
  (d) a $V_H$ comprising amino acids 1-120 of SEQ ID NO: 33 and a $V_L$ comprising amino acids 1-113 of SEQ ID NO: 46.

10. The antibody or antigen-binding fragment thereof of claim 8, wherein the antibody or antigen-binding fragment thereof is a chimeric antibody comprising a $V_H$ comprising the amino acid sequence of SEQ ID NO: 7 linked to a human heavy chain constant region and a $V_L$ comprising the amino acid sequence of SEQ ID NO: 12 linked to a human light chain constant region.

11. The antibody or antigen-binding fragment thereof of claim 8, wherein the antibody or antigen-binding fragment thereof is a monoclonal antibody comprising a $V_H$ comprising the amino acid sequence of SEQ ID NO: 7 and a $V_L$ comprising the amino acid sequence of SEQ ID NO: 12, or a chimeric, deimmunized, CDR-grafted, humanized or synhumanized form thereof.

12. The antibody or antigen-binding fragment thereof of claim 1, wherein the antibody or antigen-binding fragment thereof is conjugated to a compound.

13. A composition comprising the antibody or antigen-binding fragment thereof of claim 1 and a suitable carrier or diluent.

14. A recombinant nucleic acid encoding an antibody or antigen-binding fragment thereof that specifically binds to IL-23, and comprises a heavy chain CDR1comprising the amino acid sequence of SEQ ID NO: 8, a heavy chain CDR2 comprising the amino acid sequence of SEQ ID NO: 9 or 22, a heavy chain CDR3 comprising the amino acid sequence of SEQ ID NO: 10, a light chain CDR1 comprising the amino acid sequence of SEQ ID NO: 13, a light chain CDR2 comprising the amino acid sequence of SEQ ID NO: 14, and a light chain CDR3comprising the amino acid sequence of SEQ ID NO: 15.

15. A recombinant cell comprising the nucleic acid of claim 14.

16. A method for treating an IL-23-mediated inflammatory condition in a subject, comprising administering to the subject an effective amount of an isolated or recombinant antibody or antigen-binding fragment thereof, that specifically binds to IL-23 and comprises a heavy chain CDR1 comprising the amino acid sequence of SEQ ID NO: 8, a heavy chain CDR2 comprising the amino acid sequence of SEQ ID NO: 9 or 22, a heavy chain CDR3 comprising the amino acid sequence of SEQ ID NO: 10, a light chain CDR1 comprising the amino acid sequence of SEQ ID NO: 13, a light chain CDR2 comprising the amino acid sequence of SEQ ID NO: 14, and a light chain CDR3 comprising the amino acid sequence of SEQ ID NO: 15, thereby treating the IL-23-mediated inflammatory condition.

* * * * *

SEQUENCE LISTING

```
<160> NUMBER OF SEQ ID NOS: 83

<210> SEQ ID NO 1
<211> LENGTH: 328
<212> TYPE: PRT
<213> ORGANISM: Homo sapiens
<220> FEATURE:
<221> NAME/KEY: SIGNAL
<222> LOCATION: (1)..(22)
<220> FEATURE:
<221> NAME/KEY: mat_peptide
<222> LOCATION: (23)..(328)

<400> SEQUENCE: 1

Met Cys His Gln Gln Leu Val Ile Ser Trp Phe Ser Leu Val Phe Leu
        -20                 -15                 -10

Ala Ser Pro Leu Val Ala Ile Trp Glu Leu Lys Lys Asp Val Tyr Val
         -5              -1   1               5                  10

Val Glu Leu Asp Trp Tyr Pro Asp Ala Pro Gly Glu Met Val Val Leu
                     15                  20                  25

Thr Cys Asp Thr Pro Glu Glu Asp Gly Ile Thr Trp Thr Leu Asp Gln
                 30                  35                  40

Ser Ser Glu Val Leu Gly Ser Gly Lys Thr Leu Thr Ile Gln Val Lys
             45                  50                  55

Glu Phe Gly Asp Ala Gly Gln Tyr Thr Cys His Lys Gly Gly Glu Val
         60                  65                  70

Leu Ser His Ser Leu Leu Leu Leu His Lys Lys Glu Asp Gly Ile Trp
75                   80                  85                  90

Ser Thr Asp Ile Leu Lys Asp Gln Lys Glu Pro Lys Asn Lys Thr Phe
                 95                  100                 105
```

```
Leu Arg Cys Glu Ala Lys Asn Tyr Ser Gly Arg Phe Thr Cys Trp Trp
                110                 115                 120

Leu Thr Thr Ile Ser Thr Asp Leu Thr Phe Ser Val Lys Ser Ser Arg
            125                 130                 135

Gly Ser Ser Asp Pro Gln Gly Val Thr Cys Gly Ala Ala Thr Leu Ser
        140                 145                 150

Ala Glu Arg Val Arg Gly Asp Asn Lys Glu Tyr Glu Tyr Ser Val Glu
155                 160                 165                 170

Cys Gln Glu Asp Ser Ala Cys Pro Ala Ala Glu Glu Ser Leu Pro Ile
                175                 180                 185

Glu Val Met Val Asp Ala Val His Lys Leu Lys Tyr Glu Asn Tyr Thr
            190                 195                 200

Ser Ser Phe Phe Ile Arg Asp Ile Ile Lys Pro Asp Pro Pro Lys Asn
        205                 210                 215

Leu Gln Leu Lys Pro Leu Lys Asn Ser Arg Gln Val Glu Val Ser Trp
220                 225                 230

Glu Tyr Pro Asp Thr Trp Ser Thr Pro His Ser Tyr Phe Ser Leu Thr
235                 240                 245                 250

Phe Cys Val Gln Val Gln Gly Lys Ser Lys Arg Glu Lys Lys Asp Arg
                255                 260                 265

Val Phe Thr Asp Lys Thr Ser Ala Thr Val Ile Cys Arg Lys Asn Ala
            270                 275                 280

Ser Ile Ser Val Arg Ala Gln Asp Arg Tyr Tyr Ser Ser Ser Trp Ser
        285                 290                 295

Glu Trp Ala Ser Val Pro Cys Ser
300                 305

<210> SEQ ID NO 2
<211> LENGTH: 170
<212> TYPE: PRT
<213> ORGANISM: Homo sapiens

<400> SEQUENCE: 2

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170
```

<210> SEQ ID NO 3
<211> LENGTH: 330
<212> TYPE: PRT
<213> ORGANISM: Homo sapiens

<400> SEQUENCE: 3

```
Ala Ser Thr Lys Asn Pro Asp Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 4
<211> LENGTH: 106
<212> TYPE: PRT
<213> ORGANISM: Homo sapiens

<400> SEQUENCE: 4

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 5
<211> LENGTH: 1557
<212> TYPE: DNA
<213> ORGANISM: artificial
<220> FEATURE:
<223> OTHER INFORMATION: Nucleotide sequence encoding fusion protein
      comprising IL-12p40 and IL-23p19 linked by a flexible linker

<400> SEQUENCE: 5

```
atgtgtcatc agcagctcgt catcagctgg ttcagcctgg tgttcctggc ctcccccctg      60
gtggctatct gggagctgaa gaaagacgtg tacgtggtgg agctggactg gtatcccgac     120
gcccctggcg agatggtggt gctgacctgc gacacccccg aagaggacgg catcacctgg     180
accctggacc agagcagcga ggtgctgggc agcggcaaga ccctgaccat ccaggtgaaa     240
gagttcggcg acgccggcca gtacacctgc cacaagggcg cgaagtgct gtcccacagc     300
ctgctgctgc tgcacaagaa agaggatggc atctggtcca ccgacatcct gaaggaccag     360
aaagagccca gaacaagac cttcctgaga tgcgaggcca gaactacag cggccggttc     420
acctgttggt ggctgaccac catcagcacc gacctgacct tcagcgtgaa gtccagccgg     480
ggcagcagcg accctcaggg cgtgacctgc ggagccgcca ccctgagcgc cgagagagtg     540
cggggcgaca caaagagta cgagtacagc gtcgagtgcc aggaagatag cgcctgccct     600
gccgccgagg aaagcctgcc catcgaagtg atggtggacg ccgtgcacaa gctgaagtac     660
gagaactaca cctccagctt tttcatccgg gacatcatca gcccgaccc ccccaagaac     720
ctgcagctga agcccctgaa gaacagccgg caggtggagg tgtcctggga gtaccctgac     780
acctggtcca ccccccacag ctacttcagc ctgaccttct gtgtgcaggt gcagggcaag     840
agcaagcggg agaagaaga ccgggtgttc accgacaaga ccagcgccac cgtgatctgc     900
cggaagaacg ccagcatcag cgtgcgggcc caggaccggt actacagcag ctcttggagc     960
gagtgggcca gcgtgccctg tagcggatct ggcagcagca gaggcggcag cggaagcggc    1020
ggctctggcg gcggaggaag caagctgaga gccgtccctg gcggcagctc ccctgcctgg    1080
acccagtgcc agcagctctc acagaagctg tgcaccctgg cctggtccgc ccaccctctg    1140
gtgggccaca tggacctgcg ggaggaaggc gacgaggaaa ccaccaacga cgtcccccac    1200
atccagtgcg gcgacggctg cgatccccag ggcctgcggg acaacagcca gttctgcctg    1260
cagagaatcc atcagggact gatcttctac gagaagctgc tgggctccga catcttcacc    1320
ggcgagcccc ccctgctgcc cgacagcccc gtgggacagc tgcacgccag cctgctgggc    1380
```

```
ctgagccagc tgctgcagcc cgagggccac cactgggaga cacagcagat ccccagcctg   1440
agccccagcc agccctggca gcggctgctg ctgagattca agatcctgag aagcctgcag   1500
gccttcgtgg ccgtggccgc cagagtgttc gcccacggag ccgccacact gtcccccc    1557

<210> SEQ ID NO 6
<211> LENGTH: 360
<212> TYPE: DNA
<213> ORGANISM: Rattus norvegicus

<400> SEQUENCE: 6
caggtgcagc tgaaggagtc aggacctggt ctggtgcagc cctcacagac cctgtccctc     60
acctgcactg tctctgggtt ctcactaatc agctacaatg tgcactgggt tcgacagcct    120
agaggaaaag gtctggagtg gatgggagta atatggactg gtggaagcac agattacaat    180
tcagttctca atcccgact gagcatcagc aggacacct ccaagagcca gttttcttta     240
aaaatgcaca gtctgcaaac tgaagacata ggcacttact actgtgccag agataagtac    300
ggattattcc cggggtactt tgattactgg ggccaaggag tcatggtcac agtctcctca    360

<210> SEQ ID NO 7
<211> LENGTH: 120
<212> TYPE: PRT
<213> ORGANISM: Rattus norvegicus

<400> SEQUENCE: 7

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Ile Ser Tyr
            20                  25                  30

Asn Val His Trp Val Arg Gln Pro Arg Gly Lys Gly Leu Glu Trp Met
        35                  40                  45

Gly Val Ile Trp Thr Gly Gly Ser Thr Asp Tyr Asn Ser Val Leu Lys
    50                  55                  60

Ser Arg Leu Ser Ile Ser Arg Asp Thr Ser Lys Ser Gln Val Phe Leu
65                  70                  75                  80

Lys Met His Ser Leu Gln Thr Glu Asp Ile Gly Thr Tyr Tyr Cys Ala
                85                  90                  95

Arg Asp Lys Tyr Gly Leu Phe Pro Gly Tyr Phe Asp Tyr Trp Gly Gln
            100                 105                 110

Gly Val Met Val Thr Val Ser Ser
        115                 120

<210> SEQ ID NO 8
<211> LENGTH: 5
<212> TYPE: PRT
<213> ORGANISM: artificial
<220> FEATURE:
<223> OTHER INFORMATION: Antibody E11E7 VH CDR1

<400> SEQUENCE: 8

Ser Tyr Asn Val His
1               5

<210> SEQ ID NO 9
<211> LENGTH: 16
<212> TYPE: PRT
<213> ORGANISM: artificial
<220> FEATURE:
<223> OTHER INFORMATION: Antibody E11E7 VH CDR2
```

```
<400> SEQUENCE: 9

Val Ile Trp Thr Gly Gly Ser Thr Asp Tyr Asn Ser Val Leu Lys Ser
1               5                   10                  15

<210> SEQ ID NO 10
<211> LENGTH: 12
<212> TYPE: PRT
<213> ORGANISM: artificial
<220> FEATURE:
<223> OTHER INFORMATION: Antibody E11E7 VH CDR3

<400> SEQUENCE: 10

Asp Lys Tyr Gly Leu Phe Pro Gly Tyr Phe Asp Tyr
1               5                   10

<210> SEQ ID NO 11
<211> LENGTH: 342
<212> TYPE: DNA
<213> ORGANISM: Rattus norvegicus

<400> SEQUENCE: 11
gacattgtga tgacccagtc tcctttctcc ctggctgtgt cagaaggaga aatggtcact      60
ataaactgca agcccagtca gagtctttta tccagtggaa accgaaagaa ctacttggcc    120
tggtaccagc agaaaccagg gcagtctcct aaactactga tctactatgc atccactagg    180
caatcagggg tccctgatcg cttcataggc agtggatctg ggacagactt cactctgacc    240
atcagcgatg tgcaggctga agacctggca gattattact gcctgcaaca tttcaactat    300
ccgtggacgt tcggtggagg caccaagctg gaattgaaac gg                       342

<210> SEQ ID NO 12
<211> LENGTH: 114
<212> TYPE: PRT
<213> ORGANISM: Rattus norvegicus

<400> SEQUENCE: 12

Asp Ile Val Met Thr Gln Ser Pro Phe Ser Leu Ala Val Ser Glu Gly
1               5                   10                  15

Glu Met Val Thr Ile Asn Cys Lys Pro Ser Gln Ser Leu Leu Ser Ser
            20                  25                  30

Gly Asn Arg Lys Asn Tyr Leu Ala Trp Tyr Gln Gln Lys Pro Gly Gln
        35                  40                  45

Ser Pro Lys Leu Leu Ile Tyr Tyr Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Asp Val Gln Ala Glu Asp Leu Ala Asp Tyr Tyr Cys Leu Gln
                85                  90                  95

His Phe Asn Tyr Pro Trp Thr Phe Gly Gly Gly Thr Lys Leu Glu Leu
            100                 105                 110

Lys Arg

<210> SEQ ID NO 13
<211> LENGTH: 17
<212> TYPE: PRT
<213> ORGANISM: artificial
<220> FEATURE:
<223> OTHER INFORMATION: Antibody E11E7 VL CDR1

<400> SEQUENCE: 13
```

```
Lys Pro Ser Gln Ser Leu Leu Ser Ser Gly Asn Arg Lys Asn Tyr Leu
1               5                   10                  15

Ala

<210> SEQ ID NO 14
<211> LENGTH: 7
<212> TYPE: PRT
<213> ORGANISM: artificial
<220> FEATURE:
<223> OTHER INFORMATION: Antibody E11E7 VL CDR2

<400> SEQUENCE: 14

Tyr Ala Ser Thr Arg Gln Ser
1               5

<210> SEQ ID NO 15
<211> LENGTH: 9
<212> TYPE: PRT
<213> ORGANISM: artificial
<220> FEATURE:
<223> OTHER INFORMATION: Antibody E11E7 VL CDR3

<400> SEQUENCE: 15

Leu Gln His Phe Asn Tyr Pro Trp Thr
1               5

<210> SEQ ID NO 16
<211> LENGTH: 330
<212> TYPE: PRT
<213> ORGANISM: Homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                    210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 8
<212> TYPE: PRT
<213> ORGANISM: artificial
<220> FEATURE:
<223> OTHER INFORMATION: FLAG tag

<400> SEQUENCE: 17

Asp Tyr Lys Asp Asp Asp Asp Lys
1               5

<210> SEQ ID NO 18
<211> LENGTH: 342
<212> TYPE: DNA
<213> ORGANISM: Artificial Sequence
<220> FEATURE:
<223> OTHER INFORMATION: DNA sequence of E11E7Chimera light chain
      immunoglobulin sequence

<400> SEQUENCE: 18
gacatcgtga tgacccagag ccccttcagc ctggccgtga gcgagggcga gatggtgacc      60
atcaactgca agcccagcca gagcctgctg agcagcggca ccggaagaa  ctacctggcc     120 tggtatcagc agaagcccgg ccagtccccc aagctgctga tctactacgc cagcaccaga     180
cagagcggcg tgcccgacag attcatcggc agcggctccg gcaccgactt cacccctgacc    240 atcagcgacg tgcaggccga ggacctggcc gactactact gcctgcagca cttcaactac     300
ccctggacct tcggcggagg caccaagctg gaactgaagc gt                        342

<210> SEQ ID NO 19
<211> LENGTH: 360
<212> TYPE: DNA
<213> ORGANISM: Artificial Sequence
<220> FEATURE:
<223> OTHER INFORMATION: DNA sequence of E11E7Chimera heavy chain
      immunoglobulin sequence

<400> SEQUENCE: 19
caggtgcagc tgaaagagtc cggccctggc ctggtgcagc ctagccagac cctgagcctg      60
acctgcaccg tgtccggctt cagcctgatc agctacaacg tgcactgggt cgccagcct     120 agaggcaagg gcctggaatg gatgggcgtg atctggaccg gcggcagcac cgactacaac     180
agcgtgctga gtctcggct cagcattagc agagacacca gcaagagcca ggtgttcctg      240
aagatgcaca gcctgcagac cgaggacatc ggcacctact actgcgccag agacaagtac     300
```

```
ggcctgttcc ccggctactt cgattactgg ggccagggcg tgatggtgac cgtgtcctca    360
```

<210> SEQ ID NO 20
<211> LENGTH: 450
<212> TYPE: PRT
<213> ORGANISM: artificial
<220> FEATURE:
<223> OTHER INFORMATION: heavy chain of a chimeric antibody comprising
      E11E7 VH and human constant region (designated E11E7Chimera)

<400> SEQUENCE: 20

```
Gln Val Gln Leu Lys Glu Ser Gly Pro Gly Leu Val Gln Pro Ser Gln
  1               5                  10                  15

Thr Leu Ser Leu Thr Cys Thr Val Ser Gly Phe Ser Leu Ile Ser Tyr
             20                  25                  30

Asn Val His Trp Val Arg Gln Pro Arg Gly Lys Gly Leu Glu Trp Met
         35                  40                  45

Gly Val Ile Trp Thr Gly Gly Ser Thr Asp Tyr Asn Ser Val Leu Lys
     50                  55                  60

Ser Arg Leu Ser Ile Ser Arg Asp Thr Ser Lys Ser Gln Val Phe Leu
 65                  70                  75                  80

Lys Met His Ser Leu Gln Thr Glu Asp Ile Gly Thr Tyr Tyr Cys Ala
                 85                  90                  95

Arg Asp Lys Tyr Gly Leu Phe Pro Gly Tyr Phe Asp Tyr Trp Gly Gln
            100                 105                 110

Gly Val Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 21
<211> LENGTH: 220
<212> TYPE: PRT
<213> ORGANISM: artificial
<220> FEATURE:
<223> OTHER INFORMATION: light chain of a chimeric antibody comprising
      E11E7 VL and human constant region (designated E11E7Chimera)

<400> SEQUENCE: 21

Asp Ile Val Met Thr Gln Ser Pro Phe Ser Leu Ala Val Ser Glu Gly
1               5                   10                  15

Glu Met Val Thr Ile Asn Cys Lys Pro Ser Gln Ser Leu Leu Ser Ser
            20                  25                  30

Gly Asn Arg Lys Asn Tyr Leu Ala Trp Tyr Gln Gln Lys Pro Gly Gln
        35                  40                  45

Ser Pro Lys Leu Leu Ile Tyr Tyr Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Asp Val Gln Ala Glu Asp Leu Ala Asp Tyr Tyr Cys Leu Gln
                85                  90                  95

His Phe Asn Tyr Pro Trp Thr Phe Gly Gly Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 22
<211> LENGTH: 16
<212> TYPE: PRT
```

```
<213> ORGANISM: artificial
<220> FEATURE:
<223> OTHER INFORMATION: an alternative CDR2 of a VH of an antibody that
      binds to IL-23

<400> SEQUENCE: 22

Val Ile Trp Thr Gly Gly Ser Thr Asp Tyr Asn Pro Ser Leu Lys Ser
1               5                   10                  15

<210> SEQ ID NO 23
<211> LENGTH: 7
<212> TYPE: PRT
<213> ORGANISM: artificial
<220> FEATURE:
<223> OTHER INFORMATION: consensus sequence of a CDR1 of a VH of an
      anti-IL-23 antibody (according to the enhanced Chothia numbering
      system).
<220> FEATURE:
<221> NAME/KEY: VARIANT
<222> LOCATION: (2)..(2)
<223> OTHER INFORMATION: X at position 2 is F, G or A
<220> FEATURE:
<221> NAME/KEY: VARIANT
<222> LOCATION: (4)..(4)
<223> OTHER INFORMATION: X at position 4 is I, L or F
<220> FEATURE:
<221> NAME/KEY: VARIANT
<222> LOCATION: (5)..(5)
<223> OTHER INFORMATION: X at position 5 is I or S

<400> SEQUENCE: 23

Gly Xaa Ser Xaa Xaa Ser Tyr
1               5

<210> SEQ ID NO 24
<211> LENGTH: 16
<212> TYPE: PRT
<213> ORGANISM: artificial
<220> FEATURE:
<223> OTHER INFORMATION: consensus sequence of a CDR2 of a VH of an
      anti-IL-23 antibody (according to the Kabat numbering system)
<220> FEATURE:
<221> NAME/KEY: VARIANT
<222> LOCATION: (12)..(12)
<223> OTHER INFORMATION: X at position 12 is P or S
<220> FEATURE:
<221> NAME/KEY: VARIANT
<222> LOCATION: (13)..(13)
<223> OTHER INFORMATION: X at position 13 is V or S

<400> SEQUENCE: 24

Val Ile Trp Thr Gly Gly Ser Thr Asp Tyr Asn Xaa Xaa Leu Lys Ser
1               5                   10                  15

<210> SEQ ID NO 25
<211> LENGTH: 7
<212> TYPE: PRT
<213> ORGANISM: artificial
<220> FEATURE:
<223> OTHER INFORMATION: consensus sequence of a CDR1 of a VH of a
      humanized anti-IL-23 antibody (according to the enhanced Chothia
      numbering system)
<220> FEATURE:
<221> NAME/KEY: VARIANT
<222> LOCATION: (4)..(4)
<223> OTHER INFORMATION: X at position 4 is I or L
<220> FEATURE:
<221> NAME/KEY: VARIANT
<222> LOCATION: (5)..(5)
<223> OTHER INFORMATION: X at position 5 is I or S

<400> SEQUENCE: 25
```

```
Gly Phe Ser Xaa Xaa Ser Tyr
1               5
```

<210> SEQ ID NO 26
<211> LENGTH: 120
<212> TYPE: PRT
<213> ORGANISM: artificial
<220> FEATURE:
<223> OTHER INFORMATION: consensus sequence of a VH of an anti-IL-23
      antibody
<220> FEATURE:
<221> NAME/KEY: VARIANT
<222> LOCATION: (1)..(1)
<223> OTHER INFORMATION: X at position 1 is E or Q
<220> FEATURE:
<221> NAME/KEY: VARIANT
<222> LOCATION: (5)..(5)
<223> OTHER INFORMATION: X at position 5 is Q or K
<220> FEATURE:
<221> NAME/KEY: VARIANT
<222> LOCATION: (6)..(6)
<223> OTHER INFORMATION: X at position 6 is E or Q
<220> FEATURE:
<221> NAME/KEY: VARIANT
<222> LOCATION: (7)..(7)
<223> OTHER INFORMATION: X at position 7 is W or S
<220> FEATURE:
<221> NAME/KEY: VARIANT
<222> LOCATION: (9)..(9)
<223> OTHER INFORMATION: X at position 9 is P or A
<220> FEATURE:
<221> NAME/KEY: VARIANT
<222> LOCATION: (12)..(12)
<223> OTHER INFORMATION: X at position 12 is V or L
<220> FEATURE:
<221> NAME/KEY: VARIANT
<222> LOCATION: (13)..(13)
<223> OTHER INFORMATION: X at position 13 is K or Q
<220> FEATURE:
<221> NAME/KEY: VARIANT
<222> LOCATION: (16)..(16)
<223> OTHER INFORMATION: X at position 16 is E or Q
<220> FEATURE:
<221> NAME/KEY: VARIANT
<222> LOCATION: (23)..(23)
<223> OTHER INFORMATION: X at position 23 is T or A
<220> FEATURE:
<221> NAME/KEY: VARIANT
<222> LOCATION: (25)..(25)
<223> OTHER INFORMATION: X at position 23 is S or Y
<220> FEATURE:
<221> NAME/KEY: VARIANT
<222> LOCATION: (27)..(27)
<223> OTHER INFORMATION: X at position 27 is F or G
<220> FEATURE:
<221> NAME/KEY: VARIANT
<222> LOCATION: (29)..(29)
<223> OTHER INFORMATION: X at position 29 is I, L or F
<220> FEATURE:
<221> NAME/KEY: VARIANT
<222> LOCATION: (30)..(30)
<223> OTHER INFORMATION: X at position 30 is I or S
<220> FEATURE:
<221> NAME/KEY: VARIANT
<222> LOCATION: (37)..(37)
<223> OTHER INFORMATION: X at position 37 is I or V
<220> FEATURE:
<221> NAME/KEY: VARIANT
<222> LOCATION: (41)..(41)
<223> OTHER INFORMATION: X at position 41 is P or R
<220> FEATURE:
<221> NAME/KEY: VARIANT
<222> LOCATION: (48)..(48)
<223> OTHER INFORMATION: X at position 48 is I or M
<220> FEATURE:
<221> NAME/KEY: VARIANT
<222> LOCATION: (61)..(61)
<223> OTHER INFORMATION: X at position 61 is P or S

```
<220> FEATURE:
<221> NAME/KEY: VARIANT
<222> LOCATION: (62)..(62)
<223> OTHER INFORMATION: X at position 62 is V or S
<220> FEATURE:
<221> NAME/KEY: VARIANT
<222> LOCATION: (67)..(67)
<223> OTHER INFORMATION: X at position 67 is L or V
<220> FEATURE:
<221> NAME/KEY: VARIANT
<222> LOCATION: (68)..(68)
<223> OTHER INFORMATION: X at position 1 is S or T
<220> FEATURE:
<221> NAME/KEY: VARIANT
<222> LOCATION: (68)..(68)
<223> OTHER INFORMATION: X at position 68 is S or T
<220> FEATURE:
<221> NAME/KEY: VARIANT
<222> LOCATION: (69)..(69)
<223> OTHER INFORMATION: X at position 69 is I or M
<220> FEATURE:
<221> NAME/KEY: VARIANT
<222> LOCATION: (71)..(71)
<223> OTHER INFORMATION: X at position 71 is R or V
<220> FEATURE:
<221> NAME/KEY: VARIANT
<222> LOCATION: (76)..(76)
<223> OTHER INFORMATION: X at position 76 is S or N
<220> FEATURE:
<221> NAME/KEY: VARIANT
<222> LOCATION: (78)..(78)
<223> OTHER INFORMATION: X at position 78 is F or V
<220> FEATURE:
<221> NAME/KEY: VARIANT
<222> LOCATION: (79)..(79)
<223> OTHER INFORMATION: X at position 79 is F or S
<220> FEATURE:
<221> NAME/KEY: VARIANT
<222> LOCATION: (82)..(82)
<223> OTHER INFORMATION: X at position 82 is M, V or L
<220> FEATURE:
<221> NAME/KEY: VARIANT
<222> LOCATION: (83)..(83)
<223> OTHER INFORMATION: X at position 83 is H, N or S
<220> FEATURE:
<221> NAME/KEY: VARIANT
<222> LOCATION: (85)..(85)
<223> OTHER INFORMATION: X at position 85 is L or V
<220> FEATURE:
<221> NAME/KEY: VARIANT
<222> LOCATION: (86)..(86)
<223> OTHER INFORMATION: X at position 86 is Q or T
<220> FEATURE:
<221> NAME/KEY: VARIANT
<222> LOCATION: (87)..(87)
<223> OTHER INFORMATION: X at position 87 is T or A
<220> FEATURE:
<221> NAME/KEY: VARIANT
<222> LOCATION: (88)..(88)
<223> OTHER INFORMATION: X at position 88 is E or A
<220> FEATURE:
<221> NAME/KEY: VARIANT
<222> LOCATION: (90)..(90)
<223> OTHER INFORMATION: X at position 90 is I or T
<220> FEATURE:
<221> NAME/KEY: VARIANT
<222> LOCATION: (91)..(91)
<223> OTHER INFORMATION: X at position 91 is G or A
<220> FEATURE:
<221> NAME/KEY: VARIANT
<222> LOCATION: (92)..(92)
<223> OTHER INFORMATION: X at position 92 is T or V
<220> FEATURE:
<221> NAME/KEY: VARIANT
<222> LOCATION: (114)..(114)
<223> OTHER INFORMATION: X at position 114 is V or T
<220> FEATURE:
<221> NAME/KEY: VARIANT
<222> LOCATION: (115)..(115)
```

<223> OTHER INFORMATION: X at position 115 is M or L

<400> SEQUENCE: 26

Xaa Val Gln Leu Xaa Xaa Gly Xaa Gly Leu Xaa Xaa Pro Ser Xaa
1               5                   10                  15

Thr Leu Ser Leu Thr Cys Xaa Val Xaa Gly Xaa Ser Xaa Xaa Ser Tyr
            20                  25                  30

Asn Val His Trp Xaa Arg Gln Pro Xaa Gly Lys Gly Leu Glu Trp Xaa
            35                  40                  45

Gly Val Ile Trp Thr Gly Gly Ser Thr Asp Tyr Asn Xaa Xaa Leu Lys
        50                  55                  60

Ser Arg Xaa Xaa Xaa Ser Xaa Asp Thr Ser Lys Xaa Gln Xaa Xaa Leu
65                  70                  75                  80

Lys Xaa Xaa Ser Xaa Xaa Xaa Xaa Asp Xaa Xaa Xaa Tyr Tyr Cys Ala
            85                  90                  95

Arg Asp Lys Tyr Gly Leu Phe Pro Phe Tyr Phe Asp Tyr Trp Gly Gln
            100                 105                 110

Gly Xaa Xaa Val Thr Val Ser Ser
        115                 120

<210> SEQ ID NO 27
<211> LENGTH: 113
<212> TYPE: PRT
<213> ORGANISM: artificial
<220> FEATURE:
<223> OTHER INFORMATION: consensus sequence of a VL of an anti-IL-23
      antibody
<220> FEATURE:
<221> NAME/KEY: VARIANT
<222> LOCATION: (1)..(1)
<223> OTHER INFORMATION: X at position 1 is E or D
<220> FEATURE:
<221> NAME/KEY: VARIANT
<222> LOCATION: (4)..(4)
<223> OTHER INFORMATION: X at position 4 is M or L
<220> FEATURE:
<221> NAME/KEY: VARIANT
<222> LOCATION: (7)..(7)
<223> OTHER INFORMATION: X at position 7 is S or T
<220> FEATURE:
<221> NAME/KEY: VARIANT
<222> LOCATION: (9)..(9)
<223> OTHER INFORMATION: X at position 9 is A, L, D or F
<220> FEATURE:
<221> NAME/KEY: VARIANT
<222> LOCATION: (10)..(10)
<223> OTHER INFORMATION: X at position 10 is S or T
<220> FEATURE:
<221> NAME/KEY: VARIANT
<222> LOCATION: (12)..(12)
<223> OTHER INFORMATION: X at position 12 is A, P or S
<220> FEATURE:
<221> NAME/KEY: VARIANT
<222> LOCATION: (13)..(13)
<223> OTHER INFORMATION: X at position 13 is V or L
<220> FEATURE:
<221> NAME/KEY: VARIANT
<222> LOCATION: (14)..(14)
<223> OTHER INFORMATION: X at position 14 is S or T
<220> FEATURE:
<221> NAME/KEY: VARIANT
<222> LOCATION: (15)..(15)
<223> OTHER INFORMATION: X at position 15 is E, L or P
<220> FEATURE:
<221> NAME/KEY: VARIANT
<222> LOCATION: (18)..(18)
<223> OTHER INFORMATION: X at position 18 is M, R or P
<220> FEATURE:
<221> NAME/KEY: VARIANT
<222> LOCATION: (19)..(19)

-continued

```
<223> OTHER INFORMATION: X at position 19 is V or A
<220> FEATURE:
<221> NAME/KEY: VARIANT
<222> LOCATION: (20)..(20)
<223> OTHER INFORMATION: X at position 20 is T or S
<220> FEATURE:
<221> NAME/KEY: VARIANT
<222> LOCATION: (21)..(21)
<223> OTHER INFORMATION: X at position 21 is I or L
<220> FEATURE:
<221> NAME/KEY: VARIANT
<222> LOCATION: (22)..(22)
<223> OTHER INFORMATION: X at position 22 is N or S
<220> FEATURE:
<221> NAME/KEY: VARIANT
<222> LOCATION: (43)..(43)
<223> OTHER INFORMATION: X at position 43 is Q or L
<220> FEATURE:
<221> NAME/KEY: VARIANT
<222> LOCATION: (49)..(49)
<223> OTHER INFORMATION: X at position 49 is P, S or A
<220> FEATURE:
<221> NAME/KEY: VARIANT
<222> LOCATION: (51)..(51)
<223> OTHER INFORMATION: X at position 51 is K, R or Q
<220> FEATURE:
<221> NAME/KEY: VARIANT
<222> LOCATION: (64)..(64)
<223> OTHER INFORMATION: X at position 64 is V or I
<220> FEATURE:
<221> NAME/KEY: VARIANT
<222> LOCATION: (66)..(66)
<223> OTHER INFORMATION: X at position 66 is D or A
<220> FEATURE:
<221> NAME/KEY: VARIANT
<222> LOCATION: (69)..(69)
<223> OTHER INFORMATION: X at position 69 is I or S
<220> FEATURE:
<221> NAME/KEY: VARIANT
<222> LOCATION: (80)..(80)
<223> OTHER INFORMATION: X at position 80 is T or K
<220> FEATURE:
<221> NAME/KEY: VARIANT
<222> LOCATION: (83)..(83)
<223> OTHER INFORMATION: X at position 83 is D, S or R
<220> FEATURE:
<221> NAME/KEY: VARIANT
<222> LOCATION: (84)..(84)
<223> OTHER INFORMATION: X at position 84 is V or L
<220> FEATURE:
<221> NAME/KEY: VARIANT
<222> LOCATION: (85)..(85)
<223> OTHER INFORMATION: X at position 85 is Q or E
<220> FEATURE:
<221> NAME/KEY: VARIANT
<222> LOCATION: (86)..(86)
<223> OTHER INFORMATION: X at position 86 is A or P
<220> FEATURE:
<221> NAME/KEY: VARIANT
<222> LOCATION: (89)..(89)
<223> OTHER INFORMATION: X at position 89 is L, V or F
<220> FEATURE:
<221> NAME/KEY: VARIANT
<222> LOCATION: (90)..(90)
<223> OTHER INFORMATION: X at position 90 is A or G
<220> FEATURE:
<221> NAME/KEY: VARIANT
<222> LOCATION: (91)..(91)
<223> OTHER INFORMATION: X at position 91 is D or V
<220> FEATURE:
<221> NAME/KEY: VARIANT
<222> LOCATION: (106)..(106)
<223> OTHER INFORMATION: X at position 106 is G or Q
<220> FEATURE:
<221> NAME/KEY: VARIANT
<222> LOCATION: (110)..(110)
<223> OTHER INFORMATION: X at position 110 is L, V or A
<220> FEATURE:
<221> NAME/KEY: VARIANT
```

<222> LOCATION: (112)..(112)
<223> OTHER INFORMATION: X at position 112 is L or I

<400> SEQUENCE: 27

Xaa Ile Val Xaa Thr Gln Xaa Pro Xaa Xaa Leu Xaa Xaa Xaa Xaa Gly
1               5                   10                  15

Glu Xaa Xaa Xaa Xaa Xaa Cys Lys Pro Ser Gln Ser Leu Leu Ser Ser
                20                  25                  30

Gly Asn Arg Lys Asn Tyr Leu Ala Trp Tyr Xaa Gln Lys Pro Gly Gln
            35                  40                  45

Xaa Pro Xaa Leu Lys Ile Tyr Tyr Ala Ser Thr Arg Gln Ser Gly Xaa
        50                  55                  60

Pro Xaa Arg Phe Xaa Gly Ser Gly Ser Gly Thr Asp Phe Thr Leu Xaa
65                  70                  75                  80

Ile Ser Xaa Xaa Xaa Xaa Glu Asp Xaa Xaa Xaa Tyr Tyr Cys Leu Gln
                85                  90                  95

His Phe Asn Tyr Pro Trp Thr Phe Gly Xaa Gly Thr Lys Xaa Glu Xaa
                100                 105                 110

Lys

<210> SEQ ID NO 28
<211> LENGTH: 120
<212> TYPE: PRT
<213> ORGANISM: artificial
<220> FEATURE:
<223> OTHER INFORMATION: consensus sequence of a VH of a humanized
      anti-IL-23 antibody
<220> FEATURE:
<221> NAME/KEY: VARIANT
<222> LOCATION: (1)..(1)
<223> OTHER INFORMATION: X at position 1 is Q or E
<220> FEATURE:
<221> NAME/KEY: VARIANT
<222> LOCATION: (6)..(6)
<223> OTHER INFORMATION: X at position 6 is E or Q
<220> FEATURE:
<221> NAME/KEY: VARIANT
<222> LOCATION: (7)..(7)
<223> OTHER INFORMATION: X at position 7 is W or S
<220> FEATURE:
<221> NAME/KEY: VARIANT
<222> LOCATION: (9)..(9)
<223> OTHER INFORMATION: X at position 9 is P or A
<220> FEATURE:
<221> NAME/KEY: VARIANT
<222> LOCATION: (12)..(12)
<223> OTHER INFORMATION: X at position 12 is V or L
<220> FEATURE:
<221> NAME/KEY: VARIANT
<222> LOCATION: (23)..(23)
<223> OTHER INFORMATION: X at position 23 is T or A
<220> FEATURE:
<221> NAME/KEY: VARIANT
<222> LOCATION: (25)..(25)
<223> OTHER INFORMATION: X at position 25 is S or Y
<220> FEATURE:
<221> NAME/KEY: VARIANT
<222> LOCATION: (29)..(29)
<223> OTHER INFORMATION: X at position 29 is I or L
<220> FEATURE:
<221> NAME/KEY: VARIANT
<222> LOCATION: (30)..(30)
<223> OTHER INFORMATION: X at position 30 is I or S
<220> FEATURE:
<221> NAME/KEY: VARIANT
<222> LOCATION: (61)..(61)
<223> OTHER INFORMATION: X at position 61 is P or S
<220> FEATURE:
<221> NAME/KEY: VARIANT
<222> LOCATION: (62)..(62)

<223> OTHER INFORMATION: X at position 62 is V or S
<220> FEATURE:
<221> NAME/KEY: VARIANT
<222> LOCATION: (71)..(71)
<223> OTHER INFORMATION: X at position 71 is R or V

<400> SEQUENCE: 28

```
Xaa Val Gln Leu Gln Xaa Xaa Gly Xaa Gly Leu Xaa Lys Pro Ser Glu
 1               5                  10                  15

Thr Leu Ser Leu Thr Cys Xaa Val Xaa Gly Phe Ser Xaa Xaa Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Xaa Xaa Leu Lys
    50                  55                  60

Ser Arg Val Thr Ile Ser Xaa Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Tyr Gly Leu Phe Pro Phe Tyr Phe Asp Tyr Trp Gly Gln
            100                 105                 110

Gly Val Leu Val Thr Val Ser Ser
            115                 120
```

<210> SEQ ID NO 29
<211> LENGTH: 113
<212> TYPE: PRT
<213> ORGANISM: artificial
<220> FEATURE:
<223> OTHER INFORMATION: consensus sequence of a VL of a humanized
      anti-IL-23 antibody
<220> FEATURE:
<221> NAME/KEY: VARIANT
<222> LOCATION: (1)..(1)
<223> OTHER INFORMATION: X at position 1 is E or D
<220> FEATURE:
<221> NAME/KEY: VARIANT
<222> LOCATION: (4)..(4)
<223> OTHER INFORMATION: X at position 4 is M or L
<220> FEATURE:
<221> NAME/KEY: VARIANT
<222> LOCATION: (9)..(9)
<223> OTHER INFORMATION: X at position 9 is A or D
<220> FEATURE:
<221> NAME/KEY: VARIANT
<222> LOCATION: (10)..(10)
<223> OTHER INFORMATION: X at position 10 is S or T
<220> FEATURE:
<221> NAME/KEY: VARIANT
<222> LOCATION: (12)..(12)
<223> OTHER INFORMATION: X at position 12 is A or S
<220> FEATURE:
<221> NAME/KEY: VARIANT
<222> LOCATION: (13)..(13)
<223> OTHER INFORMATION: X at position 13 is V or L
<220> FEATURE:
<221> NAME/KEY: VARIANT
<222> LOCATION: (15)..(15)
<223> OTHER INFORMATION: X at position 15 is P or L
<220> FEATURE:
<221> NAME/KEY: VARIANT
<222> LOCATION: (22)..(22)
<223> OTHER INFORMATION: X at position 22 is N or S
<220> FEATURE:
<221> NAME/KEY: VARIANT
<222> LOCATION: (49)..(49)
<223> OTHER INFORMATION: X at position 49 is A or P
<220> FEATURE:
<221> NAME/KEY: VARIANT
<222> LOCATION: (51)..(51)

```
<223> OTHER INFORMATION: X at position 51 is K or R
<220> FEATURE:
<221> NAME/KEY: VARIANT
<222> LOCATION: (64)..(64)
<223> OTHER INFORMATION: X at position 64 is V or I
<220> FEATURE:
<221> NAME/KEY: VARIANT
<222> LOCATION: (83)..(83)
<223> OTHER INFORMATION: X at position 83 is R or S
<220> FEATURE:
<221> NAME/KEY: VARIANT
<222> LOCATION: (85)..(85)
<223> OTHER INFORMATION: X at position 85 is Q or E
<220> FEATURE:
<221> NAME/KEY: VARIANT
<222> LOCATION: (86)..(86)
<223> OTHER INFORMATION: X at position 86 is A or P
<220> FEATURE:
<221> NAME/KEY: VARIANT
<222> LOCATION: (89)..(89)
<223> OTHER INFORMATION: X at position 89 is F or V
<220> FEATURE:
<221> NAME/KEY: VARIANT
<222> LOCATION: (106)..(106)
<223> OTHER INFORMATION: X at position 106 is G or Q
<220> FEATURE:
<221> NAME/KEY: VARIANT
<222> LOCATION: (110)..(110)
<223> OTHER INFORMATION: X at position 110 is L or V

<400> SEQUENCE: 29

Xaa Ile Val Xaa Thr Gln Ser Pro Xaa Xaa Leu Xaa Xaa Ser Xaa Gly
1               5                   10                  15

Glu Arg Ala Thr Ile Xaa Cys Lys Pro Ser Gln Ser Leu Leu Ser Ser
            20                  25                  30

Gly Asn Arg Lys Asn Tyr Leu Ala Trp Tyr Gln Gln Lys Pro Gly Gln
        35                  40                  45

Xaa Pro Xaa Leu Leu Ile Tyr Tyr Ala Ser Thr Arg Gln Ser Gly Xaa
    50                  55                  60

Pro Asp Arg Phe Ser Gly Ser Gly Ser Gly Thr Asp Phe Thr Leu Thr
65                  70                  75                  80

Ile Ser Xaa Leu Xaa Xaa Glu Asp Xaa Ala Val Tyr Tyr Cys Leu Gln
                85                  90                  95

His Phe Asn Tyr Pro Trp Thr Phe Gly Xaa Gly Thr Lys Xaa Glu Ile
            100                 105                 110

Lys

<210> SEQ ID NO 30
<211> LENGTH: 450
<212> TYPE: PRT
<213> ORGANISM: artificial
<220> FEATURE:
<223> OTHER INFORMATION: humanized antibody heavy chain number 20

<400> SEQUENCE: 30

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Phe Ser Leu Ile Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Ser Val Leu Lys
    50                  55                  60

Ser Arg Val Thr Ile Ser Val Asp Thr Ser Lys Asn Gln Phe Ser Leu
65                  70                  75                  80
```

Lys Leu Ser Ser Val Thr Ala Ala Asp Thr Ala Val Tyr Tyr Cys Ala
            85                  90                  95

Arg Asp Lys Tyr Gly Leu Phe Pro Gly Tyr Phe Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 31
<211> LENGTH: 450
<212> TYPE: PRT
<213> ORGANISM: artificial
<220> FEATURE:

<223> OTHER INFORMATION: humanized antibody heavy chain number 21

<400> SEQUENCE: 31

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Phe Ser Leu Ile Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Ser Val Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 32
<211> LENGTH: 450
<212> TYPE: PRT
<213> ORGANISM: artificial
<220> FEATURE:
<223> OTHER INFORMATION: humanized antibody heavy chain number 6

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Ser Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 33
<211> LENGTH: 450
<212> TYPE: PRT
<213> ORGANISM: artificial
<220> FEATURE:
<223> OTHER INFORMATION: humanized antibody heavy chain number 8

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Ser Tyr
            20                  25                  30

Asn Val His Trp Ile Arg Gln Pro Pro Gly Lys Gly Leu Glu Trp Ile
            35                  40                  45

Gly Val Ile Trp Thr Gly Gly Ser Thr Asp Tyr Asn Pro Ser Leu Lys
50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

```
Pro Ser Asn Thr Lys Val Asp Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
            435                 440                 445
Gly Lys
    450

<210> SEQ ID NO 34
<211> LENGTH: 450
<212> TYPE: PRT
<213> ORGANISM: artificial
<220> FEATURE:
<223> OTHER INFORMATION: humanized antibody heavy chain number 9

<400> SEQUENCE: 34

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Ile Ser Tyr
            20                  25                  30
Asn Val His Trp Ile Arg Gln Pro Pro Gly Lys Gly Leu Glu Trp Ile
        35                  40                  45
Gly Val Ile Trp Thr Gly Gly Ser Thr Asp Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
            85                  90                  95
Arg Asp Lys Tyr Gly Leu Phe Pro Gly Tyr Phe Asp Tyr Trp Gly Gln
            100                 105                 110
```

-continued

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450

<210> SEQ ID NO 35
<211> LENGTH: 450
<212> TYPE: PRT
<213> ORGANISM: artificial
<220> FEATURE:
<223> OTHER INFORMATION: humanized antibody heavy chain number 16

<400> SEQUENCE: 35

Gln Val Gln Leu Gln Glu Ser Gly Pro Gly Leu Val Lys Pro Ser Gln
1               5                   10                  15
```

-continued

```
Thr Leu Ser Leu Thr Cys Thr Val Ser Gly Phe Ser Leu Ile Ser Tyr
         20                  25                  30

Asn Val His Trp Ile Arg Gln Pro Pro Gly Lys Gly Leu Glu Trp Ile
         35                  40                  45

Gly Val Ile Trp Thr Gly Gly Ser Thr Asp Tyr Asn Ser Val Leu Lys
 50                  55                  60

Ser Arg Val Thr Met Ser Arg Asp Thr Ser Lys Asn Gln Phe Ser Leu
 65                  70                  75                  80

Lys Val Asn Ser Val Thr Ala Ala Asp Thr Ala Val Tyr Tyr Cys Ala
                 85                  90                  95

Arg Asp Lys Tyr Gly Leu Phe Pro Gly Tyr Phe Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
         355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
```

```
                    435                 440                 445

Gly Lys
    450

<210> SEQ ID NO 36
<211> LENGTH: 450
<212> TYPE: PRT
<213> ORGANISM: artificial
<220> FEATURE:
<223> OTHER INFORMATION: humanized antibody heavy chain number 1

<400> SEQUENCE: 36

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Ser Val Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
```

```
                  340                 345                 350
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 37
<211> LENGTH: 450
<212> TYPE: PRT
<213> ORGANISM: artificial
<220> FEATURE:
<223> OTHER INFORMATION: humanized antibody heavy chain number 13

<400> SEQUENCE: 37

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ile Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Ser Val Leu Lys
    50                  55                  60

Ser Arg Val Thr Met Ser Val Asp Thr Ser Lys Asn Gln Phe Ser Leu
65                  70                  75                  80

Lys Val Asn Ser Val Thr Ala Ala Asp Thr Ala Val Tyr Tyr Cys Ala
                85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                      245                 250                 255
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 38
<211> LENGTH: 450
<212> TYPE: PRT
<213> ORGANISM: artificial
<220> FEATURE:
<223> OTHER INFORMATION: humanized antibody heavy chain number 7

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Asp Lys Tyr Gly Leu Phe Pro Gly Tyr Phe Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145                 150                 155                 160
        Trp Asn Ser Gly Ala Leu Thr Ser Gly Val His Thr Phe Pro Ala Val
                        165                 170                 175
        Leu Gln Ser Ser Gly Leu Tyr Ser Leu Ser Val Val Thr Val Pro
                        180                 185                 190
        Ser Ser Ser Leu Gly Thr Gln Thr Tyr Ile Cys Asn Val Asn His Lys
                        195                 200                 205
        Pro Ser Asn Thr Lys Val Asp Lys Lys Val Glu Pro Lys Ser Cys Asp
        210                 215                 220
        Lys Thr His Thr Cys Pro Pro Cys Pro Ala Pro Glu Leu Leu Gly Gly
        225                 230                 235                 240
        Pro Ser Val Phe Leu Phe Pro Pro Lys Pro Lys Asp Thr Leu Met Ile
                        245                 250                 255
        Ser Arg Thr Pro Glu Val Thr Cys Val Val Val Asp Val Ser His Glu
                        260                 265                 270
        Asp Pro Glu Val Lys Phe Asn Trp Tyr Val Asp Gly Val Glu Val His
                        275                 280                 285
        Asn Ala Lys Thr Lys Pro Arg Glu Glu Gln Tyr Asn Ser Thr Tyr Arg
        290                 295                 300
        Val Val Ser Val Leu Thr Val Leu His Gln Asp Trp Leu Asn Gly Lys
        305                 310                 315                 320
        Glu Tyr Lys Cys Lys Val Ser Asn Lys Ala Leu Pro Ala Pro Ile Glu
                        325                 330                 335
        Lys Thr Ile Ser Lys Ala Lys Gly Gln Pro Arg Glu Pro Gln Val Tyr
                        340                 345                 350
        Thr Leu Pro Pro Ser Arg Asp Glu Leu Thr Lys Asn Gln Val Ser Leu
                        355                 360                 365
        Thr Cys Leu Val Lys Gly Phe Tyr Pro Ser Asp Ile Ala Val Glu Trp
                        370                 375                 380
        Glu Ser Asn Gly Gln Pro Glu Asn Asn Tyr Lys Thr Thr Pro Val
        385                 390                 395                 400
        Leu Asp Ser Asp Gly Ser Phe Phe Leu Tyr Ser Lys Leu Thr Val Asp
                        405                 410                 415
        Lys Ser Arg Trp Gln Gln Gly Asn Val Phe Ser Cys Ser Val Met His
                        420                 425                 430
        Glu Ala Leu His Asn His Tyr Thr Gln Lys Ser Leu Ser Leu Ser Pro
                        435                 440                 445
        Gly Lys
        450

<210> SEQ ID NO 39
<211> LENGTH: 450
<212> TYPE: PRT
<213> ORGANISM: artificial
<220> FEATURE:
<223> OTHER INFORMATION: humanized antibody heavy chain number 11

<400> SEQUENCE: 39

Gln Val Gln Leu Gln Glu Ser Gly Pro Gly Leu Val Lys Pro Ser Glu
        1               5                   10                  15
        Thr Leu Ser Leu Thr Cys Thr Val Ser Gly Gly Ser Ile Ser Ser Tyr
                        20                  25                  30
        Asn Val His Trp Ile Arg Gln Pro Pro Gly Lys Gly Leu Glu Trp Ile
                        35                  40                  45
        Gly Val Ile Trp Thr Gly Gly Ser Thr Asp Tyr Asn Pro Ser Leu Lys
```

```
            50                  55                  60
Ser Arg Val Thr Ile Ser Arg Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Lys Tyr Gly Leu Phe Pro Gly Tyr Phe Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 40
```

```
<211> LENGTH: 450
<212> TYPE: PRT
<213> ORGANISM: artificial
<220> FEATURE:
<223> OTHER INFORMATION: humanized antibody heavy chain number 18

<400> SEQUENCE: 40
```

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Ser Val Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 41
<211> LENGTH: 450
<212> TYPE: PRT
<213> ORGANISM: artificial
<220> FEATURE:
<223> OTHER INFORMATION: humanized antibody heavy chain number 5

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 42
<211> LENGTH: 450
<212> TYPE: PRT
<213> ORGANISM: artificial
<220> FEATURE:
<223> OTHER INFORMATION: humanized antibody heavy chain number 10

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Tyr Gly Leu Phe Pro Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 43
<211> LENGTH: 450
<212> TYPE: PRT
<213> ORGANISM: artificial
<220> FEATURE:
<223> OTHER INFORMATION: humanized antibody heavy chain number 14

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Tyr
            20                  25                  30

Asn Val His Trp Ile Arg Gln Pro Pro Gly Lys Gly Leu Glu Trp Ile
        35                  40                  45

Gly Val Ile Trp Thr Gly Gly Ser Thr Asp Tyr Asn Ser Val Leu Lys
    50                  55                  60

Ser Arg Val Thr Met Ser Arg Asp Thr Ser Lys Asn Gln Phe Ser Leu
65                  70                  75                  80

Lys Val Asn Ser Val Thr Ala Ala Asp Thr Ala Val Tyr Tyr Cys Ala
                85                  90                  95
```

```
Arg Asp Lys Tyr Gly Leu Phe Pro Gly Tyr Phe Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 44
<211> LENGTH: 450
<212> TYPE: PRT
<213> ORGANISM: artificial
<220> FEATURE:
<223> OTHER INFORMATION: humanized antibody heavy chain number 15

<400> SEQUENCE: 44
```

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Tyr
             20                  25                  30

Asn Val His Trp Ile Arg Gln Pro Pro Gly Lys Gly Leu Glu Trp Ile
         35                  40                  45

Gly Val Ile Trp Thr Gly Gly Ser Thr Asp Tyr Asn Ser Val Leu Lys
     50                  55                  60

Ser Arg Val Thr Met Ser Val Asp Thr Ser Lys Asn Gln Phe Ser Leu
 65                  70                  75                  80

Lys Val Asn Ser Val Thr Ala Ala Asp Thr Ala Val Tyr Tyr Cys Ala
                 85                  90                  95

Arg Asp Lys Tyr Gly Leu Phe Pro Gly Tyr Phe Asp Tyr Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
             325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
         355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 45
<211> LENGTH: 220
<212> TYPE: PRT
<213> ORGANISM: artificial
<220> FEATURE:
<223> OTHER INFORMATION: humanized antibody light chain number 4

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Lys Pro Ser Gln Ser Leu Leu Ser Ser
            20                  25                  30

Gly Asn Arg Lys Asn Tyr Leu Ala Trp Tyr Gln Gln Lys Pro Gly Gln
        35                  40                  45

Ala Pro Arg Leu Leu Ile Tyr Tyr Ala Ser Thr Arg Gln Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Leu Gln
                85                  90                  95

His Phe Asn Tyr Pro Trp Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 220
<212> TYPE: PRT
<213> ORGANISM: artificial
<220> FEATURE:
<223> OTHER INFORMATION: humanized antibody light chain number 22

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Pro Ser Gln Ser Leu Leu Ser Ser
            20                  25                  30

Gly Asn Arg Lys Asn Tyr Leu Ala Trp Tyr Gln Gln Lys Pro Gly Gln
        35                  40                  45
```

```
Pro Pro Lys Leu Leu Ile Tyr Tyr Ala Ser Thr Arg Gln Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Leu Gln
                 85                  90                  95

His Phe Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 47
<211> LENGTH: 220
<212> TYPE: PRT
<213> ORGANISM: artificial
<220> FEATURE:
<223> OTHER INFORMATION: humanized antibody light chain number 12

<400> SEQUENCE: 47

Glu Ile Val Met Thr Gln Ser Pro Ala Thr Leu Ser Leu Ser Pro Gly
 1               5                  10                  15

Glu Arg Ala Thr Leu Ser Cys Lys Pro Ser Gln Ser Leu Leu Ser Ser
             20                  25                  30

Gly Asn Arg Lys Asn Tyr Leu Ala Trp Tyr Gln Gln Lys Pro Gly Gln
         35                  40                  45

Ala Pro Arg Leu Leu Ile Tyr Tyr Ala Ser Thr Arg Gln Ser Gly Ile
     50                  55                  60

Pro Ala Arg Phe Ser Gly Ser Gly Ser Gly Thr Asp Phe Thr Leu Thr
 65                  70                  75                  80

Ile Ser Ser Leu Glu Pro Glu Asp Phe Ala Val Tyr Tyr Cys Leu Gln
                 85                  90                  95

His Phe Asn Tyr Pro Trp Thr Phe Gly Gly Gly Thr Lys Ala Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 48
<211> LENGTH: 220
<212> TYPE: PRT
<213> ORGANISM: artificial
<220> FEATURE:
<223> OTHER INFORMATION: humanized antibody light chain number 23

<400> SEQUENCE: 48

Asp Ile Val Met Thr Gln Thr Pro Leu Ser Leu Pro Val Thr Pro Gly
1               5                   10                  15

Glu Pro Ala Ser Ile Ser Cys Lys Pro Ser Gln Ser Leu Leu Ser Ser
            20                  25                  30

Gly Asn Arg Lys Asn Tyr Leu Ala Trp Tyr Leu Gln Lys Pro Gly Gln
        35                  40                  45

Ser Pro Gln Leu Leu Ile Tyr Tyr Ala Ser Thr Arg Gln Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Leu Gln
                85                  90                  95

His Phe Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 49
<211> LENGTH: 121
<212> TYPE: PRT
<213> ORGANISM: artificial
<220> FEATURE:
<223> OTHER INFORMATION: VH of human antibody number ST883/885

<400> SEQUENCE: 49

Gln Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Lys Gly Met Val Arg Gly Tyr Gly Met Asp Val Trp Gly
            100                 105                 110

Gln Gly Thr Thr Val Thr Val Ser Ser
        115                 120
```

<210> SEQ ID NO 50
<211> LENGTH: 112
<212> TYPE: PRT
<213> ORGANISM: artificial
<220> FEATURE:
<223> OTHER INFORMATION: VL of human antibody number ST883/885

<400> SEQUENCE: 50

```
Gln Ser Val Leu Thr Gln Pro Pro Ser Val Ser Gly Ala Pro Gly Gln
 1               5                  10                  15

Arg Val Thr Phe Ser Cys Thr Gly Ser Asp Ser Asn Ile Gly Ala Gly
                20                  25                  30

Tyr Asp Val His Trp Tyr Gln Gln Phe Pro Gly Arg Ala Pro Lys Leu
            35                  40                  45

Leu Ile Tyr Gly Thr Asn Asn Arg Pro Ser Gly Val Pro Asp Arg Phe
        50                  55                  60

Ser Gly Ser Lys Ser Gly Ala Ser Ala Ser Leu Ala Ile Thr Gly Leu
 65                  70                  75                  80

Gln Val Glu Asp Glu Ala Asp Tyr Tyr Cys Gln Thr Phe Asp Thr Arg
                 85                  90                  95

Leu Ile Ala Ser Val Phe Gly Gly Gly Thr Gln Leu Thr Val Leu Gly
            100                 105                 110
```

<210> SEQ ID NO 51
<211> LENGTH: 5
<212> TYPE: PRT
<213> ORGANISM: artificial
<220> FEATURE:
<223> OTHER INFORMATION: CDR1 of a VH of human antibody number ST883/885

<400> SEQUENCE: 51

```
Ser Tyr Ala Met His
 1               5
```

<210> SEQ ID NO 52
<211> LENGTH: 17
<212> TYPE: PRT
<213> ORGANISM: artificial
<220> FEATURE:
<223> OTHER INFORMATION: CDR2 of a VH of human antibody number ST883/885

<400> SEQUENCE: 52

```
Val Ile Ser Tyr Asp Gly Ser Asn Lys Tyr Tyr Ala Asp Ser Val Lys
 1               5                  10                  15

Gly
```

<210> SEQ ID NO 53
<211> LENGTH: 12
<212> TYPE: PRT
<213> ORGANISM: artificial
<220> FEATURE:

-continued

<223> OTHER INFORMATION: CDR3 of a VH of human antibody number ST883/885

<400> SEQUENCE: 53

Glu Lys Gly Met Val Arg Gly Tyr Gly Met Asp Val
1               5                   10

<210> SEQ ID NO 54
<211> LENGTH: 14
<212> TYPE: PRT
<213> ORGANISM: artificial
<220> FEATURE:
<223> OTHER INFORMATION: CDR1 of a VL of human antibody number ST883/885

<400> SEQUENCE: 54

Thr Gly Ser Asp Ser Asn Ile Gly Ala Gly Tyr Asp Val His
1               5                   10

<210> SEQ ID NO 55
<211> LENGTH: 7
<212> TYPE: PRT
<213> ORGANISM: artificial
<220> FEATURE:
<223> OTHER INFORMATION: CDR2 of a VL of human antibody number ST883/885

<400> SEQUENCE: 55

Gly Thr Asn Asn Arg Pro Ser
1               5

<210> SEQ ID NO 56
<211> LENGTH: 11
<212> TYPE: PRT
<213> ORGANISM: artificial
<220> FEATURE:
<223> OTHER INFORMATION: CDR3 of a VL of human antibody number ST883/885

<400> SEQUENCE: 56

Gln Thr Phe Asp Thr Arg Leu Ile Ala Ser Val
1               5                   10

<210> SEQ ID NO 57
<211> LENGTH: 360
<212> TYPE: DNA
<213> ORGANISM: artificial
<220> FEATURE:
<223> OTHER INFORMATION: nucleotide sequence encoding a VH of humanized
      antibody heavy chain number 20

<400> SEQUENCE: 57
gaggtgcagc tgcagcagtg gggagccggc ctgctgaagc ccagcgagac actgagcctg      60
acctgcgccg tgtacggatt cagcctgatc agctacaacg tgcactggat cagacagccc    120
cctggcaagg gcctggaatg gatcggcgtg atctggaccg gcggcagcac cgactacaac    180
agcgtgctga gtccagagt gaccatcagc gtggacacca gcaagaacca gttcagcctg    240
aagctgagca gcgtgacagc cgccgacacc gccgtgtact actgcgccag agataagtac    300
ggcctgttcc ccggctactt cgactactgg ggccagggca ccctggtgac agtgtcctca    360

<210> SEQ ID NO 58
<211> LENGTH: 360
<212> TYPE: DNA
<213> ORGANISM: artificial
<220> FEATURE:
<223> OTHER INFORMATION: nucleotide sequence encoding a VH of humanized
      antibody heavy chain number 21

<400> SEQUENCE: 58

```
gaggtgcagc tgcagcagtg gggagccggc ctgctgaagc ccagcgagac actgagcctg    60
acctgcgccg tgtacggatt cagcctgatc agctacaacg tgcactggat cagacagccc   120
cctggcaagg gcctggaatg gatcggcgtg atctggaccg gcggcagcac cgactacaac   180
agcgtgctga gtccagagt gaccatcagc cgggacacca gcaagaacca gttcagcctg   240
aagctgagca gcgtgacagc cgccgacacc gccgtgtact actgcgccag agataagtac   300
ggcctgttcc ccggctactt cgactactgg ggccagggca ccctggtgac agtgtcctca   360
```

<210> SEQ ID NO 59
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 6

<400> SEQUENCE: 59

```
caggtgcagc tgcaggaatc tggccctggc ctggtgaaac ccagcgagac actgagcctg    60
acctgcaccg tgtccggctt cagcatcagc agctacaacg tgcactggat cagacagccc   120
cctggcaagg gcctggaatg gatcggcgtg atctggaccg gcggctccac cgactacaac   180
cccagcctga gtccagagt gaccatcagc cgggacacca gcaagaacca gttcagcctg   240
aagctgagca gcgtgacagc cgccgacacc gccgtgtact actgcgccag agataagtac   300
ggcctgttcc ccggctactt cgactactgg ggccagggca ccctggtgac agtgtcctca   360
```

<210> SEQ ID NO 60
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 8

<400> SEQUENCE: 60

```
caggtgcagc tgcaggaatc tggccctggc ctggtgaaac ccagcgagac actgagcctg    60
acctgcaccg tgtccggctt cagcctgatc agctacaacg tgcactggat cagacagccc   120
cctggcaagg gcctggaatg gatcggcgtg atctggaccg gcggctccac cgactacaac   180
cccagcctga agtccagagt gaccatcagc cgggacacca gcaagaacca gttcagcctg   240
aagctgagca gcgtgacagc cgccgacacc gccgtgtact actgcgccag agataagtac   300
ggcctgttcc ccggctactt cgactactgg ggccagggca ccctggtgac agtgtcctca   360
```

<210> SEQ ID NO 61
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 9

<400> SEQUENCE: 61

```
caggtgcagc tgcaggaatc tggccctggc ctggtgaaac ccagcgagac actgagcctg    60
acctgcaccg tgtccggctt cagcctgatc agctacaacg tgcactggat cagacagccc   120
cctggcaagg gcctggaatg gatcggcgtg atctggaccg gcggctccac cgactacaac   180
cccagcctga agtccagagt gaccatcagc gtggacacca gcaagaacca gttcagcctg   240
aagctgagca gcgtgacagc cgccgacacc gccgtgtact actgcgccag agataagtac   300
```
ggcctgttcc ccggctactt cgactactgg ggccagggca ccctggtgac agtgtcctca    360

<210> SEQ ID NO 62
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 16

<400> SEQUENCE: 62
caggtgcagc tgcaggaatc tggccctggc ctggtgaaac ccagccagac actgagcctg    60
acctgcaccg tgtccggctt cagcctgatc agctacaacg tgcactggat cagacagccc    120
cctggcaagg gcctggaatg gatcggcgtg atctggaccg gcggctccac cgactacaac    180
agcgtgctga gtccagagt gaccatgagc cgggacacca gcaagaacca gttcagcctg    240
aaggtgaaca gcgtgacagc cgccgacacc gccgtgtact actgcgccag agataagtac    300
ggcctgttcc ccggctactt cgactactgg ggccagggca ccctggtgac agtgtcctca    360

<210> SEQ ID NO 63
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 1

<400> SEQUENCE: 63
gaggtgcagc tgcagcagtg gggagccggc ctgctgaagc ccagcgagac actgagcctg    60
acctgcgccg tgtacggagg cagcttcagc agctacaacg tgcactggat cagacagccc    120
cctggcaagg gcctggaatg gatcggcgtg atctggaccg gcggcagcac cgactacaac    180
agcgtgctga gtccagagt gaccatcagc cgggacacca gcaagaacca gttcagcctg    240
aagctgagca gcgtgacagc cgccgacacc gccgtgtact actgcgccag agataagtac    300
ggcctgttcc ccggctactt cgactactgg ggccagggca ccctggtgac agtgtcctca    360

<210> SEQ ID NO 64
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 13

<400> SEQUENCE: 64
caggtgcagc tgcaggaatc tggccctggc ctggtgaaac ccagccagac actgagcctg    60
acctgcaccg tgtccggctt cagcctgatc agctacaacg tgcactggat cagacagccc    120
cctggcaagg gcctggaatg gatcggcgtg atctggaccg gcggctccac cgactacaac    180
agcgtgctga gtccagagt gaccatgagc gtggacacca gcaagaacca gttcagcctg    240
aaggtgaaca gcgtgacagc cgccgacacc gccgtgtact actgcgccag agataagtac    300
ggcctgttcc ccggctactt cgactactgg ggccagggca ccctggtgac agtgtcctca    360

<210> SEQ ID NO 65
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 7

<400> SEQUENCE: 65
caggtgcagc tgcaggaatc tggccctggc ctggtgaaac ccagcgagac actgagcctg    60
acctgcaccg tgtccggcgg cagcctgagc agctacaacg tgcactggat cagacagccc   120
cctggcaagg gcctggaatg gatcggcgtg atctggaccg gcggctccac cgactacaac   180
cccagcctga gtccagagt gaccatcagc cgggacacca gcaagaacca gttcagcctg    240
aagctgagca gcgtgacagc cgccgacacc gccgtgtact actgcgccag agataagtac   300
ggcctgttcc ccggctactt cgactactgg ggccagggca ccctggtgac agtgtcctca   360

<210> SEQ ID NO 66
<211> LENGTH: 360
<212> TYPE: DNA
<213> ORGANISM: artificial
<220> FEATURE:
<223> OTHER INFORMATION: nucleotide sequence encoding a VH of humanized
      antibody heavy chain number 11

<400> SEQUENCE: 66
caggtgcagc tgcaggaatc tggccctggc ctggtgaaac ccagcgagac actgagcctg    60
acctgcaccg tgtccggcgg cagcatcagc agctacaacg tgcactggat cagacagccc   120
cctggcaagg gcctggaatg gatcggcgtg atctggaccg gcggctccac cgactacaac   180
cccagcctga gtccagagt gaccatcagc cgggacacca gcaagaacca gttcagcctg    240
aagctgagca gcgtgacagc cgccgacacc gccgtgtact actgcgccag agataagtac   300
ggcctgttcc ccggctactt cgactactgg ggccagggca ccctggtgac agtgtcctca   360

<210> SEQ ID NO 67
<211> LENGTH: 360
<212> TYPE: DNA
<213> ORGANISM: artificial
<220> FEATURE:
<223> OTHER INFORMATION: nucleotide sequence encoding a VH of humanized
      antibody heavy chain number 18

<400> SEQUENCE: 67
gaggtgcagc tgcagcagtg gggagccggc ctgctgaagc ccagcgagac actgagcctg    60
acctgcgccg tgtacggagg cagcttcagc agctacaacg tgcactggat cagacagccc   120
cctggcaagg gcctggaatg gatcggcgtg atctggaccg gcggcagcac cgactacaac   180
agcgtgctga gtccagagt gaccatcagc gtggacacca gcaagaacca gttcagcctg    240
aagctgagca gcgtgacagc cgccgacacc gccgtgtact actgcgccag agataagtac   300
ggcctgttcc ccggctactt cgactactgg ggccagggca ccctggtgac agtgtcctca   360

<210> SEQ ID NO 68
<211> LENGTH: 360
<212> TYPE: DNA
<213> ORGANISM: artificial
<220> FEATURE:
<223> OTHER INFORMATION: nucleotide sequence encoding a VH of humanized
      antibody heavy chain number 5

<400> SEQUENCE: 68
caggtgcagc tgcaggaatc tggccctggc ctggtgaaac ccagcgagac actgagcctg    60
acctgcaccg tgtccggcgg cagcatcatc agctacaacg tgcactggat cagacagccc   120
cctggcaagg gcctggaatg gatcggcgtg atctggaccg gcggctccac cgactacaac   180

```
cccagcctga agtccagagt gaccatcagc cgggacacca gcaagaacca gttcagcctg    240
aagctgagca gcgtgacagc cgccgacacc gccgtgtact actgcgccag agataagtac    300
ggcctgttcc ccggctactt cgactactgg ggccagggca ccctggtgac agtgtcctca    360
```

<210> SEQ ID NO 69
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 10

<400> SEQUENCE: 69

```
caggtgcagc tgcaggaatc tggccctggc ctggtgaaac ccagcgagac actgagcctg     60
acctgcaccg tgtccggcgg cagcatcagc agctacaacg tgcactggat cagacagccc    120
cctggcaagg gcctggaatg gatcggcgtg atctggaccg gcggctccac cgactacaac    180
cccagcctga agtccagagt gaccatcagc gtggacacca gcaagaacca gttcagcctg    240
aagctgagca gcgtgacagc cgccgacacc gccgtgtact actgcgccag agataagtac    300
ggcctgttcc ccggctactt cgactactgg ggccagggca ccctggtgac agtgtcctca    360
```

<210> SEQ ID NO 70
<211> LENGTH: 360
<212> TYPE: DNA
<213> ORGANISM: artificial
<220> FEATURE:
<223> OTHER INFORMATION: nucleotide sequence encoding a VH of humanized antibody heavy chain number 14

<400> SEQUENCE: 70

```
caggtgcagc tgcaggaatc tggccctggc ctggtgaaac ccagccagac actgagcctg     60
acctgcaccg tgtccggcgg cagcatcagc agctacaacg tgcactggat cagacagccc    120
cctggcaagg gcctggaatg gatcggcgtg atctggaccg gcggctccac cgactacaac    180
agcgtgctga agtccagagt gaccatgagc cgggacacca gcaagaacca gttcagcctg    240
aaggtgaaca gcgtgacagc cgccgacacc gccgtgtact actgcgccag agataagtac    300
ggcctgttcc ccggctactt cgactactgg ggccagggca ccctggtgac agtgtcctca    360
```

<210> SEQ ID NO 71
<211> LENGTH: 360
<212> TYPE: DNA
<213> ORGANISM: Artificial
<220> FEATURE:
<223> OTHER INFORMATION: nucleotide sequence encoding a VH of humanized antibody heavy chain number 15

<400> SEQUENCE: 71

```
caggtgcagc tgcaggaatc tggccctggc ctggtgaaac ccagccagac actgagcctg     60
acctgcaccg tgtccggcgg cagcatcagc agctacaacg tgcactggat cagacagccc    120
cctggcaagg gcctggaatg gatcggcgtg atctggaccg gcggctccac cgactacaac    180
agcgtgctga agtccagagt gaccatgagc gtggacacca gcaagaacca gttcagcctg    240
aaggtgaaca gcgtgacagc cgccgacacc gccgtgtact actgcgccag agataagtac    300
ggcctgttcc ccggctactt cgactactgg ggccagggca ccctggtgac agtgtcctca    360
```

<210> SEQ ID NO 72
<211> LENGTH: 342
<212> TYPE: DNA

<213> ORGANISM: Artificial
<220> FEATURE:
<223> OTHER INFORMATION: nucleotide sequence encoding a VL of humanized
     antibody light chain number 4

<400> SEQUENCE: 72

| | | |
|---|---|---|
| gagatcgtgc tgacccagag ccctgccacc ctgtctctga gccctggcga gagagccacc | 60 |
| ctgagctgca agcccagcca gagcctgctg agcagcggca accggaagaa ctacctggct | 120 |
| tggtatcagc agaagcccgg ccaggccccc agactgctga tctactacgc cagcacccgg | 180 |
| cagagcggca tccccgatag attcagcggc agcggctccg gcaccgactt caccctgacc | 240 |
| atcagccggc tggaacccga ggacttcgcc gtgtactact gcctgcagca cttcaactac | 300 |
| ccctggacct tcggcggagg caccaaggtg gaaatcaagc gt | 342 |

<210> SEQ ID NO 73
<211> LENGTH: 342
<212> TYPE: DNA
<213> ORGANISM: Artificial
<220> FEATURE:
<223> OTHER INFORMATION: nucleotide sequence encoding a VL of humanized
     antibody light chain number 22

<400> SEQUENCE: 73

| | | |
|---|---|---|
| gacatcgtga tgacccagag ccccgacagc ctggccgtgt ctctgggcga gcgggccacc | 60 |
| atcaactgca agcccagcca gagcctgctg agcagcggca accggaagaa ctacctggcc | 120 |
| tggtatcagc agaagcccgg ccagccccc aagctgctga tctactacgc cagcacccgg | 180 |
| cagagcggcg tgcccgatag attttctggc agcggctctg gaaccgactt caccctgacc | 240 |
| atcagcagcc tgcaggccga ggacgtggcc gtgtactact gcctgcagca cttcaactac | 300 |
| ccctggacct tcggacaggg caccaagctg gaaatcaagc gt | 342 |

<210> SEQ ID NO 74
<211> LENGTH: 342
<212> TYPE: DNA
<213> ORGANISM: Artificial
<220> FEATURE:
<223> OTHER INFORMATION: nucleotide sequence encoding a VL of humanized
     antibody light chain number 12

<400> SEQUENCE: 74

| | | |
|---|---|---|
| gagatcgtga tgacccagag ccccgccacc ctgtctctga gccctggcga gagagccacc | 60 |
| ctgagctgca agcccagcca gagcctgctg agcagcggca accggaagaa ctacctggct | 120 |
| tggtatcagc agaagcccgg ccaggccccc agactgctga tctactacgc cagcacccgg | 180 |
| cagagcggca tccctgccag attttctggc agcggcagcg gcaccgactt caccctgacc | 240 |
| atcagcagcc tggaacccga ggacttcgcc gtgtactact gcctgcagca cttcaactac | 300 |
| ccctggacct tcggcggagg caccaaggcc gagatcaagc gt | 342 |

<210> SEQ ID NO 75
<211> LENGTH: 342
<212> TYPE: DNA
<213> ORGANISM: Artificial
<220> FEATURE:
<223> OTHER INFORMATION: nucleotide sequence encoding a VL of humanized
     antibody light chain number 23

<400> SEQUENCE: 75

| | | |
|---|---|---|
| gacatcgtga tgacccagac cccctgagc ctgcctgtga cacctggcga gcccgctagc | 60 |
| atcagctgca agcctagcca gagcctgctg agcagcggca accggaagaa ctacctggct | 120 |

```
tggtatctgc agaagcccgg acagagccct cagctgctga tctactacgc cagcacccgg    180
cagagcggcg tgcccgatag attttctggc agcggcagcg gcaccgactt caccctgaag    240
atcagccggg tggaagccga ggacgtgggc gtgtactact gcctgcagca cttcaactac    300
ccctggacct tcggccaggg caccaagctg gaaatcaagc gt                       342
```

<210> SEQ ID NO 76
<211> LENGTH: 363
<212> TYPE: DNA
<213> ORGANISM: Artificial
<220> FEATURE:
<223> OTHER INFORMATION: nucleotide sequence encoding VH of human
      antibody number ST883/885

<400> SEQUENCE: 76

```
caggtgcagc tggtggagtc tgggggaggc ttggtcaagc ctggagggtc cctgagactc    60
tcctgtgcag cctctggatt caccttcagt agctatgcta tgcactgggt ccgccaggct    120
ccaggcaagg gctggagtg gtggcagtt atatcatatg atggaagcaa taaatactac     180
gcagactccg tgaagggccg attcaccatc tccagagaca attccaagaa cacgctgtat    240
ctgcaaatga acagcctgag agctgaggac acggctgtgt attactgtgc gaagaaaaag    300
ggtatggttc ggggctacgg tatggacgtc tggggccaag gaccacggt caccgtctcc     360 tca                                                                   363
```

<210> SEQ ID NO 77
<211> LENGTH: 336
<212> TYPE: DNA
<213> ORGANISM: Artificial
<220> FEATURE:
<223> OTHER INFORMATION: nucleotide sequence encoding VL of human
      antibody number ST883/885

<400> SEQUENCE: 77

```
cagtctgtgc tgacgcagcc gccctcagtg tctggggccc cagggcagag ggtcaccttc    60
tcgtgcactg ggagcgactc caacattggg gccggttatg atgtacactg gtaccagcag    120
tttccaggga gagcccccaa actcctcatc tatggtacca caatcggcc gtcagggtc      180 cctgaccgat tctccggctc caagtctggc gcctcagcct ccctggccat cactgggctc    240
caagttgaag atgaggctga ttattattgt cagacttttg acactcgcct gattgcctcg    300
gtgttcggcg gaggcaccca gctgaccgtc ctaggt                              336
```

<210> SEQ ID NO 78
<211> LENGTH: 497
<212> TYPE: PRT
<213> ORGANISM: Artificial
<220> FEATURE:
<223> OTHER INFORMATION: fusion protein comprising the following linked
      components: IL-12p40-linker-IL-23p19

<400> SEQUENCE: 78

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60
```

```
Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Thr Thr Asn Asp Val Pro His Ile Gln Cys Gly Asp Gly
    370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480
```

Val Ala Val Ala Ala Arg Val Phe Ala His Gly Ala Ala Thr Leu Ser
            485                 490                 495

Pro

<210> SEQ ID NO 79
<211> LENGTH: 11
<212> TYPE: PRT
<213> ORGANISM: Artificial
<220> FEATURE:
<223> OTHER INFORMATION: HIS tag

<400> SEQUENCE: 79

Lys Arg Val His His His His His His His
1               5                   10

<210> SEQ ID NO 80
<211> LENGTH: 36
<212> TYPE: PRT
<213> ORGANISM: Artificial
<220> FEATURE:
<223> OTHER INFORMATION: AviHIS tag

<400> SEQUENCE: 80

Lys Arg Val Gly Ser Ile Glu Gly Arg Gly Ser Gly Leu Asn Asp Ile
1               5                   10                  15

Phe Glu Ala Gln Lys Ile Glu Trp His Glu Gly Ser His His His
            20                  25                  30

His His His His
        35

<210> SEQ ID NO 81
<211> LENGTH: 16
<212> TYPE: PRT
<213> ORGANISM: artificial
<220> FEATURE:
<223> OTHER INFORMATION: leader sequence of a heavy chain of an antibody

<400> SEQUENCE: 81

Met Ala Trp Met Met Leu Leu Leu Gly Leu Leu Ala Tyr Gly Ser Gly
1               5                   10                  15

<210> SEQ ID NO 82
<211> LENGTH: 22
<212> TYPE: PRT
<213> ORGANISM: artificial
<220> FEATURE:
<223> OTHER INFORMATION: leader sequence of a light chain of an antibody

<400> SEQUENCE: 82

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 83
<211> LENGTH: 105
<212> TYPE: PRT
<213> ORGANISM: artificial
<220> FEATURE:
<223> OTHER INFORMATION: human light chain lambda constant region

<400> SEQUENCE: 83

Gln Pro Lys Ala Ala Pro Ser Val Thr Leu Phe Pro Pro Ser Ser Glu
1               5                   10                  15

-continued

```
Glu Leu Gln Ala Asn Lys Ala Thr Leu Val Cys Leu Ile Ser Asp Phe
            20              25                  30

Tyr Pro Gly Ala Val Thr Val Ala Trp Lys Ala Asp Ser Ser Pro Val
        35              40                  45

Lys Ala Gly Val Glu Thr Thr Thr Pro Ser Lys Gln Ser Asn Asn Lys
    50              55                  60

Tyr Ala Ala Ser Ser Tyr Leu Ser Leu Thr Pro Glu Gln Trp Lys Ser
65              70                  75                  80

His Arg Ser Tyr Ser Cys Gln Val Thr His Glu Gly Ser Thr Val Glu
            85                  90                  95

Lys Thr Val Ala Pro Thr Glu Cys Ser
            100             105
```